(12) United States Patent
Fischell et al.

(10) Patent No.: US 11,980,450 B1
(45) Date of Patent: *May 14, 2024

(54) ADVANCED CARDIOVASCULAR MONITORING SYSTEM WITH NORMAL, ELEVATED, AND HIGH HEARTRATE THRESHOLDS

(71) Applicant: ANGEL MEDICAL SYSTEMS, INC., Eatontown, NJ (US)

(72) Inventors: David R. Fischell, Fair Haven, NJ (US); Michael Sasha John, Long Branch, NJ (US); David Keenan, Tinton Falls, NJ (US); Steve Johnson, Rochester, NY (US); Gregg Turi, Hackettstown, NJ (US)

(73) Assignee: Avertix Medical, Inc., Eatontown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/819,842

(22) Filed: Aug. 15, 2022

Related U.S. Application Data

(63) Continuation of application No. 17/304,679, filed on Jun. 24, 2021, now Pat. No. 11,426,089.

(Continued)

(51) Int. Cl.
*A61B 5/00* (2006.01)
*A61B 5/024* (2006.01)
(Continued)

(52) U.S. Cl.
CPC ........ *A61B 5/02405* (2013.01); *A61B 5/0022* (2013.01); *A61B 5/0031* (2013.01);
(Continued)

(58) Field of Classification Search
CPC . A61B 5/02405; A61B 5/0022; A61B 5/0031; A61B 5/29; A61B 5/352;
(Continued)

(56) References Cited

U.S. PATENT DOCUMENTS

2007/0093720 A1* 4/2007 Fischell ................ A61B 5/349
600/509

* cited by examiner

*Primary Examiner* — Scott M. Getzow
(74) *Attorney, Agent, or Firm* — Rosenberg, Klein & Lee

(57) ABSTRACT

Systems and Methods are disclosed for detecting acute coronary syndrome (ACS) events, arrythmias, heart rate abnormalities, medication problems such as non-compliance or ineffective amount or type of medication, and demand/supply related cardiac ischemia. The system may have both implanted and external components that communicate with a Physicians's programmer, and smart-devices for monitoring and alerting to detected medically relevant events or states. At least one processor provides event detection using statistical threshold criteria calculated upon at least a portion of a patient's data/distributions and set for a patient or based upon what a doctor determines as abnormal for a patient. Cardiovascular condition is tracked using histogram, trend, and summary information related to heart rate and/or cardiac features such as S-T segment measures of heartbeats. Heartbeats with elevated rates, and below a "high" range, provide medically relevant detections including medication non-compliance where the patient is alerted through a patient alerting mechanism of an abnormality in the heart rate or ST shifts of the patient.

34 Claims, 24 Drawing Sheets

Related U.S. Application Data

(60) Provisional application No. 62/705,397, filed on Jun. 25, 2020.

(51) Int. Cl.
*A61B 5/29* (2021.01)
*A61B 5/352* (2021.01)
*A61B 5/355* (2021.01)
*A61B 5/358* (2021.01)

(52) U.S. Cl.
CPC ............... *A61B 5/29* (2021.01); *A61B 5/352* (2021.01); *A61B 5/355* (2021.01); *A61B 5/358* (2021.01); *A61B 5/686* (2013.01); *A61B 5/7405* (2013.01); *A61B 5/742* (2013.01); *A61B 5/7455* (2013.01); *A61B 5/746* (2013.01)

(58) Field of Classification Search
CPC ......... A61B 5/355; A61B 5/358; A61B 5/686; A61B 5/7405; A61B 5/742; A61B 5/7455; A61B 5/746
See application file for complete search history.

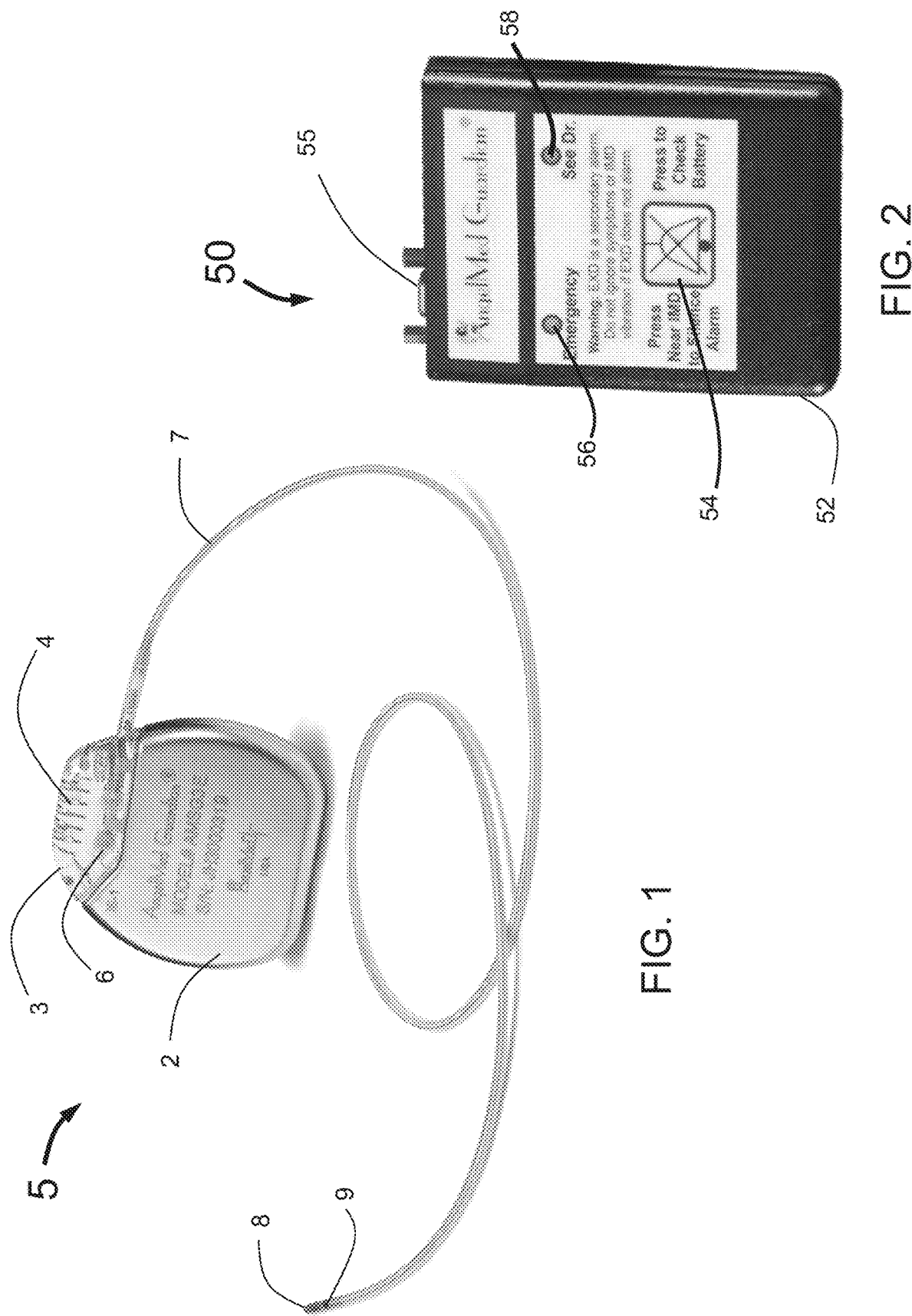

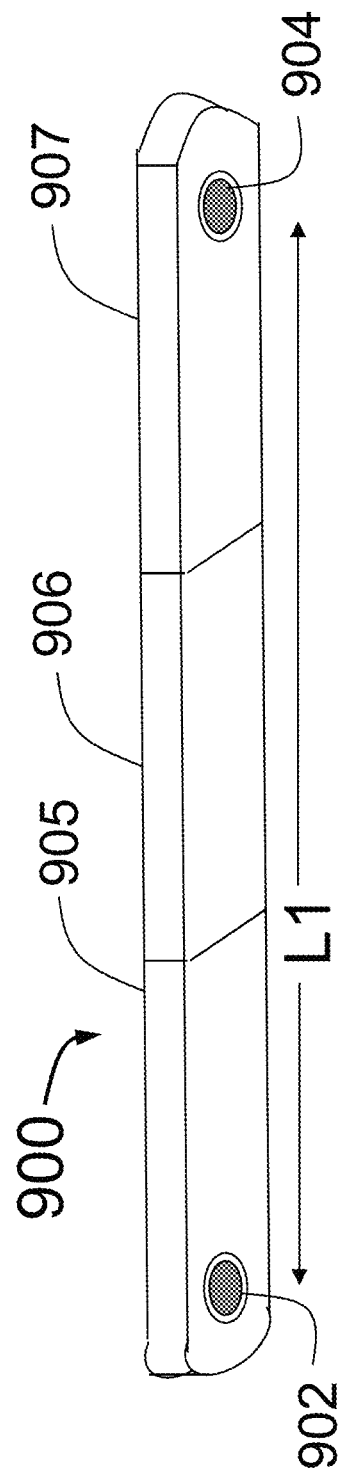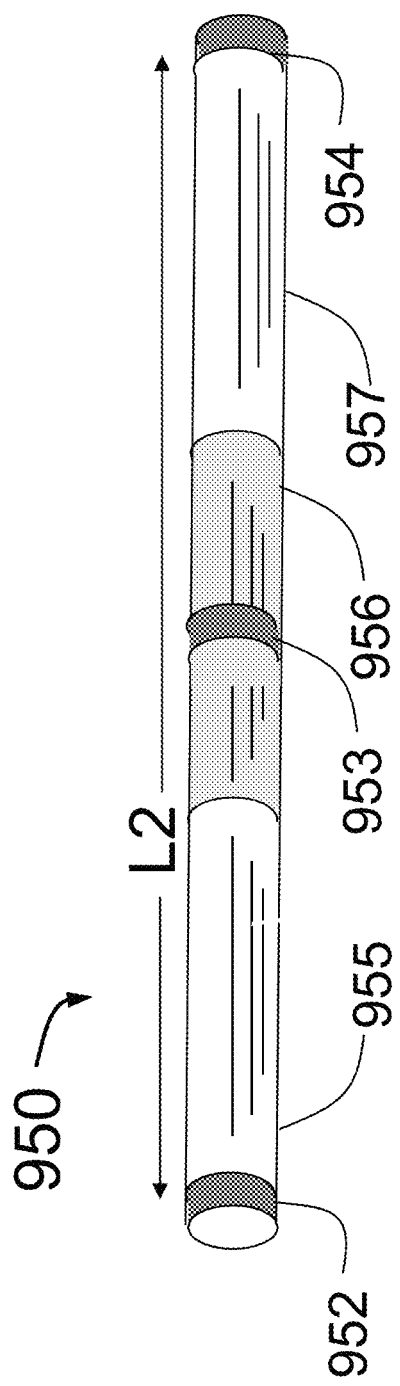
FIG. 15A
FIG. 15B

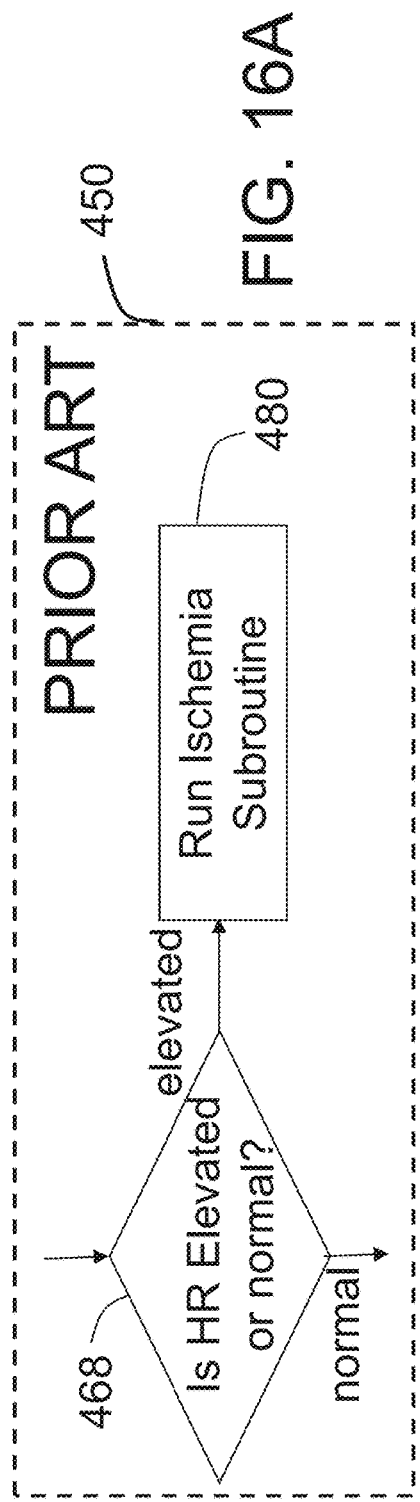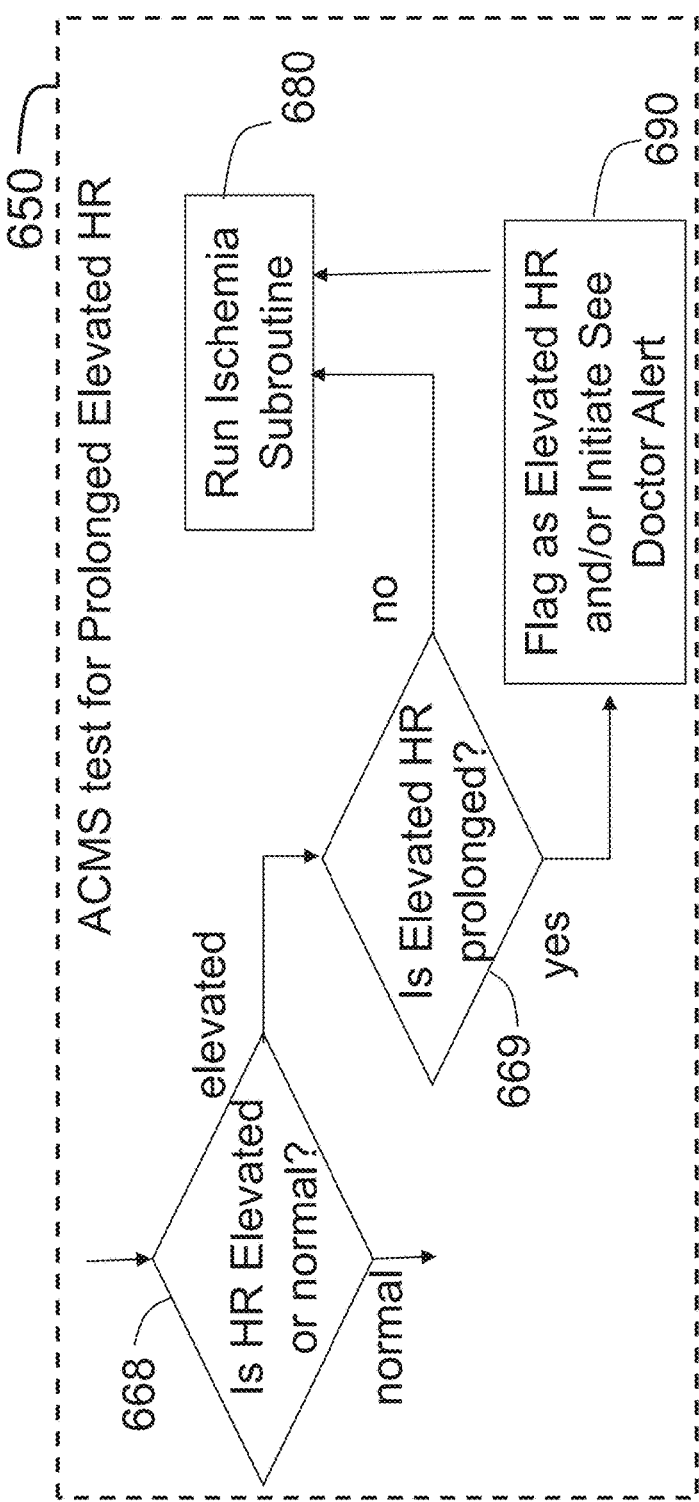

ADVANCED CARDIOVASCULAR MONITORING SYSTEM WITH NORMAL, ELEVATED, AND HIGH HEARTRATE THRESHOLDS

RELATED PATENT APPLICATIONS

This patent is a continuation-in-part of U.S. patent application Ser. No. 17/304,679, entitled "Advanced Cardiovascular Monitoring System with Normal, Elevated, and High Heartrate Thresholds" filed Jun. 24, 2021 which claims priority to U.S. Provisional App. No. 62/705,397 filed Jun. 25, 2020, both of which are incorporated by reference for all intents and purposes.

FIELD OF USE

This invention is in the field of systems that monitor, detect, or treat medical events and conditions of patient especially as related to cardiovascular health.

INCORPORATION BY REFERENCE

U.S. Pat. Nos. 6,112,116, 6,272,379, 6,609,023, 6,985,771, 7,107,096, 7,512,438, 7,558,623, 7,801,596, 7,844,323, 7,860,559, 8,002,701, 8,024,028, 8,038,624, 8,170,653, 8,244,338, 8,265,740, 8,512,257, 8,630,702, 8,655,434, 8,676,304, 8,838,215, 9,101,278, 9,468,383 and 9,788,739 are hereby collectively incorporated by reference.

U.S. Pat. Nos. 8,396,542, 8,406,862, 8,428,703, 8,427,704, 8,560,055, 8,682,422, 8,781,566, 9,031,644, 9,042,969, 9,375,151, 9,414,757 and 9,943,244 are hereby collectively incorporated by reference.

U.S. Pat. No. 11,357,439 entitled "Advanced Cardiovascular Monitoring System with Personalized ST-Segment Thresholds" and U.S. application Ser. No. 17/806,661, filed 13 Jun. 2022 are both hereby collectively incorporated by reference.

Prior Publications, Gibson et al, JACC 2019 vol. 73 No. 15, p 1919-1927; Holmes et al, JACC 2019 vol. 74, No. 16, 2019 p 2047-2055; and Kazmi et al. Medical Devices: Evidence and Research 2020 vol. 13 p. 1-12 are hereby collectively incorporated by reference.

BACKGROUND

Heart disease is the leading cause of death in the United States. A heart attack (also known as an acute myocardial infarction (AMI) typically results from a thrombus (i.e., a blood clot) that obstructs blood flow in one or more coronary arteries. AMI is a common and life-threatening complication of coronary artery disease. Myocardial ischemia is caused by an insufficiency of oxygen to the heart muscle. A blood clot totally blocking a coronary artery is often referred to as supply side ischemia as the oxygenated blood cannot get through the blockage. This differs from demand ischemia that is typically provoked by physical activity or other causes of increased heart rate when at least one coronary artery is narrowed by atherosclerosis.

Patients may experience chest discomfort (angina) when the heart muscle is experiencing either demand or supply side ischemia. Those with coronary atherosclerosis are at higher risk for AMI if the plaque becomes further obstructed by thrombus. Those patients who do not have any symptom of ischemia are said to have "silent ischemia" and if no symptoms are present during AMI it is referred to as a "Silent MI". Patents without ischemic symptoms have no warning to tell them to seek medical attention and are therefore at added risk of morbidity and mortality from AMI.

The current treatment for a coronary artery narrowing ("stenosis") is the insertion of a stent to eliminate or reduce coronary ischemia and to prevent the complete blockage of a coronary artery and AMI.

AMI and ischemia may be detected from a patient's electrocardiogram (ECG) by noting an ST segment shift (i.e., voltage change) starting immediately or within a relatively short (less than 5 minutes) period after significant blockage of a coronary artery. However, without the benefit of knowing the patient's normal ECG pattern (i.e., baseline) for comparative purposes, detection from a standard 12 lead ECG can be unreliable.

Prior art does not disclose collecting and storing, in histogram and other formats, certain heart rate measures that can be valuable to the long-term management of cardiac disease patients and which relate to a combination of rate, rhythm, and ischemia assessment.

Prior art subcutaneous loop recorders use two case electrodes spaced 4-6 cm apart to sense heart signal data. Data recording can be triggered automatically when arrhythmias are detected or upon patient "event tagging" using an external device. Loop recorders store subcutaneous ECG data but cannot measure ST segment changes accurately to detect heart attacks due to limitations. Not to be limited by theory, it is thought that using electrodes only 4-6 cm apart is not sufficient to detect ST-changes in coronary arteries since both electrodes will record much of the same waveform. Accordingly, to accurately measure ST-segment changes, the sensors should be located in at least two different regions of the torso, or one can be attached to the heart, preferably being intracardiac, while the other is located more distally from the heart such as in an area near the clavicle. Both high pass filtering and electrode spacing used by loop recorders preclude accurate detection of low frequency measurements of a heart's electrical signal which are needed for detection of ischemia using ST-segment measures.

Pacemakers can track the numbers of paced and not-paced beats. While pacemaker programmers can display the heartbeat data in histogram format, pacemakers do not generate and then operate upon histogram data for various heart signal parameters related to the electrogram waveform. While pacemakers track pacemaker operation, they do not measure or compute heart signal parameter histograms.

Prior art discloses classifying heart rate with respect to a "Normal" range and a "High" heart rate threshold above which tachycardia is present in the patient. Heart rates in the normal range are classified as "Normal." For example, in many patients' normal heart rates when the patient is not exercising or exerting themselves might lie in a range from 50 BPM to 90 BPM. Heart rates below the normal range are classified as "Low." Heart rates above the high heart rate threshold are classified as "High" and heart rates between the upper end of Normal and the High heart rate threshold are classified as "Elevated." Each of these heart rate ranges can have a lower and upper limit that is defined by a doctor (or an algorithm of the device) based upon assessment of the distribution of heart rates seen in the patient (shown graphically or statistically) over a sample period, or can be set in the device using default heart rate ranges that are defined based upon a sample population. The heart rate ranges may also be adjusted based upon accelerometer data related to a patient's activity such as current activity or recent activity over a defined period.

Cardiovascular disease (CVD) patients often use beta-blockers or drugs to promote normal rate and rhythm (e.g., prevent elevated heart rate) and avoid unnecessary strain of the heart. Patient non-compliance and/or difficulty with correct dosing increases risk for extended periods of elevated heart rate. Long-term monitoring of patient heart rate using histogram, trend analysis, and/or summary statistics provides value in CVD patients, however such is not addressed in the prior art.

U.S. Pat. No. 6,609,023 ("the '023 patent") discloses algorithm logic and steps for detection of ischemic and/or occlusive events, and High, Low and Elevated heart rates, but does not disclose detecting extended periods (e.g., hours) of elevated heart rate possibly reflective of beta-blocker non-compliance or incorrect dosing with features disclosed herein that may lead to better medical management of the patient.

U.S. Pat. No. 9,468,383 ('383) in FIG. 16 discloses communication options from an External Alarm Transceiver that can receive alerts and upload data from an implantable medical device (IMD) and then transmits the data locally to commonly referred to smart devices such as smartphones, tablets, physician's programmers or through long distance voice/data communication interfaces to a remote diagnostic center with wireless protocols such as Wi-Fi and/or Bluetooth protocols being used.

Prior art medical devices, for example, many pacemakers, loop recorders and ICDs stop working when they reach end of life without directly warning the patient. While some of these devices use telemetry to identify battery issues such as end-of-life, there is a long felt need for providing differing and detailed systems and methods to provide notification of implanted device impending end of life.

The '023 Patent discloses wireless communication over 1-3 meters with an external device (EXD) having circuitry that allows the patient to abort i.e., "silence" an alarm. In such prior art systems, an "alarm-off" button and related circuitry halts an alarm activated in the EXD or IMD or both. Patient acknowledgement of the alarm using the alarm silence action provides the IMD with timing of patient confirmation which may then lead to contingent provision of further alarming actions. However, prior art systems do not provide circuitry in the EXD itself for tracking timing of obtaining signals from the IMD, obtaining signals from the patient, and obtaining signals from external sources (e.g., obtaining a local or Greenwich clock time from a nearby cellphone or Wi-Fi). Further, such prior art systems, such as that disclosed in U.S. Pat. '023 disclose a reminder alarm that occurs if the alarm is not silenced by patient within a defined time interval. Such prior art systems do not disclose the provision of reminder alarms at one or more times after the patient has silenced an initial alarm. There is the need for a system where continued reminder alarms are provided after the patient silencing an initial alarm. In embodiments the reminder alarms are configurable by the patient and may also occur contingently based upon time of day. For example, more reminders may occur if the patient may be sleeping, or the patient may be required to interact with a technician over a video call until Emergency services arrive.

Prior art systems and methods in general, do not disclose an IMD and Physician's Programmer software and circuitry configured to adjust the intensity of vibrational alerting so that alarms are easily recognized but are not painful to the patient.

The AngelMed Guardian® underwent a pivotal ALERTS study with results that have been published in three articles incorporated by reference herein: Gibson et al, JACC 2019 vol. 73 No. 15, p 1919-1927; Holmes et al, JACC 2019 vol. 74, No. 16, 2019 p 2047-2055; and Kazmi et al. Medical Devices: Evidence and Research 2020 vol. 13 p. 1-12. The AngelMed Guardian is an Acute Coronary (ACS) event detector with a patient alerting that received FDA Approval in 2018. AngelMed made its first commercial sale of the AngelMed Guardian IMD AMSG3-E on Aug. 11, 2020 in Singapore and after FDA approval in June, 2021, had its first US commercial sale on Jul. 27, 2021.

Prior art non-invasive glucose monitors use optical sensors to sense glucose levels for enhanced control of insulin injection levels but have not been incorporated in a cardiac monitor nor have they been applied to a dual-level alerting system such as that disclosed in the AngelMed Guardian®. Since diabetes is a risk factor for ACS events, it would be advantageous to provide additional specified alerting capabilities not disclosed in the prior art. For example, alerting of a patient could be defined for the IMD and/or EXD if a patient's glucose levels became unstable (e.g., changed too quickly) or dropped to a selected level that was defined as dangerous for the patient. In this manner, the implantable or external components of the subject system and method serves to provide a safety net for diabetic patients that could support their self-care by providing an alert to a potential serious medical event related to diabetes or ACS events.

SUMMARY OF THE INVENTION

The present invention Advanced Cardiovascular Monitoring System (ACMS) provides cardiac monitoring and alerting features which are advantageous over the prior art.

In some embodiments, the present invention is realized in medical devices that are devoid of any means to apply electrical energy to the heart or electrically stimulate the heart. As such, these embodiments cannot pace, cardiovert or defibrillate the heart.

In embodiments the ACMS components include an implantable device and an external device both of which can monitor the patient and produce alarms when defined events are detected such as those related to abnormal cardiac rates and rhythms and coronary ischemia/occlusion. A programmer can be used to program the parameters used in the ACMS devices and to exchange data between the devices and the programmer.

In embodiments, an external computer or set of servers may communicate with the implanted or external devices of the ACMS or with the programmer and may be known as an External Support System (ESS).

In embodiments, ACMS capabilities and features include the use of histograms to efficiently store and analyze data to derive and display the distribution of ST-shift levels and to calculate positive and negative thresholds for detection of excessive ST shift indicative of cardiac ischemia and/or ACS events including heart attacks. The threshold calculations are based on statistical calculations including the mean, median and variability of the distribution (e.g., standard deviations) in one Normal and one or more Elevated heart rate ranges.

In embodiments, the present invention enhances individual patient self-referenced excessive ST shift detection threshold setting mechanism by separately computing the positive and negative variability used to define the normal acceptable range of a patient's ST-segment deviation In embodiments, the system includes alerting for detection of extended periods of elevated heart rate above a defined heart rate threshold for and duration using criteria which may be indicative of patient beta blocker non-compliance or improper beta blocker dosing.

In embodiments, the system includes at least two different methods to determine when the battery is nearing end of service (EOS) and determine an appropriate time before EOS to provide patient alerting in advance of the EOS to allow time for the patient to arrange for a device replacement.

In embodiments, a multi-range wireless communication system is realized by the external alarm device (EXD) which may strategically use near-field, mid-field, and far-field communication to decrease power usage and provide other advantages when communicating data and patient input signals.

In embodiments, the ACMS may include reminders or notification protocols defined for alerting the patient (and/or third party) for a specific detected event type, type of alert signal or severity or type, due to a time of day or tied to a sequence of events. Alarms, alerts, associated reminders and/or other types of notification signals can be provided by the IMD, EXD, and through a message or notification to a care giver, medical practitioner and/or patient's phone, tablet or PC and/or to a third-party service.

In an embodiment, the EXD is also configurable to provide a set of different notifications at pre-defined intervals. For example, an EXD communication module may be configured to send a text message to a defined contact (e.g., family member) upon receipt of an alarm from the IMD, or after a delay of for example, 15 minutes, so that the patient is not contacted by a concerned family member prior to calling for an ambulance (e.g., 911). Additionally, in embodiments, the EXD can be designed to assist with detection of and response to ACS event detection and to function as a glucose monitoring/treatment device.

In embodiments, the present invention ACMS also includes means to activate training alarms to allow patients to experience and practice receiving, understanding and/or responding to reminders, alarms, alerts and/or other notifications initiated by the ACMS.

In embodiments, additional features for the EXD operation include defining the use of 1 or more EXDs, a smartphone, a wristwatch, and an external service whereby the patient may be alerted by a set of candidate EXD devices in a particular order. If the patient provides a response to one EXD then the remaining EXDs are not contacted, or if they have been contacted these other devices are sent indication that the patient has responded from the device that the patient interacted with so that these may provide a contingent operation such as halting patient notification.

In embodiments, the ACMS provides additional histogram format data storage to that described in the prior art. The ACMS uses histograms to track ST levels using ST data measures such as ST deviation over a data collection time period. The ACMS uses histograms to track measures such as heart rate, glucose levels, temperature, blood pressure and/or patient activity such as heart signal parameters including: R-R interval variability; R peak height; heart beat size; R wave width; QRS voltage; QRS width; RS width; T wave width and/or amplitude; and T wave *alternans*. In a preferred embodiment, histograms are retained in memory for a pre-set data retention time period of at least a week, for example 2 weeks.

The features of present invention allow for improved patient medical monitoring and care of patients such as ACS patients which are realized as objects of the invention.

An object of the present invention is to have a preferred embodiment to set detection thresholds for identifying an ischemic event from changes in ST segment levels based that is calculated from asymmetric distributions of previously collected ST segment data saved in histogram format. This preferred embodiment will separately determine positive and negative excessive ST shift detection thresholds by separate assessment of positive and negative distributions of ST data histograms such as ST deviation histograms. In embodiments the positive and negative distributions comprise a first distribution and a second distribution, where the first distribution is defined to be more positive then the second distribution. For example, the positive ST deviation distribution would include data from the histogram with ST deviations greater than or equal to zero and the negative ST distribution would include histogram ST deviation data less than zero. In a preferred embodiment, the processing of ST deviation data to calculate excessive ST shift detection thresholds to be compared with values of ST Shift % of recently collected beats involves normalization of reference ST deviation data to a measure of amplitude of the patient's heart signal amplitude over a data collection time period similar to that of the collected ST deviation histogram(s).

In an embodiment, rather than histograms, raw data values are used for ST-shift or ST-deviation values and the positive and negative ischemia detection thresholds are calculated separately based upon at least two different sets of data values.

Another object relates to processing asymmetric distributions of ST histograms to set positive and negative detection thresholds and comprises mirroring of the positive portion of the ST deviation distribution to calculate the positive thresholds based upon a statistical measure such as standard deviation and mirroring of the negative portion of the ST deviation distribution to calculate negative statistical values such as the negative standard deviation.

Another object is to multiply the positive and negative ischemia detection thresholds by adjustment coefficients that are based upon positive and negative distributions for an individual or a suitable population value (e.g., matched demographically).

Another object is to use at least one of a different number of standard deviations for positive and negative ischemia detection thresholds, or a different minimum time interval, or number of sequential or quasi-sequential data segments, across which the ST-measure must be exceeded, or both.

Still another object is to provide an ACMS with at least two methods of determining battery levels such as end of service (EOS) or Effective Replacement Indicator (ERI) and means to alert the patient when either of the two methods indicates that the battery capacity is at a specified level such as being close to being exhausted.

Still another object is to have wireless communication capability in the IMD that can use different ranges of communication to conserve power and provide other advantages. This may include at least two ranges, a near-field proximity range and a longer far-field range.

Still another object is to provide an ACMS that provides reminder alarms based upon event type, time of day, patient preference, and other reminder protocols.

Yet another object is to provide the ability of the ACMS to activate training alarms and protocols that will allow patients, caregivers, and medical practitioners to participate in training practice.

Yet another object is to provide an IMD capable of tracking heart rate/RR interval data for long term patient health monitoring including pre-set detection thresholds.

Yet another object is to provide the ACMS IMD with sensors for monitoring measurements related to a patient's health such as glucose or other chemicals, oxygen levels, or blood pressure.

These and other objects and advantages of the disclosed invention will become obvious to a person of ordinary skill in this art upon reading of the detailed description of this invention including the associated drawings and claims as presented herein.

BRIEF DESCRIPTION OF THE DRAWINGS

FIG. 1 is a schematic view of the AngelMed Guardian® IMD showing an embodiment of the IMD body (or "can"), header, and intracardiac lead.

FIG. 2 is a schematic view of an embodiment of the AngelMed Guardian® EXD.

FIG. 15A is a schematic view of a Subcutaneous Cardiac Monitor (SCM).

FIG. 15B is a schematic view of an additional embodiment of a subcutaneous Cardiac Monitor (SCM).

FIG. 16A shows a flow chart of a prior art system.

FIG. 16B is a flow chart implemented by the IMD, SCM or SSMD of FIG. 3 to detect extended periods of elevated heart rate as may be indicative of improper beta blocker compliance or dosing.

DETAILED DESCRIPTION OF THE INVENTION

Figure 3:
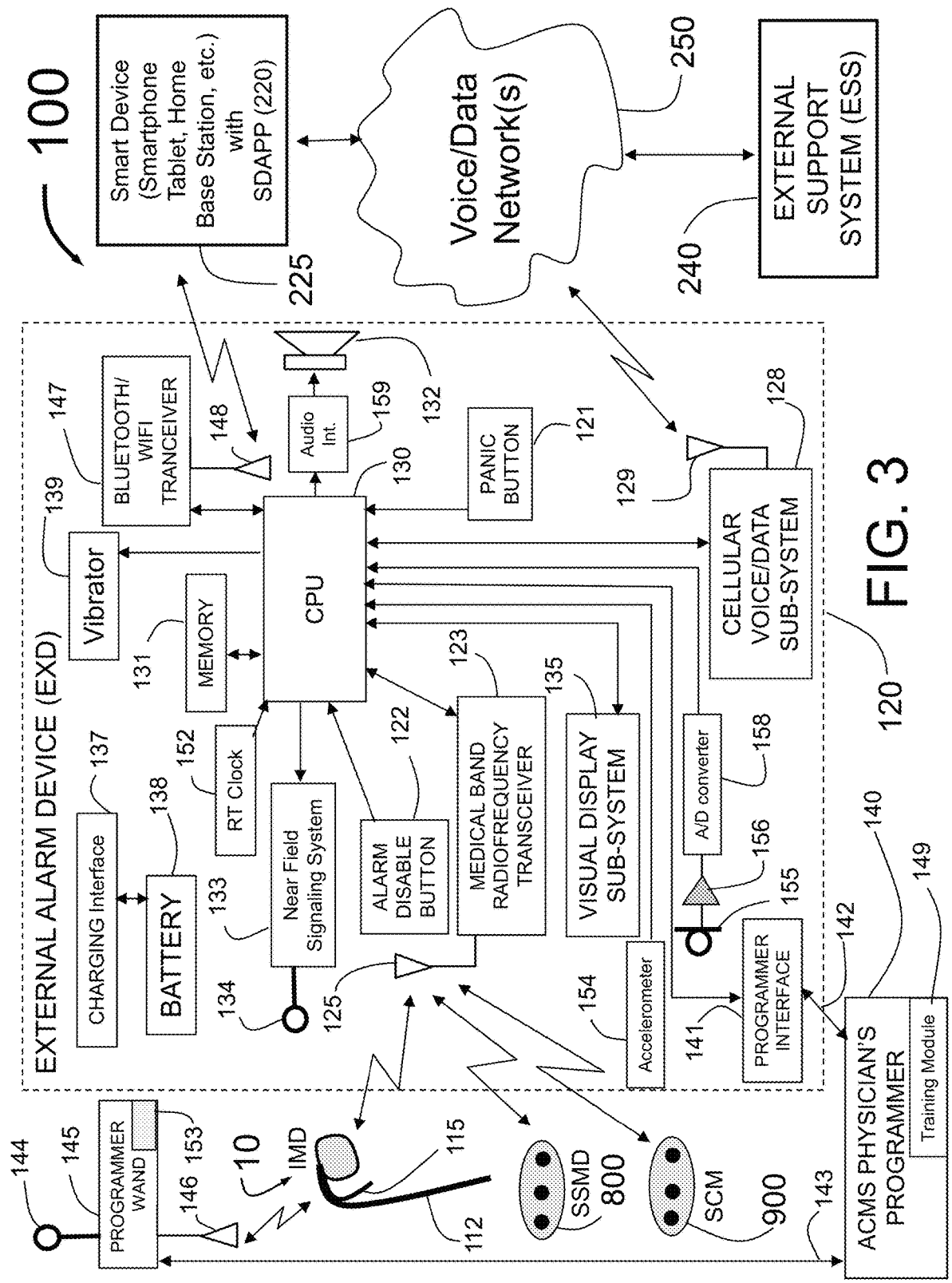
FIG. 3 is a block diagram of the present invention ACMS with its EXD, showing the EXD connects wirelessly to the IMD, Subcutaneous Cardiac Monitor (SCM), Skin Surface Monitoring Device (SSMD) and to the External Support System (ESS), as may be accessed by a Smart Device APP (SDAPP).

When masculine pronouns "he" and "his" are used herein, the patient or medical practitioner may be a man or a woman. For the purposes of this specification the following terms are generally understood as follows:

The term "medical practitioner" is used herein to mean any person involved in the medical treatment of a patient such as a doctor, a medical technician, a paramedic, a nurse or an electrogram analyst;

The term "cardiac event" includes an acute myocardial infarction (AMI), abnormal rate and rhythms including elevated heart rate, bradycardia, tachycardia or an arrhythmia such as atrial fibrillation, atrial flutter, ventricular fibrillation, premature ventricular contractions or premature atrial contractions (PVCs or PACs). Cardiac events may also include demand ischemia caused by effort, such as exercise, or the rejection of a transplanted heart;

The term "electrocardiogram" (ECG) is understood to be the heart's electrical signal. This may be sensed by subcutaneous or skin surface electrodes. An "ECG segment" or "segment" refers to ECG data for either a specific length of time, such as 10 seconds, or a specific number of heart beats, such as 10 beats. An "electrogram segment" refers to a recording of electrogram data collected from an intracardiac or epicardial lead attached to the heart itself. The terms electrocardiogram, ECG and electrogram, may be used interchangeably herein. Systems, methods and algorithms that are described with respect to electrograms should be considered as applicable to embodiments using surface or subcutaneous ECGs;

The PQ segment of a patient's ECG is the typically flat segment of a beat of an ECG that occurs just before the Q and R waves. For the purposes of this specification the ST segment of a patient's ECG is that segment of a beat of an ECG that occurs just after the S wave;

The term QRS voltage is defined as a measure of QRS complex voltage amplitude which may either be measured from Q to R, or S to R of a beat of the ECG. The term QRS segment or QRS complex is that segment of the electrogram from the Q through the R and ending at the J point of the S wave;

The term "beat" is defined as a sub-segment of an ECG segment which covers the electrical signal from the heart for exactly one beat of the heart and includes exactly one R wave. If the heart rate is 60 bpm, then the sub-segment of the electrogram that is exactly one beat would represent a sub-segment of the electrogram that is exactly 1.0 second in duration;

The terms "detection" and "identification" of a cardiac event have the same meaning;

The terms "average value", "average amplitude" or "average voltage" of any segment (viz., QRS complex, ST segment or PQ segment) of the electrogram shall be defined as meaning either the mean or the median of a multiplicity of measurements of that segment. It is also envisioned that in some cases both mean, and median may be computed and will on occasion be described separately herein;

"Heart signal parameters" are defined in embodiments, to be any measured or calculated value created during the processing of one or more beats of ECG/electrogram data. A "beat" being a portion of the heart signal corresponding to 1 heartbeat typically having at least a PQ segment, R wave and an ST segment. Heart signal parameters are features of the electrogram or electrocardiogram derived from one or more measured values and include PQ segment average voltage, ST segment average voltage, R wave peak voltage, ST deviation (ST segment average voltage minus PQ segment average voltage), ST shift i.e., a change in ST deviation of currently sensed data compared to a reference or "baseline" average ST deviation (from reference/baseline heart signal data collected at some prior time), ST shift % is an ST shift normalized to an averaged heart signal amplitude. For clarity, ST shift of a beat from newly acquired heart signal data (that is being evaluated to detect ACS events) is a measure of the change in ST deviation of the beat in the newly acquired data compared to a baseline average/reference ST deviation value from a prior time period. In an embodiment, an average heart signal amplitude would be calculated from heart signal data collected during the same prior time period used to calculate the baseline ST deviation value;

In an embodiment, the PQ segment may extend all the way to the R wave in case where there is no significant Q wave, Other heart signal parameters include average signal strength, T wave peak height, T wave average voltage, T wave deviation, QRS complex width, QRS voltage, heart rate and R-R interval. Counts of the number of arrhythmia related events such as PACs, PVCs and/or episodes of atrial fibrillation are not considered herein to be heart signal parameters as they do not directly result from a measured value derived from a beat of the electrogram;

ST segment related heart signal parameters include, ST segment average voltage, ST deviation, ST shift and ST Shift % which is ST-Shift normalized to an average heart signal amplitude (e.g., QRS amplitude or R-wave amplitude/height). The preferred embodiment of ST Shift % is represented as the ST shift as a percentage of an average heart signal amplitude or strength, e.g., R wave height. ST shift % may also be a fraction or another normalized value. In embodiments, the terms "ST Shift" or "ST shift thresholds" may refer to their normalized embodiments (e.g., the threshold value is normalized as ST Shift %) Any or all of these measures related to evaluation of the ST-segments of patient heartbeats may be referred to as "ST data";

"ST deviation thresholds" are a change in ST deviation that represents a significant change in ST deviation such as 3 standard deviations based on an ST deviation distribution as may be stored using an ST deviation histogram. These may also be referred to as "excessive ST deviation thresholds";

"Positive excessive ST shift thresholds" and "negative excessive ST shift thresholds" represent normalized positive and negative ST deviation thresholds. The normalization is typically to an average heart signal amplitude measured from a data collection time period similar to that used for assessing the ST deviation distribution. In a preferred embodiment, excessive ST shift thresholds are represented as a percentage of the average heart signal amplitude;

"Excessive ST shift" for a beat or beats is a value of ST shift % that is greater than a positive excessive ST shift threshold or more negative than a negative excessive ST shift threshold;

Although "ST deviation" may be defined as the ST segment level compared to iso-electric/PQ segment level, disclosed embodiments may similarly utilize alternative measures of ST deviation including, but not limited to: a) ST level itself represented as a voltage or in ADC or other units, or b) ST level relative to any average signal intensity of a portion of the heart signal from a beat;

The term "data collection time period" should be understood to generally mean the time during which the IMD will be updating a histogram and/or computing an average value of heart signal amplitude from a multiplicity of beats. The data collection period could be as short as 10 seconds and as long as many months. In some embodiments, a data collection time period of 6 to 24 hours can provide important information and may decrease effects from daily biological cycles such as circadian rhythms;

The "data retention time period" should be generally understood to be the period over which sensed data retained in the IMD such as average heart signal amplitude, histograms or histogram sets are stored in IMD memory before these collected data are overwritten with new data. For example, in embodiments, if the data collection time period is one day and there are 5 histograms for 5 different heart rate ranges collected each day and there are 8 sets of histogram memory (each corresponding to a day), then one set will be the current day with histogram stored from the 7 previous days. In that example the collected data retention time period is 7 days and at any one time there would be 40 total histograms;

The "extracted data retention time period" may be generally understood as the period over which the analysis data from an individual histogram (extracted histogram data) is stored in IMD memory before it is overwritten with new data. For example, if the extracted histogram data is the median ST deviation from the day's histogram and that median is stored in IMD memory for 6 months before it is overwritten with new data, then the extracted data retention period is 6 months;

Analog-to-Digital Converter ("ADC") units may be exactly as produced by the Analog-to-Digital Converter. For example, when using 8 bits the values would be values of 0 to 255 representing integer values of −127 to +128. Alternatively, these are scaled from the ADC output (e.g., −63 to plus 64);

Although embodiments of the ACMS may provide urgent Emergency Alarms or "alarms" and less urgent See Doctor Alerts, or "alerts", the terms "alarm" and "alerts" can be used interchangeably to indicate a notification that is provided by the system as part of a patient's health monitoring and/or treatment; and, Capabilities described herein for an IMD and EXD are applicable to, and realizable as part of, any ACMS device. For non-implantable monitors like the SSMD, the EXD function can be integrated within the SSMD. In embodiments, the EXD may be realized using a patient's smartphone or by EXD communication with a smartphone.

Exemplary System Components

FIG. 1 is a schematic view of an embodiment of the invention realized as an AngelMed Guardian® IMD 5. The IMD has a body (or "can") 2, a header 3 and a lead 7. The header 3 includes a helical antenna 4 and an IS1 lead interface 6. The lead 7 is for example an IS1 compatible standard bipolar pacemaker lead with an active fixation lead tip 8 and ring electrode 9. The IMD 5 can be implanted similarly to a single chamber pacemaker with the lead tip 8 imbedded in the heart muscle at or near the apex of a patient's right ventricle. The IMD 5 disclosed herein utilizes some of the features (and corresponding systems and methods) disclosed in prior art patent of the current inventors and having a primary function of alerting patients to ST segment changes indicative of coronary occlusion that may indicate the patient is having a heart attack.

In embodiments, the invention is realized in medical devices that are devoid of any means to apply electrical energy, or otherwise stimulate, the heart. These embodiments cannot pace, cardiovert or defibrillate the heart. In alternative embodiments, the features of the present invention are realized within a device, or which communicates with a device, that provides pacing or defibrillation.

When the features of the present invention are provided in devices that have stimulation circuitry, such as pacemakers, these can be combined with prior-art technology, incorporated by reference herein, disclosed by the inventors such as U.S. Pat. No. 9,415,228, entitled "System for ischemia detection based on adjustable paced beat analysis timing", U.S. Pat. No. 8,452,404 entitled "Ischemia detection systems for paced-patients having three different detection modes" and, U.S. Pat. No. 8,275,457 entitled "Cardiac monitoring system for paced patients having paced and non-paced ischemia detection thresholds".

FIG. 2 is a schematic view of an embodiment of an AngelMed Guardian® EXD 50 with a case 52, a battery door on the reverse side (not shown) housing a replaceable battery inside a battery compartment on the back side (not shown). On the front side of the case 52 is an "Alarm Silence" button 54 and alarm related visual alerts including an Emergency alarm warning LED 56 and a "See Doctor" alert warning LED 58. On the top surface is a serial interface connection port 55 used to connect the EXD 50 to an AngelMed Guardian® Physician's Programmer (not shown). When connected to a Programmer, the EXD 50 may serve as a wireless interface, sometimes referred to as a "Wand", used to communicate with the IMD 5 for programming the IMD 5 or uploading data stored in the IMD 5 to the Programmer. The EXD 50 and Physician's Programmer disclosed herein utilizes some of the features (and corresponding systems and methods) disclosed in prior art systems, incorporated by reference herein. The EXD may be realized without the wand capability which can be realized using a specialized "wand" device.

FIG. 3 is a block diagram of an embodiment of the ACMS 100 including the following components which serve as monitoring and/or alerting devices: an IMD 10; a Subcutaneous Cardiac Monitor (SCM) 900; a Skin Surface Monitoring Device (SSMD) 800; In embodiments the ACMS 100 also includes components that provide for interaction with a user located locally or remotely: an EXD 120; a smart device 225 such as a smartphone, smartwatch, tablet or PC operating software realized as a Smart Device APP (SDAPP) 220; an External Support System (ESS) 240; an ACMS Physician's Programmer 140, and; a programmer "wand" 145 with activation button 153. In embodiments the ACMS 100 also includes the following: physical connection 143, near-field antenna/coil 144 and far-field antenna 146; a voice/data network 250 which may be a cellular network or a data network like the internet or SMS cellular data network that also allows voice connectivity and including network components such as wireless routers and the like for wireless communication with devices such as ACMS 100 devices. In embodiments, the ACMS 100 disclosed herein utilizes some of the features (and corresponding systems and methods) disclosed in the prior art systems, incorporated by reference herein. The ACMS may be realized using different combinations of the components shown in FIG. 3 or can be realized using as any one or more of the components (e.g., IMD 10, SCM 900, SSMD 800). In embodiments, the components of the ACMS 100 such as the IMD 10 and Programmer 140 may communicate to exchange data directly through the wand 145 or via the EXD 120. FIG. 3 shows additional details of an embodiment of the EXD 120 including a microphone 155, acoustic transducer 132, CPU or processor 130 with memory 131, battery 138, event tagging or panic button 121, visual display sub-system 135, programmer interface 141 with connecting cable 142 for physical connection to Physician's Programmer 140, and alarm silence/disable button 122.

In a preferred embodiment of the present invention, the IMD 10 is implanted along with the primary/secondary leads 112/115 that have electrodes that can sense the heart's electrogram. Although the present invention (as described herein) in most cases refers to the preferred embodiment of an IMD 10 which can process electrogram data from pacemaker like implanted electrodes, the techniques described are equally applicable to embodiments integrated into a pacemaker, cardioverter of ICD or using one or more SCMs 900 or an SSMD 800 to process heart signal data from appropriately placed subcutaneous or skin surface electrodes.

In one embodiment of the IMD 10, either or both subcutaneous electrodes or electrodes located on a pacemaker type right ventricular or atrial leads can be used. It is also envisioned that one or more electrodes may be placed within the superior vena cava or other vessels of the circulatory system. Skin surface electrodes or other external or implantable sensors are envisioned as well forming a multi-faceted health monitoring system.

A preferred embodiment of the SSMD 800 or SCM 900 for ST monitoring would have at least three sensing electrode locations. These electrodes may be provided at locations such as below the left clavicle, near the sternum and under the skin on the patient's left side near the bottom of the rib cage. Another embodiment of the IMD 10 could utilize epidural electrodes attached externally to the heart.

ACMS & EXD Communication

In embodiments, the EXD 120 communicates in at least four manners: A) it connects wirelessly to at least one of the IMD 10, SSMD 800 and SCM 900 using at least one modality of wireless communication. One such modality utilizes the near-field signaling system 133 with near-field antenna/coil 134; B) it communicates using a far-field protocol such as the FCC approved medical band through the medical band radiofrequency transceiver 123 and EXD antenna 125. The medical band radiofrequency transceiver 123 would use a chipset such as the Microsemi Zarlink ZL70103 MedRadio product among others. While the medical band is preferred for implanted devices because of its ability to transmit through a patient's skin, low power Bluetooth may be used instead in alternate embodiments; and C) the EXD 12 has a cellular voice/data sub-system 128 with cellular voice/data sub-system antenna 129 which could include a chipset such as the Sierra Wireless LTE-M or equivalent chipset to communicate with voice/data networks. This allows communication to occur with voice/data networks 250 and allows communication with remote computers, such as those located at nearby hospitals; D) the EXD 120 may include a transceiver 147 having Bluetooth or Wi-Fi capacity and antenna 148 to enable communication with ACMS components such as a Smart device 225 that has access to the voice/data network 250.

In embodiments, the voice/data network 250 provides communication with an External Support System (ESS) 240 and/or software "Smart Device APP (SDAPP)" 220 operating on a smart device 225 such as a smartphone, tablet, smart-watch/Fitbit or PC which may provide back-up alerting or function as a home-based station with connectivity of internet, phone line or cellular means to provide for transmission of data collected by the IMD 10, SCM 900 or SSMD 800 through the voice/data networks 250 to other smart devices 225 or an external support system 240. In embodiments, a smart device 225 such as a smartphone, tablet, home base station provides additional functionality such as allowing a patient to have video calls with remote medical personnel. The Smart APP can be customized for different uses including: the patient, a caregiver, paramedics and EMS, Emergency Department (ED) personnel and physicians including GPs and cardiologists.

In embodiments, the EXD processor 130 operates a communication protocol configured to respond to communication signals emitted by a set of at least one IMD 10 or SCM 900 to which it is paired for a particular patient. The EXD-IMD pairing can occur during initial programming session according to a software routine operated by a Physician Programmer. Alternatively, an EXD 120 may allow EXD-IMD pairing if a user to provides particular user input (e.g., pressing a defined sequence using the alarm silence button). For example, providing 5 button presses of about 1 second each causes the EXD software operated by the CPU 130 to initiate a "pairing mode". The pairing mode can be defined in the EXD CPU 130 and provided by a communication module and add the IMD identification information to the EXD memory 131 of the EXD CPU 130. This enables the EXD to pair with a unique IMD 120 which is within the communication range of the EXD 120. Subsequent to this pairing, during an actual alarm event, the IMD 10 or SCM 900 transmits a signal which may be detected by an EXD 120 through its medical band radiofrequency transceiver 123 with EXD antenna 125, but the EXD 120 will not alert unless the alarm signal is from its "paired" IMD 10 or SCM 900.

Alternatively, when two patients live together, it may be advantageous to allow the EXD 120 to have a "multi-pairing mode" defined in the EXD CPU 130 that allows the EXD 120 to be paired to more than one IMD 10 or SCM 900. Alternately, in embodiments the EXD 120 can be set to turn off its "pairing mode" as defined in the EXD CPU 130 to enable the EXD 120 to operate in a non-paired mode which is defined so that the EXD will alert if any IMD 10 or SCM 900 in its vicinity transmits an alert signal. While a multiple-paired mode may be helpful when two family members are patients with implanted devices (since it decreases the risk of an alarm unintentionally being ignored) allowing EXDs 120 to respond to any IMD 10 or SCM 900 may cause confusion or other problem when used in public areas where two strangers may be in proximity to each other upon the triggering of an alarm. Accordingly, pairing modes may be selected by a physician or user, or may be selected by the processor of the EXD 120 based upon geolocation data indicating whether a patient is at home or not. In embodiments, the IMD and EXD communication protocols are configured to allow any EXD to be used to silence the alarm of any IMD.

EXD Event Tagging and Alarm Silencing

The EXD 120 includes an EXD CPU 130 with EXD memory 131. The EXD CPU 130 connects to an alarm silence button 122 realized as similar to the AngelMed Guardian© EXD 50 of FIG. 2. The EXD CPU 130 can also connect to at least one additional button such as an event tagging or panic button 121 which is used by the patient to indicate an event that may need medical review. In embodiments, additional buttons initiate features such as voice or data messaging through the voice/data network 250 as well as sending a command signal to the IMD 10, SSMD 800 or SCM 900 which causes the device to monitor and store data for a defined duration of data for later review. The EXD 120 may include an accelerometer 154 to detect patient motion and activity levels and the accelerometer data can be stored in memory and be associated with Alarm signals and data that is sent to the EXD. In embodiments, this functionality requires a non-near-field IMD wakeup protocol (such as using intermittent far-field monitoring as is possible when using a rechargeable battery) or preferably to reduce battery use would require a patient to hold the EXD near their IMD when sending the event-tagging command signal to the IMD, since the IMD is not monitoring for far-field communication without first being woken up using near-field signals. In an embodiment, the IMD periodically checks for a far-field signal (e.g., every 1-2 minutes) and the EXD is programmed to emit a button press signal until receipt is acknowledged by the IMD.

EXD Patient and Third-Party Alerting

The EXD 120 provides patient alerting by a patient alerting mechanism through its acoustic transducer 132 which may be a loudspeaker or a piezoelectric transducer. Additional alerting is provided by the visual display subsystem 135 that would typically be one or more LEDs, an alpha/numeric display, or a display screen such as a smartphone display. A vibrator 139 may also be incorporated into the EXD 120 as an additional alerting or feedback mechanism. The vibrator 139 may be realized as a piezoelectric transducer, a vibrator motor, or a Linear Resonant Actuator (LRA). An LRA is like a speaker coil driving a mass inside an enclosed case. Similar in size and shape to a pancake style vibrator motor and available with z-axis motion ideal for the patient alerting application. Such an LRA vibrator can be configured and programmed to control the vibration, resonant frequency and add haptic feedback for either the EXD 120 or IMD 10.

Adding connectivity voice/data network 250 enable alarm and alert (with or without captured data) signals sent by the IMD 10, SSMD 800 or SCM 900 to be transmitted to one or more defined contacts (e.g., a relative who may be alerted on their smart device 225 due to operation of the SDAPP 220). Information about the alarm can be obtained without requiring the patient to visit a clinic for upload of data to a Physician's Programmer 140. A defined contact who might receive alarm related notifications include: a patient's cardiologist; an on-call cardiologist for the practice managing the patient; a patient's emergency contact; a patient caregiver; a patient's GP; an Emergency Department selected by the patient; an alarm monitoring service which expedites patient triage and transportation to a medical facility; an Emergency Department that is closest to the patient which is predefined or which is dynamically determined using geo-location methods (e.g., GPS, cellular location, etc.) by software operated by the ESS 240.

In embodiments, the EXD 120 is realized in a smartwatch form factor that provides the alerting capabilities of the EXD 120. The smartwatch could include a vibrator 139 and may have a vibration-only privacy mode defined in the EXD CPU 130 for notification with sound turned off for privacy. The privacy mode selected when the EXD operating parameters are set by a Physician's Programmer 140, may be enabled by the patient in the SDAPP 220 or may incorporated into a physical switch on the housing of the smartwatch, etc. A privacy protocol may also be defined with a sonic alarm is realized as the same sound as a phone call or is unique. The EXD 120 may be realized as, or may communicate with, the SDAPP 220 of a commercially available smart device 225 such as those worn on the wrist (e.g., Apple Watch, Fit-Bit) or may be custom built smartwatch.

Communication Between Physician Programmer, EXD, and Monitoring Devices

In embodiments the EXD 120 includes a Physician's Programmer interface 141 used to physically connect the EXD 120 with the connecting cable 142 to the ACMS Physician's Programmer 140. In one embodiment the EXD 120 serves dual purposes of operating as a patient external alerting system and also operating as the wand for the Physician's Programmer 140 which is used to program an IMD 10, SSMD 800 or SCM 900 and to upload data to the Physician's Programmer 140. Similar to U.S. Patent ('023), the EXD 120 could also use a wireless connection for communication with the Physician's Programmer 140. Connections, for example, may be a serial, USB cable or a Wi-Fi or Bluetooth wireless connection.

Alternatively, the Physician's Programmer 140 uses a physically separate programmer wand 145 (and may have an activation button 153 that is pressed by a user to activate communication with an implanted device), that communicates using a near-field antenna/coil 144 and far-field antenna 146. The wand 145 may utilize a wired or wireless connection 143 for communication with the Physician's Programmer 140. The programmer wand would typically have a device access button (not shown) to initiate near-field or far-field communication to the IMD 10, SSMD 800 or SCM 900 through the near-field antenna/coil 144. Such an initiation would signal the IMD 10, SSMD 800 or SCM 900 to turn on the far-field communication capability so that the remainder of the communication session would occur using far-field signals. Use of a Programmer wand device enables EXD 120 to be produced without the programmer interface 141, however the interface may still be used to retrieve an EXD event log In embodiments the near-field signaling system 133 may be incorporated into an embodiment of the medical band radiofrequency transceiver 123 using one or two antennas.
Patient Notification Protocols and Features of Primary, Secondary, and Reminder Alarms In an embodiment, notification protocols defined in the memory 131 of the EXD 120 can define different notifications to occur at pre-defined intervals. For example, a notification protocol may define an alarm protocol in which the EXD CPU 130 may be configured to provide secondary alerting by sending a text message through the Bluetooth/Wi-Fi transceiver 147 with antenna 148 or the integrated cellular voice/data sub-system 128 with cellular voice/data sub-system antenna 129 to a smart device 225 to a defined contact upon receipt of an alarm signal transmitted by the IMD 10 or SCM 900. This secondary alerting could be immediate or after a delay of for example, 15 minutes, so that the patient is not contacted by a concerned family member prior to calling for an ambulance (e.g., 911).

The alarms can be event-based and triggered by a detected event or may occur according to a predefined schedule. Notifications can be spoken words or text. Examples include, for example: instructions to Call 911 and take an aspirin as part of an Emergency Alarm; instructions to take a beta blocker for an alert for an extended period of elevated heart rate; and, instructions to take an anti-arrhythmia medication for a detected irregular heart rate or AFIB.

An embodiment of the EXD 120 includes a real time clock 152 to provide for local, time-zone adjusted, or international time-based time-stamping of alarms and data for detected events such as saved heart signal parameter data that may be transmitted to the EXD 120 by the IMD 10. The real time clock 152 of the EXD 120 may experience clock-drift and so the processor of the EXD 120 may be configured to adjust the time of the real-time clock using a wireless time synchronization protocol which periodically obtains time updates from a smart device 225 or through the voice/data network 250. The EXD 120 can obtain a time-signal from a smart device 225 through the cellular voice/data sub-system 128 or other source. The clock time (or cumulative counter tick value) of the IMD 10 at the time of the alert, the identification of the Physician's Programmer used to communicate during any data communication operation, the source of the synchronization signal (e.g., smart-phone), time of the synchronization, and any other relevant information (e.g. time zone, any daylight savings time parameters that may be toggled) may be included in a synchronization log stored in the memory 131 of the EXD 120. The order of the devices, and list of permitted devices, which can provide time synchronization signals can be defined by a user or the ACMS Physician's Programmer 140. The ability of the EXD 120 to obtain and store date and time information registered by the EXD 120 and IMD 10 and Physician's Programmer as part of the communication protocol that occurs when communication occurs or is attempted between any of these devices enables accurate determination of the timing of the alarmed event, timing of a button press for event tagging or to calculate the duration between being alarmed and patient input indicating acknowledgment of the alarm, the time at which the EXD 120 establishes communication with a Physician's Programmer (at an Emergency department or ambulance). The communication protocols of the Physician's Programmer and IMD 10 should also allow for sending and receiving timestamp information for added redundancy. Further, the EXD 120 can be configured with RFID or other communication protocol that interacts with internet of things (IOT) sensors/transmitters which are established at Emergency departments to automatically establish the time of arrival of a patient after an alarm occurs.

The battery 138 of the EXD 120 could be rechargeable and operate with charging system 137 realized with a surface interface connector such as a mini-USB, micro-USB, Lightning or USB-C connector and/or a charging coil (not shown) for wireless recharging. While the EXD 120 can connect to the Physician's Programmer 140 through a programmer interface 141, that can also occur wirelessly such as through Wi-Fi or Bluetooth. Inductive EXD 120 charging may occur using standard cell phone inductive charging stands or a home base station version of the smart device 225.

In embodiments, the EXD 120 may have or communicate with sensors for monitoring body temperature, blood pressure, glucose level or Oxygen saturation level, for example, using optical sensors and related methods, or Fatty acid Binding Protein 3 (FRBP3), MI related enzymes such as CPK and/or Troponin which are indicators of a heart attack. The EXD is provided with sufficient circuitry and software to perform the sensing, analyze the monitored data to derive sensed data measures and to provide alerting if a defined medical event is detected.

The ACMS 100 is configured to communicate data including, for example, alarm/alert and heart signal related data from the IMD 10, SSMD 800 or SCM 900 to the ESS 240. The data includes event related data such as data associated with an ischemic event typically characterized by ST changes, heart rate and rhythm related events including arrhythmias, an extended/prolonged period heart rate elevation, direct capture of heart electrocardiogram and electrogram data. Other data for monitoring the cardiovascular condition of a patient can include: ischemia tracking data such as the ST deviation histograms; heart rate tracking data; periodically captured electrocardiogram and electrogram data; data from other sensors such as blood pressure data, blood oxygen saturation data, body temperature, patient activity from an IMD accelerometer 75 etc.; and streamed electrogram data that allows the visualization of the patient's heart signal as it is happening. Streamed data may be in near real time with only small delays associated with data processing and transmission, and can be displayed by the EXD or Physician's programmer 140. To avoid running down the battery of the IMD 10, through use of the wireless transceiver this may be accomplished using a burst mode protocol for communication. For example, 10 seconds of data are stored by the IMD 10 and then transmitted to an external device in a fraction of a second or other limited duration. The burst mode provides time data from a real-time clock or counter of the IMD, to enable the Physician's Programmer 140 to determine the exact time at which the IMD data were recorded to enable these to be temporally aligned with samples of externally recorded data.

Voice connectivity provided by use of the microphone 155 with amplifier 156 and A/D converter 158 and audio interface 159 with acoustic transducer 132 of the EXD 120 can allow a patient and medical practitioner to both speak as may occur during a communication session that is established as part of the post-alerting operations defined in the processor of the EXD 120 in response to a detected event, patient pressing an event tagging or panic button 121, or in response to transmission of longer term tracking data collected by the ACMS 100. Alternately, such voice connectivity can be provided by a patient smart device 225 since current smartphones, tablets or PCs have integrated voice communications capabilities. These can be enhanced further by video apps such as Facetime, Skype or Zoom which are integrated into the post-alerting operations defined in the processor of an EXD 120 or home base station.

Voice connectivity can be used in numerous ways including: A) an automated call from the EXD 120 or patient smart device 225 to a medical practitioner when a cardiac event is detected, B) a call launched by the patient using the EXD 120 or patient smart device 225 after an alarm has occurred, for example by using the panic button 121, C) a data message sent through the voice/data network 250 to a medical practitioner that uses their SDAPP 220 to initiate a voice session with the patient. It is also envisioned that the patient's wired home, cell or work phone, or a wearable like a Fitbit or Apple watch might be activated to provide communication and alarm signals.

In simple embodiment, the ACMS 100 only includes a Physician's Programmer 140 to access and view patient data, a heart monitoring and alerting device (e.g., an IMD 10, SCM 900 or SSMD 800) with the capability to sample electrical signals from a patient's heart, and an EXD 120 with wireless connectivity to the monitoring device which provides alerting to the patient. However, in a more advanced embodiment the EXD 120 would have cellular data connectivity to the voice/data network 250 and an ESS 240 typically in the form of a HIPAA compliant cloud server accessible by medical practitioners, technicians, and care givers through the SDAPP 220. This allows data related to alarms to be reviewed remotely and without delay. Where applicable, EXD 120 capabilities described herein could be combined into the SSMD 800. It is also envisioned that the capabilities described herein may be applicable to wearable systems like the Zoll Life Vest which is a patient worn Automated Electronic Defibrillator (AED) so that this can also provide ACS event detection and alerting.

Communication Between ACMS Devices: Physician Programmer

In embodiments, the Physician's Programmer 140 is used to program the monitoring and alerting devices of the ACMS (e.g., EXD 120, IMD 10, SSMMD 800, or SCM 900) with respect to parameter values for any or all of diagnostic functions, detection criteria, alarming and alerting protocols, and associated adjustable functions. The Physician's Programmer 140 can also be used to retrieve, analyze, and display recorded electrocardiogram/electrogram segments and event related and processed heart signal data from the monitoring and alerting device memory. In an embodiment, the Physician's Programmer 140 includes two modes of operation:

1. A first mode with wired 141 (e.g., through a physical link 142) or wireless 133 communication means that operate when it is in sufficiently close proximity to the EXD 120; and,
2. A second mode where it communicates with the Wi-Fi 147 or cellular data capability 128 of the EXD 120 allowing the monitoring device data to be programmed (via the EXD 120 which in turn communicates with monitoring device) remotely and data stored in the monitoring device to be uploaded to the Physician's Programmer 140. Additional security protocols are envisioned for device programming remotely.

An additional preferred mode of operation of the ACMS 100 is to have alerts based on events detected by the IMD 10, SSMD 800 or SCM 900 that are received by the EXD 120 be communicated directly with the SDAPP 220 on the Smart Device 225 using the Bluetooth/Wi-Fi transceiver 147 with antenna 148. This can provide additional alerting and information to the patient and the cellular or Wi-Fi connectivity of the Smart Device 225 can be used to transmit the alert and related data through the voice/data network 250 to either the external support system 240 or directly to a 3rd party such as a caregiver, cardiologist, emergency department at a local hospital or a medical practitioner or technician that is part of a concierge service. This method has the advantage that the smart device is likely to have patient GPS location that can be of huge benefit should the patient be disabled during a potential event.

It is also envisioned that one or more embodiments of the ACMS 100 of FIG. 3 would include a streamed telemetry mode where the monitoring and alerting devices could stream electrogram/ECG signal data for local display and/or data collection. This feature would be of great benefit for remote patient management or to see existing heart signal data from the patient upon presentation at a medical facility without the need to attach ECG electrodes to the patient's skin. Other measurements sensed by the IMD 10, SSMD 800 or SCM 900 could also be streamed including temperature, blood pressure and O2 saturation.

It is also envisioned that the EXD 120 itself without an associated smart device 225 could provide full connectivity itself through the Voice/Data Network(s) 250 using the Wi-Fi transceiver 148 with antenna 148 and/or cellular voice/data sub-system 128 with antenna 129.

In the 1960s the TV series Star Trek showed a medical bed where without attaching wires to the patient, there could be streamed medical information displayed on a monitor that is in communication with the ACMS that is located above the bed for the doctor's use. This streaming capability can turn the science fiction into reality for patients with an ACMS. The streaming function may be conducted in one of several ways including: A) Use of the EXD 120 as a transceiver to send the streaming data to a smart device 225. This could use the SDAPP 220 that could have a streaming function; and, B) Directly from the IMD 10, SSMD 800 or SCM 900 to a version of the EXD 120 that utilize the wireless technology used by the IMD 10, SSMD 800 or SCM 900.

The Physician's Programmer 140 operates to allow an operator to adjust, select and download to the IMD 10 operating parameters including selected heart rate/R-R interval parameters used for the determination of heart rate ranges and detection thresholds. In an embodiment, the programmer 140 is configured to allow a user to specify and download one or more or all of the following parameters: a) a normal heart rate range having an upper limit and a lower limit; b) a low heart rate threshold below which bradycardia may be detected; c) a high heart rate lower threshold above which tachycardia may be detected; and, d) an elevated heart rate range that lies between the normal heart rate range upper limit and the high heart rate lower threshold. The Programmer also allows a user to select or reject particular sample periods (e.g., days) in a reference dataset which will be used to calculate these limits. Any or all of these may be downloaded to the IMD 10 from a processor other than the programmer 140, either directly, through the EXD 120 or through the voice/data network 250. This can also be calculated in the IMD 10 without assistance of the programmer. The Physician's Programmer 140 can be realized using a customized laptop computer with at least one processor, memory, display, and communications means.

Cardiac Monitoring and Alerting Devices

Figure 4:
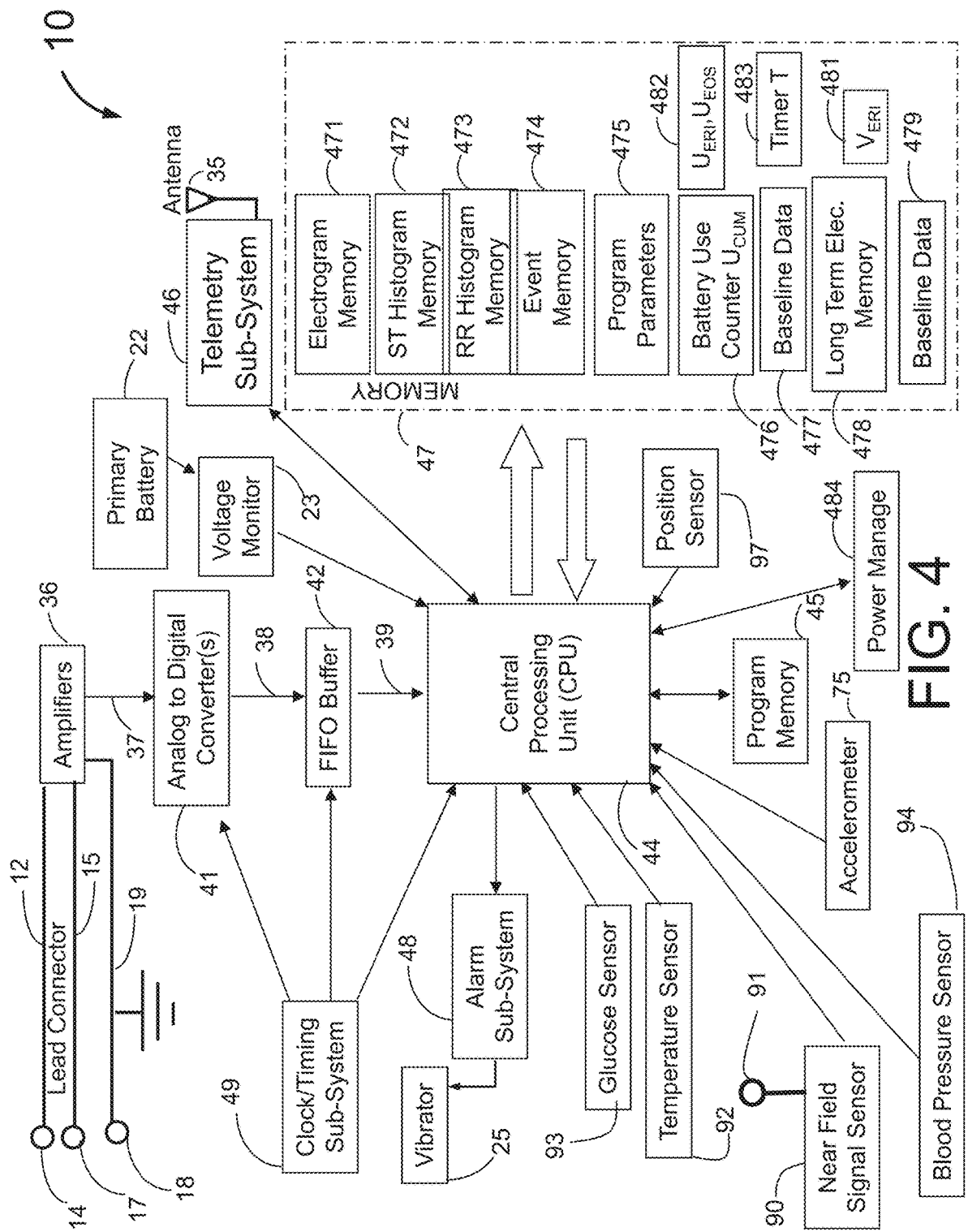
FIG. 4 is a block diagram of the present invention ACMS IMD/SSMD/SCM.

FIG. 4 is a block diagram of an embodiment of an IMD 10. Some of the functionality of the IMD 10 and the SCM 900 is described in prior art systems. The IMD 10 includes a IMD CPU 44, program memory 45, a lead connector with electrodes 14 and 17. The electrodes 14 and 17 may be part of a standard lead interface such as the IS1 pacemaker lead interface 6 of FIG. 1. A feed thru (not shown) is part of the conductors 12 and 15 which connect to the electrodes 14 and 17. The IMD 10 system ground 18 is typically the "can" of the IMD 10. While the term IMD 10 is used here, the block diagram shown in FIG. 4 is also applicable to the SCM 900 and SSMD 800 of FIG. 3 that provide respectively subcutaneous and skin surface electrode sensing of heart signal data.

As seen in FIG. 4 amplifiers 36 through conductor 19 connects to ground 18. The IMD 10 includes memory 47 with allocations including, for example, electrogram memory 471, histogram memory 472, Event Memory 474, Program Parameters Memory 475, Patient Data Memory 477, Long term electrogram memory 478 and Baseline Data memory 479. In addition, the IMD 10 includes analog to digital converter(s) 41, a clock timing sub-system 49, a First-In-First-Out (FIFO) memory buffer 42 feeding digitized heart signal data to the IMD CPU 44. Also included is an Alarm Sub-System 48, a position sensor 97, IMD accelerometer 75, Vibrator 25, Telemetry Sub-System 46 and antenna 35 for wireless data communication to external equipment. It is also envisioned that a microphone (not shown) could be added for additional input to the IMD CPU 44 and can receive voice commands or be used to collect data related to blood-flow or cardiac activity. The clock timing sub-system 49 is coupled to one or more of the analog-to-digital converter 41, FIFO Buffer 42, and IMD CPU 44 for providing control signals in operating the IMD 10.

In implanted cardiac monitors such as the IMD 10 and SCM 900 of FIG. 3 the external system components would typically include the EXD 120 of FIG. 3. For an external embodiment like the SSMD 800 of FIGS. 3 and 14, the telemetry sub-system 46 and antenna 35 could be Bluetooth transceiver to communicate with a computer, smartphone or tablet or could be a cellular voice/data transceiver similar to the cellular voice/data sub-system 128 with cellular voice/data sub-system antenna 129 of the EXD 120 of FIG. 3.

Unlike the prior art systems, the IMD 10 has the additional inclusion of a battery voltage monitor 23, a near-field signal sensor 90 with antenna/coil 91 and additions to the memory 47 (which may be RAM memory) of R-R Interval Histogram Memory 473, Battery Use Data Cumulative Counter ($U_{CUM}$) 476, Timer T 483, Battery Voltage Effective Replacement Indicator (ERI) threshold $V_{ERI}$ 481 and Cumulative battery usage Estimated Replacement Index threshold $U_{ERI}$ 482. Other sensors that may be combined in the IMD 10 include, for example, a Glucose Sensor 93, Temperature Sensor 92 and Blood Pressure Sensor 94. The blood pressure sensor 94 could be best positioned as part of the primary lead 112 or a secondary lead 115 shown in FIG. 3. Battery chemistry of the power source is well known, such as a Lithium Carbon Mono-Fluoride (CFx) chemistry battery.

A preferred embodiment of the telemetry sub-system 46 with antenna 35 uses the FCC approved medical band with Radiofrequency based on a chipset such as the Microsemi ZL70103 MedRadio product among others. Low power Bluetooth is also envisioned as a wireless standard that could be used by the telemetry sub-system 46.

Baseline Data Collection and Use

In a preferred embodiment, each new beat collected by the IMD 10 would be analyzed to measure the ST deviation and the height of the R-wave ("R height"). Periodically, e.g., once an hour, two averages are calculated including a) the average ST deviation of a multiplicity of recently collected beats and b) the average R height of those beats. The two averages are then retained in the baseline data memory 479. The two new averages are also averaged together respectively with the 23 ST deviation averages and 23 R-height values from 23 prior hours stored in the Baseline Data memory 479. The resulting 24-hour "composite baseline" average ST deviation and −24 hour "composite baseline" average R-height are also stored in the Baseline data memory 479 and used by the IMD 10 to compute the ST shift for each newly collected beat as follows:

1. The change in ST deviation for each newly collected beat as compared to the 24-hour baseline average ST deviation is calculated to obtain an ST shift measure,
2. The ST shift % of the newly collected beat is then calculated as the change in ST deviation derived in step 1 normalized to a reference. In a preferred embodiment of this normalization, the ST shift % is expressed as a percentage of the 24-hour baseline average R-height.
3. If the ST shift % is positive, then this is compared to the positive excessive ST shift threshold and if negative to the negative excessive ST shift threshold. If the ST shift % is more positive than the positive excessive ST shift threshold or more negative than the negative excessive ST shift the beat is classified as shifted. In a preferred embodiment, ST shift values that are assessed for beats of the incoming sensed cardiac data and the positive and negative excessive ST shift thresholds are all are normalized and in a preferred embodiment normalized as a percentage of a value of average R-height.
4. The IMD 10 of FIG. 4 would then identify an ischemic event by the presence of one or more shifted beats within a pre-set number of beats or a pre-set time period.
5. As described in the prior art, based on the heart rate of the shifted beats, the type of alarm or alert would be initiated.

It is also envisioned that instead of computing the average ST deviation and R height of the recently collected data and averaging those with the 23 averages from 23 prior hours, the individual beat data from the 23 hourly data collections could instead be averaged. Averaging the averages is preferred as it reduced the amount of data storage required.

In alternative embodiments the baseline reference is generated from samples obtained every 30-180 minute increments and the baseline reference is an average created from 12 or more intervals. For example, the composite baselines average can be generated from 12 baseline samples obtained at 2-hour intervals.

In a preferred embodiment, beats used for analysis and/or baseline creation are selected to represent normal sinus beats of the patient's heart. This would exclude one or more types of abnormal beats such as: PVCs, PACs or beats with abnormally shortened R-R intervals (e.g. above a high heart rate limit i.e. tachycardia); beats with abnormally widened QRS; for baselines only, beats with ST shift % that are greater than a preset percentage of the excessive ST shift threshold, e.g., those with ST shift % greater than half of the excessive ST shift threshold. Baseline beats should also have RR intervals associated with a normal range of heart rate.

Near-Field Communication Protocols

In embodiments, a multi-range wireless communication system is realized by the EXD, ACMS physician's programmer, or other system component to provide near-field (<0.1 meter), mid-field (0.1 to 25 meters), and far-field (>25 meters) communication and is configured for providing features and methods including:

1. Rather than being continuously active, near-field triggering is used to activate longer-range communication circuitry to reduce power use;
2. A near-field mechanism that allows a user to silence alarms is configured to prevent a patient from accidentally depressing a "silence alarm" button 122 on an EXD 120 of FIG. 3. This may be realized by an operational contingency requirement such as requiring a pattern of button presses [3 button presses about one-second each] to be provided sequentially within 5 a second interval. Alternatively, the IMD or EXD may be programmed to ignore button presses on the EXD for at least 30 seconds after Alarm onset.
3. A communication error signal indicating lack of response such as may occur if the EXD 120 is held outside of the near-field range and when the Alarm Silence button 122 of FIG. 3 is depressed (e.g., if the IMD 10 does not respond then a single beep could be provided by the EXD 120 and/or a message of communication error could be displayed).
4. A unique patient notification signal produced by an EXD 120 of FIG. 3 to verify the proper functioning of the IMD. For example, the EXD 120 is held in close (near-field) proximity to the IMD 10 and a button such as the alarm silence button 122 on the EXD 120 is depressed. If the IMD 10 is not functioning and the EXD 120 alarm silence button 122 is depressed, a single beep would be provided by the EXD 120 and/or a message of communication error could be displayed. Alternatively, a single beep could be provided to indicate that the EXD has logged the button press and is sending a signal to the IMD. If the IMD 10 is functioning properly and the button is pressed with the EXD 120 in the near-field of the IMD 10, this would initiate a mid-field communication session between the IMD 10 and EXD 120 and the EXD 120 would deliver two beeps and/or a message about device status could be displayed. This feature enables the patient, caregiver or medical practitioner to verify the IMD 10 is active, and the telemetry communication is working. It is also envisioned the IMD 10 would include additional status data (e.g., IMD battery status, device status/error register, recordings count and clock count) in its transmission to the EXD 120 additional status data including IMD battery status, device status/error register, recordings count and clock count.

The near-field signal sensor 90 with antenna/coil 91 is designed to receive a signal from the near-field signaling system 133 and near-field antenna/coil 134 of the EXD 120 of FIG. 3. The near-field signal sensor 90 provides several important features of the ACMS 100. One feature allows the IMD 10 to have its telemetry sub-system 46 turned off almost all the time and the near-field signaling system 133 of the EXD 120 is configured to cause the IMD 10 CPU 44 to turn on the telemetry sub-system 46 only when needed to conserve power and lengthen the life of the primary battery 22.

Four examples illustrate important uses of near-field communication in embodiments of the ACMS 100.

1. Local programming of, and data retrieval from, an IMD 10 or SCM 900. The programmer wand 145 or EXD 120 of FIG. 3 are connected to the Physician's Programmer 140 of FIG. 3. The EXD 120 is positioned close to (in the near-field of) the implanted IMD 10 and programming session is initiated. This occurs using the wireless communication between the telemetry sub-system 46 with antenna 35 of the IMD 10 and the medical band radiofrequency transceiver 123 with EXD antenna 125 of the EXD 120. The near-field location could be for example against the patient's chest and over the implanted device or within a pre-set distance from the IMD, for example 1-5 cm. The maximum range should be 20 cm or less. This provides an important level of security as it requires access to the device be initiated by placing the EXD 120 right against the patient.

Once in position, a button such as the alarm silence button 122, an event tag button (not shown) or the panic button 121 of the EXD 120 of FIG. 3 is depressed activating the near-field signaling system 133 which sends a signal through the near-field antenna/coil 134 of the EXD 120. That signal is sensed by the IMD 10 near-field signal sensor 90 with antenna/coil 91. The antenna/coil 91 can be a simple coil or some type of antenna or pickup to receive the near-field signal from the EXD 120. In one example, the near-field signal sensor 90 could change the voltage on a pin of the IMD CPU 44 from zero to one indicating a request to turn on the telemetry sub-system 46. The programmer wand 145 activation button 153 of FIG. 3 would typically be used with a similar near-field access technique.

Additional levels of security can be achieved in by either a unique initial signal or with "hand shaking" security protocols that would occur with the EXD 120 or Physician's Programmer 140 begin a far-field communication session with the IMD 10.

2. Silencing alarms. The patient places their EXD 120 of FIG. 3 within the near-field (as just described) and depresses the alarm silence button 122. The IMD CPU 44 of the IMD 10 will receive this signal and terminate the vibratory internal alarm. This will also cause the EXD 120 to a) stop the visual alarms displayed through the visual display subsystem 135 and b) stop audible alarms sent to the acoustic transducer 132 of the EXD 120 of FIG. 3. In embodiments of the present invention this would also trigger the steps of the "reminder alarm" method shown in FIG. 10.

3. Request assistance from a medical practitioner or service support. For example, if the EXD 120 is placed in the near-field and a panic button 121 is depressed, then a unique sound or LED flash might occur to confirm the activation of a "request assistance" or "panic mode" request to the IMD 10. In an embodiment, the IMD 10 would upload all the recent data stored in its memory from the a data collection time period e.g., last 24 hours for transmission through the EXD 120 cellular voice/data sub-system 128 and cellular voice/data sub-system antenna 129 to the ESS 240 of FIG. 3. This can be accompanied by additional message indicating a patient request for assistance. A message can then be sent by the ESS 240 to a medical practitioner who is enabled activate the SDAPP 220 to view the information that would typically also include the patient's contact information or means to enable the voice connection feature in the EXD 120. Alternately, the message with or without associated data, could be sent directly to the smart device 225 of FIG. 3 of a medical practitioner, care giver or technician. This is further discussed in the detailed description of FIG. 18. The person who is contacted would interact with the patient to facilitate their treatment (could be called a cardiac concierge). The operation of the panic button can also cause the EXD 120 to lock in memory 47 current data including electrograms stored in the IMD 10 for later review by a medical practitioner.

4. Device Checking. In embodiments, when the alarm silence button 122 of the EXD 120 is depressed while outside of the near-field range of the IMD 10 or SCM 900 of FIG. 3 this will prompt the occurrence of an acoustic or visual signal on the EXD 120. For example, a single beep or flash of an LED or displayed text message serves as a "device check" or battery-check for the EXD 120 only. This is different than what occurs when the alarm silence button 122 is pressed within the near-field of the IMD 10 or SCM 900 of FIG. 3 in the absence of an alarm or alert. In that case the reception of a near-field signal by the IMD 10 would cause the IMD 10 to turn on its telemetry sub-system 46 and send a confirmation signal to the EXD 120 through the medical band radiofrequency transceiver 123. That, in turn, causes the EXD 120 to provide an additional confirmatory sound, light or both signal (e.g., a 2nd beep and light flash is provided). The device checking, when completed successfully, allows the patient (or medical practitioner) to verify that the IMD 10 is alive and functioning. However, if following the activation of the telemetry sub-system 46 data successful communication does not occur between the IMD 10 and EXD 120 after a time out period, then the IMD 10 telemetry sub-system would turn off to conserve energy. If no communication occurs whatsoever, it is also envisioned that the EXD 120 could display a communication error message using the visual display sub-system 135 of FIG. 3 and save the communication and time information related to the failed communication attempt in EXD memory 131.

In an embodiment, a mechanism for providing a near-field wake-up function for the features 1-4 above is to have the near-field antenna/coil 134 of the EXD 120 and antenna/coil 91 of the IMD 10 both be simple wire coils. The wake-up signal received by the near-field antenna/coil 134 could be a magnetic pulse produced by the near-field signaling system 133 of the EXD 120 of FIG. 3. Such a magnetic pulse can easily go through the skin, be received by the antenna/coil 91 and detected by near-field signal sensor 90. Other embodiments may be realized by versions of the Telemetry Sub-System 46 that have both RF low power near-field and higher power mid-field capabilities. In embodiments, the wake-up feature can be implemented using far-field operations.

In embodiments, detection of the EXD-IMD signals may include a method in which the signal is amplified, filtered, the signal envelope is demodulated, and the signal is then input to the IMD CPU 44. Upon reception of a valid digital data packet the IMD CPU 44 activates the telemetry sub-system 46 and opens a communication session with the medical band radiofrequency transceiver 123 of the EXD 120 of FIG. 3. As the IMD CPU 44 executes it firmware instruction loop as stored in the program memory 45 it will periodically look for the digital data packet from the near-field signal sensor 90. The IMD CPU 44 may be configured to time-out after a pre-set interval if no communication occurs. In a preferred embodiment when a UART in the circuitry of the IMD 10 used to collect the near-field data recognizes a proper message, it interrupts the EXD CPU 44.

The activation button 153 on the programmer wand 145, the alarm silence button 122 and panic button 121 of FIG. 3 may all be used to initiate a communication session between the IMD 10 and EXD 120 using near-field communication. Alternatively, it is also conceived that simply placing the EXD 120 or programmer wand 145 near the IMD 10 could automatically activate the near-field sensor. For example, the IMD 10 and EXD 120 would both be aware that an alarm had occurred because the EXD 120 continuously searching for an IMD communication by operating its medical band radiofrequency transceiver 123. The EXD 120 could be configured to initiate transmission of appropriate near-field pulses that would, in turn activate the near-field signal sensor 90 of the IMD when the EXD 120 is brought within the near-field without the need for the patient to depress the alarm silence button 122.

In another embodiment, the EXD 120 (or programmer wand 145 of FIG. 3) could periodically activate the near-field signaling system 133 by simply placing the EXD 120 in the near-field and allowing it to initiate a communication system. This communication protocol is also practical for the programmer wand 145 that could be configured to begin sending pulses once the Physician's Programmer 140 is turned on. In an embodiment the IMD 10 and EXD 120 may have a "remote wakeup" feature i.e., the IMD 10 would periodically (e.g., daily) activate its far-field receiver so that an EXD 120 within far-field distance could interrogate the IMD 10.

Vibration Alarm

The vibrator 25 of the IMD 10 or the vibrator 139 of the EXD 120 of FIG. 3 may be embodied by a piezoelectric buzzer, a miniature vibrator motor with an off-center weight such as that typically used in cell phones or an LRA, or some like mechanism which provides for a tactile sensation. The IMD 10 alarm sub-system 48 includes means to increase or decrease the intensity of the vibration delivered by the vibrator 25. This can be accomplished through an increase in voltage, current and/or pulse frequency used to turn the vibrator 25 from its off state to its on state. Intensity level may be either a continuous adjustment or preferably a set of about two to 10 preset levels.

Patient Training with the Physician's Programmer and ACMS

In embodiments, the present invention ACMS 100 also includes software routines for patient alarm training that allow patients to experience individually or together the vibratory, auditory and visual alarms/alerts provided by the IMD 10, SSMD 800, SCM 900 and/or EXD 120, or other system components used to notify a patient or remote entity during actual alarm.

The Physician's Programmer 140 includes a training alarm module 149, which enables a medical practitioner to trigger any of the alarms or alerts and activate vibrational and/or acoustic training alarms for 2 or more different intensities and/or patterns. It is envisioned that the training alarm module 149 could also be used to adjust the intensity of the alarm for the IMD 10, SSMD 800, SCM 900 and/or EXD 120. The intensity adjustments can include adjustments for the ACMS 100 alerting mechanisms including vibrators acoustic transducers and/or visual alerts. The training alarm module 149 can adjust intensity and trigger any of the alerting modes of the ACMS 100. For example, if the ACMS 100 includes two modes, Emergency Alarms and See Doctor Alerts as described in the prior art, then the training alarm module 149 can separately turn on and off and adjust intensities of the vibration, sound or visual alerts for either Emergency Alarms and See Doctor Alerts. In addition, one type of alert may be adjusted at a time. For example, just the vibrational levels may be set first without sound or visual alerts to be sure the patient can feel it and it is not so intense as to cause pain. After Vibration level is set, then just the sound and then all three types together.

An example of a training session that includes operating the training alarm module 149 to initiate and adjust vibration alarms would involve the following steps:

Step 1—activate the vibrator 25 to demonstrate Emergency Alarms at 2 or more intensity levels;

Step 2—obtain patient feedback to determine an appropriate level to set the alarm parameters of the IMD 10 (e.g., vibration level as high as possible without being painful).

Step 3—set parameters for Emergency Alarms and/or See Doctor Alerts based on patient feedback.

Step 4—train the patient by providing Emergency Alarms and See Doctor Alerts. This can occur for a particular alarm component (e.g., just for vibration) or using more than one alarm modality, and for the IMD 10 or EXD 120 in isolation, or both together. As part of step 4 the patient is trained to use the EXD 120 of FIG. 3 to silence an alarm using near-field communication.

Step 5—Provide any additional instructions to the patient (e.g., instruction to not ignore symptoms since the alarm may not always occur or severe symptoms may occur earlier).

In embodiments, the Physician's Programmer may set an alarm protocol that is used during times when a patient is likely sleeping that is different than when a patient is likely awake. For example, a sleeping protocol may ramp up alarm vibration strength in sequential steps to a maximum strength that is higher than that which is used when the patient is likely awake.

The training alarm module 149 when used to program the intensity level(s) for actual alerts provided during treatment allows for increasing or decreasing the intensity of the EXD 120 or SSMD 800 acoustic alert to be sure the patient can hear it, and EXD 120 vibration alert if also provided. In addition to the acoustic intensity being adjustable, for example from about 70 dB to 120 dB, the frequency can be modifiable to address patients with low or high frequency hearing loss. Additionally, the tones can include 2 or more alternating frequencies such as 1000 Hz and 2000 Hz to increase the likelihood of the tone being outside of frequency range of hearing loss. In one embodiment, the training alarm module 149 enables adjusting of the pattern or content of one or more types of acoustic alert to make it more detectable by the patient in various manners. For example, patients are more likely to attend to their own name or voice instead of simply tones. The patient (or a caretaker or family member) can record their own name into the EXD 120 which can be played back to them during an alert or may be presented only they fail to press the alarm silence button.

The training alarm module 149 when used to program the intensity level(s) for actual alerts provided during treatment allows for increasing or decreasing the intensity of the EXD 120 or SSMD 800 visual alert to be sure the patient can see it, and in some embodiments adjust the color of the visual alert if it is a flashing light or LED to ensure the patient can tell the difference if they are color blind.

Such training alarms are also important to allow the patient to practice silencing the alarm using the alarm disable button on the EXD 120. In a preferred embodiment this requires the EXD 120 be brought into the range of the near-field signaling system 133 with near-field antenna/coil 134 when the alarm disable button 122 is pressed.

Finally, it is very important that as part of the training session, patients are instructed how to respond to each mode of alarm/alert. For example, typical instruction is to have patients instructed that in response to an Emergency alarm they should call 911 and chew an aspirin, for a See Doctor alert, they should call their doctor now and schedule an appointment within the next few days.

ACMS Operations

The ACMS 100 realizes features supported by the firmware contained in the program memory 45 of the IMD 10 including: 1) monitoring of the primary battery 22 with patient alerting at an appropriate time interval before end of life of the primary battery 22; 2) identification and patient alerting for extended periods of elevated heart rate (e.g. to indicate non-compliance or improper dosing of heart rate regulating medications such as beta blockers); 3) reminder alarms even when the patient properly silences an initial alarm; 4) use of histograms and other tracking methods to monitor patient heart rate/R-R interval; and 5) alarms provided by the EXD 120 of FIG. 3 or the SDAPP 220 (operated on another device) which prompt the patient to perform a pre-specified task or take a medication.

In an embodiment, the IMD 10 is configured to detect and count arrhythmia related events including: a) incidence of PACs or PVCs b) PVC beats per electrogram segment, c) occurrences of two consecutive beats that each have a PVC, d) the incidence and duration of episodes of ventricular tachycardia, e) occurrences of three consecutive PVCs and/or f) the incidence and time duration of episodes of atrial fibrillation. Also envisioned is the identification of T-wave *alternans*. Arrythmia related events are computed using heart signal parameters. In addition to detection and counting of these events, the IMD 10 is configured to store sample waveforms and timestamps for these events.

Data sensed by the IMD can be predictive of ventricular fibrillation. For example, a change in the frequency of beats with a heart signal parameter may be predictive of a forthcoming episode of ventricular fibrillation. In this instance, patient notification may lead to a doctor detecting the new onset of an unknown condition in the patent and medication may be prescribed or an implantable cardioverter defibrillator (ICD) could be implanted.

Power Management and Monitoring

Figure 5:
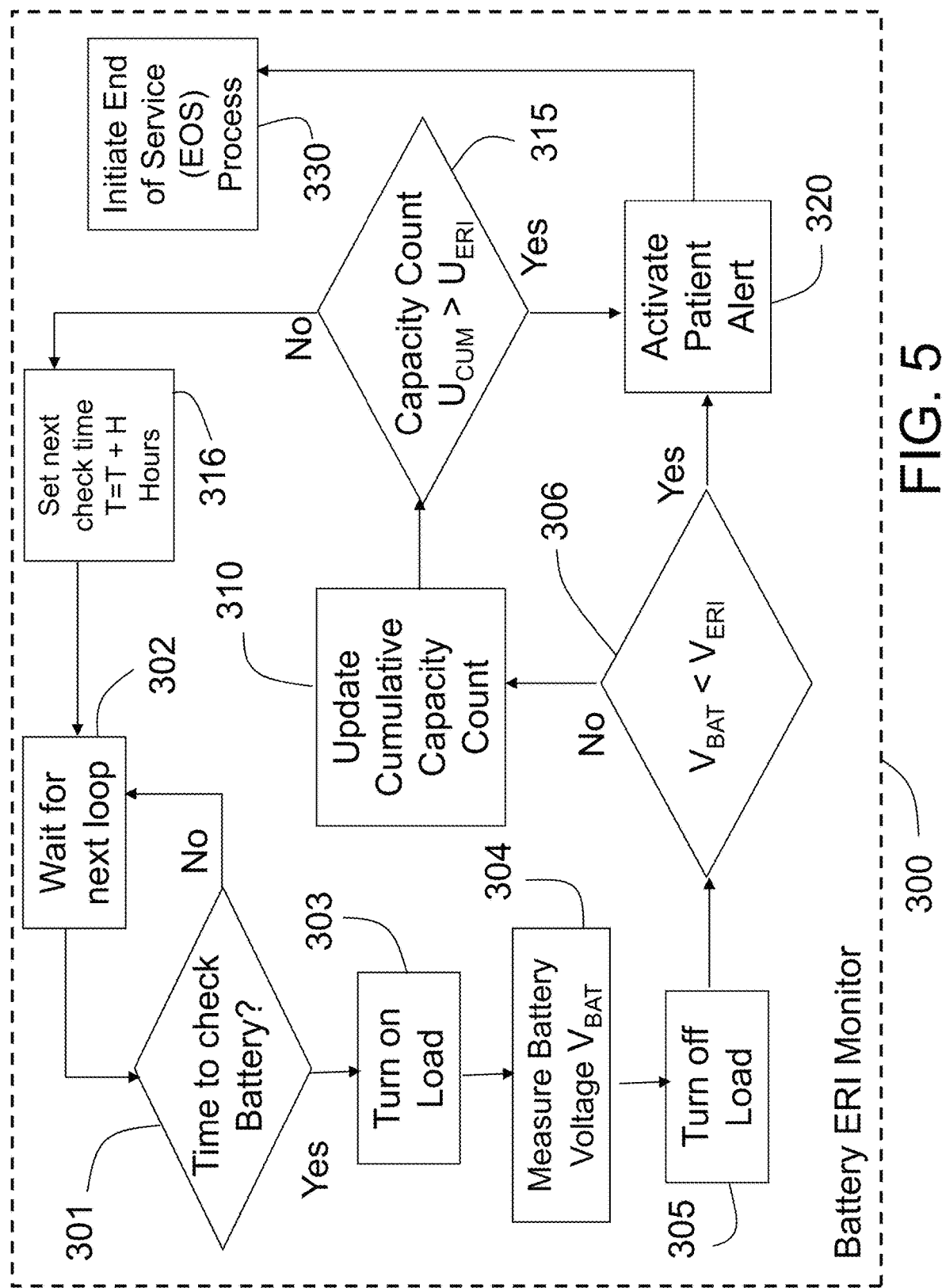
FIG. 5 is a flow chart showing the process for detecting battery Effective Replacement Indicator (ERI) that uses both battery voltage and capacity count methods.

FIG. 5. is a flow chart showing a Battery Effective Replacement Indicator (ERI) process 300 stored in the program memory 45 and run by the IMD CPU 44 of the IMD 10 in FIG. 4 for alerting a patient or remote entity of the need to replace the IMD 10 as it nears end of usable service due to primary battery 22 depletion or other battery performance issue. This process may also be implemented by the SCM 900 of FIG. 3.

In embodiments, the IMD 10 uses two independent strategies to detect battery end of life (EOL) when the battery capacity is completely used up, End of Service, (EOS) when the battery can no longer properly run normal operations including the vibrator and telemetry and determine the appropriate ERI threshold to alert the patient with sufficient remaining capacity to enable selected performance requirements to be met. For example, a threshold can be set to provide at least one additional vibrational alert and remain active for a pre-set interval prior to requiring IMD 10 replacement. Strategy #1 includes operating the battery voltage monitor 23 of FIG. 4 to identify a drop in voltage that occurs when batteries become depleted. Strategy #2 includes providing an "energy use counter", managed by the IMD CPU 44 of FIG. 4, that is based on a defined energy drain value defined for each activity of the IMD 10. For example, the milliamp hours (or microamp hours) for each IMD operation can be measured or otherwise set. Some IMD operations have a defined duration such as data collection and processing of an electrogram segment or providing a vibration alarm. Other operations such as wireless radio use have a known energy use per second or minute. The energy usage is therefore calculated by multiplying the use rate by the duration of the event. If the evaluation of the energy user counter data (e.g., the total or cumulative sum of the values in the energy use counter) meets a criterion then the patient is alerted by the ERI process 300. Alternatively, circuitry that measures actual current usage and duration thereof may be provided.

In an embodiment, the ERI process 300 operates in the primary operating loop within the IMD 10 firmware/software to determine if it is time to check the battery voltage (step 301). If a time amount is not met in step 301, then in step 302 the ERI process 300 waits for the next time to step through the loop. Alternatively, a separate timer or counter (not shown) could provide an interrupt to the IMD CPU 44 of FIG. 4 to run a battery check. The battery check could be incorporated into the code to occur during a periodic update function for baseline data collection, e.g., per hour or per day. Alternatively, checking the battery may be scheduled to occur less frequently such as once per week. Additionally, the interval for checking the battery could be set dynamically, such as once per month, until the battery level is below a selected amount at which time the interval is decreased to a shorter duration such as once per week.

When it is time to check the battery step 303 causes the IMD CPU 44 of the IMD 10 in FIG. 4 to turn on a load so that the battery voltage monitor 23 of FIG. 4 measures the voltage under a known load. Measuring under a fixed and consistent load is important to reduce, to the extent possible, variation in measured values that have nothing to do with the health of the battery. Examples of loads that might be driven by the battery include operating the telemetry sub-system 46, analog to digital (A-D) conversion circuit 41 or the vibrator 25 of FIG. 4. Preferred loads can be obtained by operating the A-D converter 41 during sensing of an electrogram or by activation of the telemetry sub-system 46 or simply switching in a known load. Operating the vibrator 25 for a very short duration (e.g., 10 msec), may also serve as a reasonable load. The battery voltage under load is then measured in step 304 and the load is turned off in step 305 to minimize power use.

In embodiments, obtaining a stable/reliable measurement includes making multiple measurements. For example, 4 sequential measurements might be made. The high and low measurements are discarded and the remaining 2 are averaged to arrive at the functional measurement value. Additionally, the range of the measurements may be calculated. If the variation of the range exceeds a threshold then the IMD initiates an alert to the patient (or sets a flag) indicating that the power supply may be unstable. In one embodiment, to provide some hysteresis, these daily measured values may be exponentially averaged such that the New Value is set equal to: (previous value+current measurement value)/2) to arrive at a value that is used to compare against Effective Replacement Indicator (ERI) or End of Service (EOS) voltage thresholds described in the following sections. Alternatively, the new value can be derived as $((2^n-1)*\text{previous value}+\text{current measurement value})/2^n)$, with "n" set to 4.

Step 306 compares the measured battery voltage $V_{BAT}$ to see if it is below (less than) the pre-set ERI threshold $V_{ERI}$. If the measured battery voltage $V_{BAT}$ is below (less than) $V_{ERI}$ the ERI process 300 moves to step 320 to alert the patient with a See Doctor alert and then proceeds to the EOS process 330 shown in FIG. 8. Step 320 may be delayed so that the alert occurs at a convenient time such as 10 a.m. $V_{ERI}$ is determined during product development and testing to be the battery voltage indicative of sufficient capacity remaining so that not only is there energy to run the vibrator 25 and telemetry sub-system 46 to initiate internal and external patient See Doctor alerts for the need for device replacement but that there will be sufficient capacity left so that the device can remain operational for at least a pre-set period of time while the patient schedules the device replacement with their doctor. In one embodiment, there would also remain sufficient capacity for one additional patient Emergency Alarm if a potential heart attack with excessive ST shifts were to occur during the time between ERI and EOS.

If the measured battery voltage $V_{BAT}$ is not below (less than) $V_{ERI}$, then the ERI process 300 continues to update the cumulative battery usage counter in process step 310, which includes process steps shown in FIG. 7. After updating the cumulative battery usage count in process step 310, the ERI process 300 proceeds to step 315 to check if the device needs replacement due to energy usage even though the battery voltage is still above $V_{ERI}$. This usage determination is based on the cumulative capacity count $U_{CUM}$.

Figure 8:
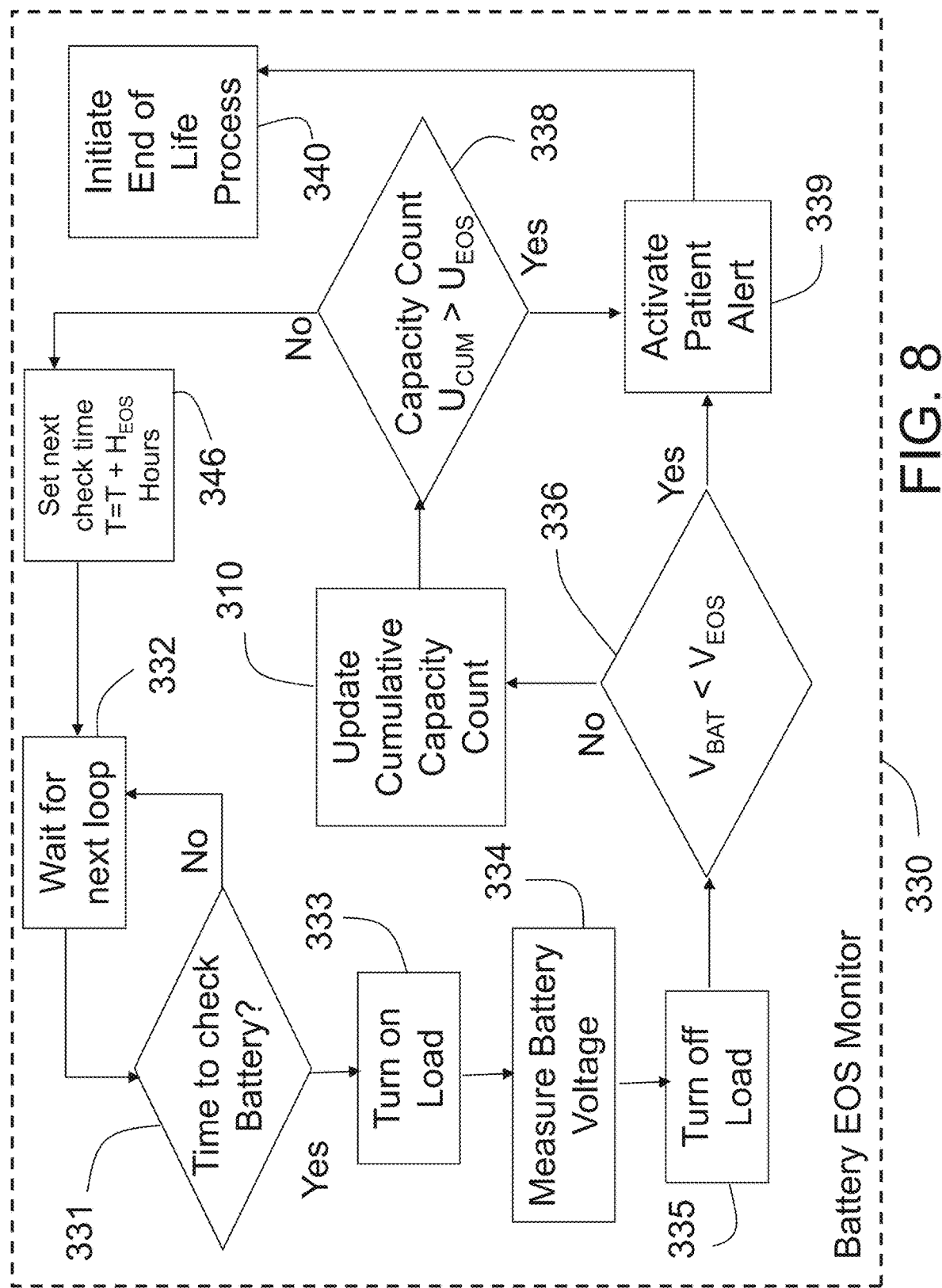
FIG. 8 is a flow chart showing the process implemented at device End of Service.

In step 315 if the updated battery usage cumulative capacity count $U_{CUM}$ is greater than the preset ERI usage count threshold for cumulative battery use $U_{ERI}$ the ERI process 300 proceeds to step 320 to alert the patient with a See Doctor alert, or the step is delayed so that the alert occurs at a selected time of day, and then proceeds to the EOS process 330 shown in FIG. 8. In this embodiment, the (capacity based) ERI threshold $U_{ERI}$ is used to determine when to alert the patient a desired number of days before EOS and optionally to allow at least one Emergency Alarm to occur.

For both voltage based and usage based determinations determined in steps 306 and 315, for example, to be able to claim at least 30 days between ERI and EOS, one might use a threshold of 45 days of typical use for selecting the ERI capacity and/or usage threshold. This embodiment has the advantage in that the patient remains protected by the cardiac monitoring capability during the period between the alert for ERI and the replacement implant.

If the updated battery usage cumulative capacity count $U_{CUM}$ is not greater than the preset battery replacement count threshold for cumulative battery use $U_{ERI}$ the ERI process 300 then proceeds to step 316 where the time for the next battery check T is set to H hours and the ERI process 300 returns to operating within the main loop of the IMD CPU 44 of FIG. 4. In an alternate embodiment, step 316 would reset a timer for the next interrupt-based trigger to the IMD CPU 44 to initiate a battery check.

It is envisioned that, for usage based calculations, H can be a time of between 1 hour and 720 hours (30 days) with the preferred being 24 hours. As other functions of the IMD 10 occur once a day, this allows the timer register T to be used for multiple functions or an existing 24-hour event could be used to trigger the battery checks. It is also possible that the H could be longer during the first few years of service and/or be internally adjusted by the IMD CPU 44 as the voltage measured $V_{BAT}$ decreases or cumulative battery count $U_{CUM}$ increases.

The pre-set values $U_{ERI}$ 482, T 483, and $V_{ERI}$ 481 are stored in the memory 47 of FIG. 4. H and other parameters are stored in the Program Parameters Memory 475 section of the memory 47 of FIG. 4.

While it is envisioned in one embodiment of the present invention that one could use the EOS voltage and capacity thresholds to alert the patient when there is just enough energy for a single patient alert, after which all major function must be turned off in an end of life (EOL) process, it is desirable/necessary to alert the patient several days or weeks before EOS just to be sure there is both enough energy left to sound the alarm and to keep the monitor going until the patient can schedule a replacement implant.

The present invention's unique use of two independent methods to determine when to alert the patient that a replacement is needed (or do other defined operations contingent upon determining a battery status meets a criterion) has the advantage that any method of trying to assess capacity ERI, either by estimation or by actual measurement of battery capacity used, must address the issue of determining a capacity threshold. If the capacity threshold is set too low, batteries with above typical capacity are not used to their fullest extent. On the other hand, if it is set too high, a higher, and potentially a much higher, percentage of batteries will run out of capacity before the ERI capacity is reached. In that case, alerting the patient depends on voltage monitoring described in the ERI process 300 of FIG. 4 which may not be as reliable depending on the type of battery used. This dual method is particularly of value with battery chemistries having steep voltage drops near end of life that could be difficult to catch with a voltage only measurement. Alternatively, only one method may be used and may be selected using the physician's programmer.

Device Energy Usage Characterization Process

Figure 6:
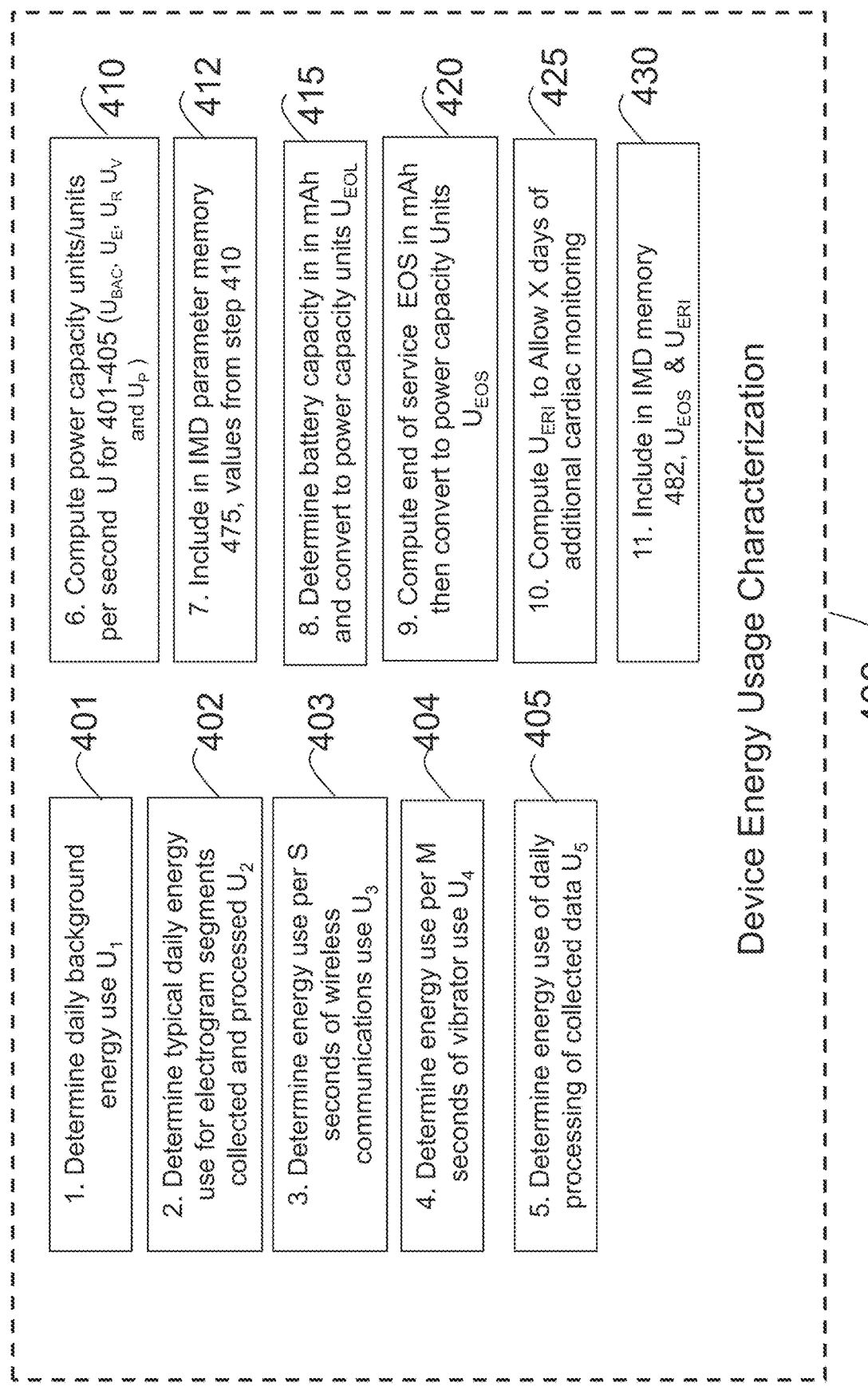
FIG. 6 shows the steps used to determine the End of Service (EOS) and Elective Replacement Indicator (ERI) for battery capacity.

FIG. 6 shows the Device Energy Usage Characterization Process 400, which is a part of the capacity estimation process 330 provided by the IMD 10 to identify battery status such as EOS, the steps of which are shown in FIG. 8. The power management operations illustrated in FIGS. 5, 7, 8 and 9 are carried out under control of the power management module 484 of FIG. 4 in collaboration with the IMD CPU 44. The process 400 is used to determine typical device energy consumption for operational functions, determine battery energy capacity, and compute appropriate battery thresholds such as ERI threshold based on having sufficient capacity remaining to perform defined operations such as providing an alert signal with the vibrator 25 of FIG. 4 and send a signal to the EXD 120 to alert the patient to battery ERI. This may also include the ability to operate the IMD 10 until a replacement can be provided (i.e., before EOS). In a preferred embodiment ERI would allow for at least a selected amount of residual energy as well permit at least one Emergency Alarm to be provided.

In the process 400, completed during device development and testing, one characterizes energy usage of each function of the IMD 10 of FIG. 4 as well as the total energy capacity the primary battery 22 of FIG. 4. The second function includes the need to determine the thresholds $U_{EOS}$ and $U_{ERI}$ 482 stored in memory 47 of FIG. 4.

For the first of these items, the current/energy use (e.g. in microvolts/microwatts) is determined for at least the five functions shown and states: In sub-process 401 the daily background energy consumption $U_1$ when the ACMS/IMD is idle is computed. In sub-process 402 the daily data segment collection energy consumption $U_2$ when electrical heart signal data is collected for a prescribed period and then analyzed including hourly computation for baselines. In sub-process 403 the energy consumption for data communication per time period (e.g., per second) $U_3$ is computed. In sub-process 404 the energy consumption for vibrator operation per time period (e.g., per second or pulse) $U_4$ is computed. In sub-process 405 the daily energy consumption $U_5$ for other processing such as storage of histograms or other processing updated once per day are computed.

While sub-processes 401, 402 and 405 are characterized on a daily use basis, in embodiments a different interval than one day can be used. For example, usage can be characterized hourly, twice a day, every 2 days, weekly or on a monthly basis. Sub-processes 403 and 404 can be characterized per second, per minute, or per hour.

TABLE of
Example Energy use for Various Functions.

| State/function | IMD typical consumption |
|---|---|
| Daily Background consumption ($U_1$) | 251 μA-hr/day |
| Daily consumption for data collection and processing including baselines ($U_2$) | 71 μA-hr/day for the total of 960 daily electrogram segments collected and processed |
| Communications session consumption per second consumption ($U_3$) | 4 μA-hr/second |
| Vibration consumption ($U_4$) | 11 μA-hr/second |
| Daily other processing consumption ($U_5$) | 30 μA-hr/day |

Rather than using microamp hours (μA-hr) to monitor usage, an arbitrary capacity count unit would be more efficient since digital devices work more efficiently when keeping simple counts and avoiding the need to perform large amounts of multiplication and division. As part of the process 400, energy usage in Power Capacity Units (PCU) or PCU per second would be computed from the results of sub-processes 401-405 in sub-process 410.

In an embodiment, the system operates to calculate a group of PCU and PCU/second values, such as $U_{BAC}$, $U_E$, $U_R$ $U_V$ and $U_P$ each in PCU or PCU per second from the values $U_1$, $U_2$, $U_3$ $U_4$ and $U_5$, measured in steps 401-405. Power usage for each operation is initially characterized prior to implant of the IMD 10 or has been previously set in a look-up table due to a prior calibration session. In an embodiment, the measurements of each function occur during device development or in the final verification and validation testing of a manufactured IMD 10. Further, in an embodiment, a preset power capacity unit is determined to be applied to the obtained power usage of each function and may is realized as an arbitrary predetermined number with dimensions of power per time interval (e.g., A-hr per count).

In embodiments: a) the $U_{BAC}$ is defined as the daily background power usage of the IMD 10 in PCU. This is battery power used per day when IMD 10 is not collecting or processing electrogram data, operating the radio or vibrator, or processing other data such as histograms; b) $U_E$ is defined as the daily power usage of the IMD 10 for collecting and processing electrogram segments in PCU. In an embodiment, electrogram segments are collected every 90 seconds and processed to look for abnormalities in the signal and update histograms. Hourly additional processing to calculate baseline data is small but may be added to this; c) $U_V$ is defined as the vibrator 25 use per second in PCU. The daily energy usage from vibration would be $U_V$ times the number of seconds of vibration; d) $U_R$ is defined as the use per second of the telemetry subsystem 46 in PCU. The daily energy usage from radio telemetry would be $U_R$ times the number of seconds of vibration; and, e) $U_P$ is defined as the daily energy usage in PCU for additional periodic processor activity. For example, if the data collection time period is one day for histogram creation, the energy usage in PCU for the once per day processing to save and start new histograms and other such calculations would be included in $U_P$.

In a preferred embodiment, using the values of various functions from a table like that just shown above, the system would convert uA-hrs to PCU resulting in the conversion and daily energy use calculations For example, 36 μA-hrs per power capacity unit might be selected. This would result in: a) daily background energy use $U_{BAC}$ that is 251 μA-hrs converted to 251/36=6.97≈7 PCU; b) daily energy use from electrogram collection and processing $U_E$ that is 71 μA-hrs converted to 71/36=1.97≈2 PCU; c) daily additional processing $U_P$ that is 30 μA-hrs converted to approximately 1 power capacity unit; d) daily energy use for running the vibrator in PCU as determined by multiplying $U_V$, that is 11 uA-hrs per second by the number of seconds of vibrator use $T_V$ and dividing by 36; and, e) daily energy use for running the wireless telemetry radio in PCU would be determined by multiplying $U_R$, that is 11 uA-hrs per second by the number of seconds of vibrator use $T_R$ and dividing by 36.

Accordingly, for a steady state daily use, if no telemetry usage or vibration occurs, would be calculated as 7+2+1=10 PCU. Also, as part of process 400, the PCU for each function would be included in sub-process 412 and stored in the program parameters memory 475 of the memory 47 of FIG. 4.

In an embodiment, the cumulative power usage in PCU $U_{CUM}$ is calculated once per day by the equation $U_{CUM}=U_{CUMPRIOR}+10+T_V*U_V+T_R*U_R$ where $U_{CUMPRIOR}$ is the value of $U_{CUM}$ from the prior day's calculation. For example, if $U_{CUMPRIOR}$ is 6,200 PCU, and there is no vibration or telemetry, $U_{CUM}$ would be 6,210 PCU. Alternatively, if there is no vibration but there is 90 seconds of telemetry, then the daily total would be 10+4*90/36=20 PCU and $U_{CUM}$ would be updated to 6,220 PCU.

With this approach, at any given time in the life of the device, the total power usage in mA-hrs can be obtained by multiplying $U_{CUM}$ by 36 and dividing by 1000. Next, sub-process 415 of process 400 determines (e.g., using a statistical sampling of batteries), the average expected battery capacity in milliampere-hours and converts this to the battery capacity $U_{EOL}$ in PCU.

In this manner, in an embodiment a battery EOS level (where the expected remaining energy can no longer perform all IMD 10 functions) is determined, as computed in sub-process 420, at a pre-set percentage of the total battery capacity. In a preferred embodiment, the value is selected based on the variability of the capacity of batteries. For example, the typical battery capacity may be characterized to be 2,000 mA-hrs, with a 1-sigma of 100 mA-hrs. Thus, the threshold is set a sufficiently low value to assure that virtually all batteries will have at least that much capacity (e.g., using 4 sigma or 1,600 mA-hrs). Alternatively, 1,900 mA-hrs might be selected as the EOS preset threshold and is computed in mA-hrs then converted to PCU to create the EOS capacity threshold $U_{EOS}$ in PCU. For example, 1,900 mA-hrs is 1,900*1,000/36=52,778 PCU. In any case, the threshold should represent a conservative estimate of battery capacity while maintaining a voltage slightly above the input requirement of the voltage regulator circuit to keep the IMD 10 alive.

Next, in sub-process 425 the ERI threshold $U_{ERI}$ is computed in PCU to allow a selected number of days of additional cardiac monitoring (and optionally the addition of providing at least one emergency alarm and data retrieval before EOS). This provides an added safety margin as it can take a month or more for the patient to arrange to get a replacement device. For example, one might like to have 45 days of use before EOS to allow scheduling and completion of IMD device replacement. For example, if the average daily use is 10 PCU and another 50 PCU are needed for an emergency alarm and data retrieval, then to get 45 days one would need 450+50=500 PCU that would produce a $U_{ERI}$ of 52,778-500=52,278 PCU.

Finally, in sub-process 430, the capacity threshold $U_{EOS}$ and $U_{ERI}$ is included memory 482 of the IMD 10 memory 47 of FIG. 4. With 6 months being the typical patient follow-up interval for the ACMS 100 of FIG. 3, alerting for battery EOS is important. This differs from modern day pacemakers which typically upload data on a more frequent basis. In an embodiment, the present invention ACMS 100 is configured to use either or both measured voltage and calculated capacity methods and would alert the patient with a See Doctor alert upon detecting ERI. In an embodiment if action is not taken to replace the device then an additional See Doctor Alert is provided at upon detection of EOS. It should be noted that this scenario assumes normal functioning of the implanted device. Various unlikely fault scenarios can result in the battery being depleted sooner than expected. In such cases, the calculated capacity estimation offers less value. However, voltage measurements will help to provide an advantage of the dual monitoring scheme.

In an embodiment, the ACMS power management module 484 of FIG. 4 is configured to operate according to a power management protocol which assesses both the measured (e.g., VBat) and computed (e.g., $U_{CUM}$) values on a defined schedule (e.g., daily, weekly, monthly, or otherwise). The power management module 484 stores a history of these measured and computed values in a power management log which is stored in memory 47. Additionally, in embodiments, the power management module 484 is configured to operate a processor 44 to display a history of measured and computed values over a selected period such as the prior 180 days and also provide this data to the Physician's Programmer 140 or Smart Device 225, which are configured to display the data in graphical form and/or as summary statistics computed upon the logged values. The power management module of the Physician's Programmer 140 or Smart Device 225 may be provided with an algorithm that plots a trendline as may be fitted to one or more sets of values to provide an anticipated ERI/EOS date based upon at least one of the historical measured or computed values of power usage.

In an embodiment the ACMS 100 would calculate and be able to an estimate of how much more time the device is expected to operate and also display this information if connected to the programmer or if the data is transmitted to a smart device 225 or ESS 240 of FIG. 3. This can be accomplished by the IMD 10 periodically calculating what fraction of the $U_{EOS}$ is the value of $U_{CUM}$ is at and estimating time left to ERI and/or EOS.

In an embodiment, the ACMS the power management module 484 of FIG. 4 is configured to operate according to a power management protocol to extend the remaining power. For example, the ERI process 300 may also entail changing the IMD operations to preserve energy. Low power contingent operations may include, for example, increasing the time between collection of electrogram segments, turning off or adjusting the histogram updating or other data processing not central to event detection, limiting the number of reminder alarms that may be provided, limiting the duration for which an Emergency alarm occurs, setting an alarm to use the EXD alerting first, and using vibration as a second alerting type that only occurs if the user does not respond to the EXD notification, etc. In an embodiment, the Physician's Programmer 140 may permit the doctor to choose "Preserve Power" which causes a set of parameter settings to be adjusted in permitted manners so that device operation is extended (e.g., use the EXD alerting for 2 minutes before initiating the IMD vibration alarm).

Updating Cumulative Capacity Count $U_{CUM}$

Figure 7:
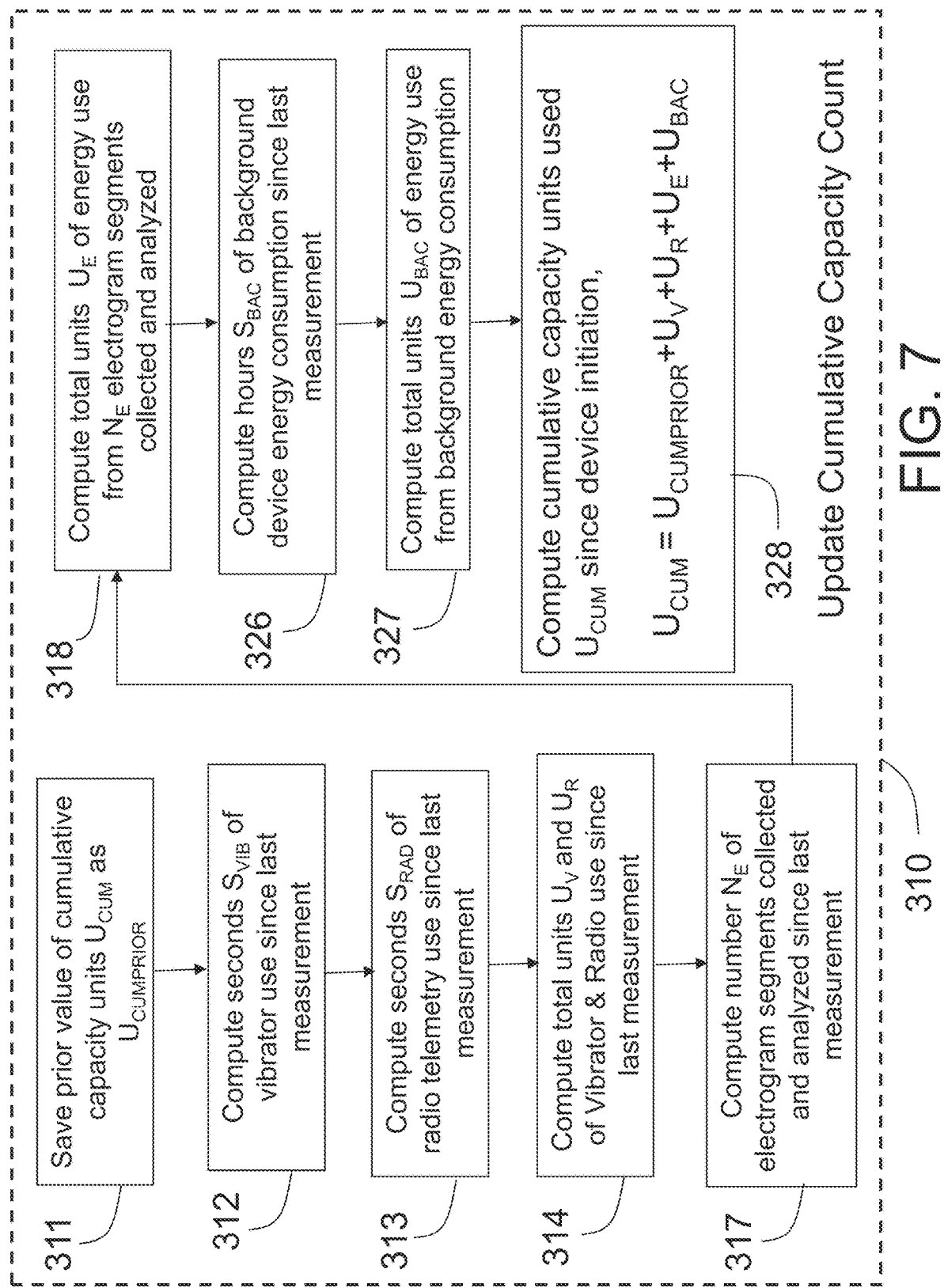
FIG. 7 shows the steps in the process of FIG. 5 for updating the Cumulative Capacity Count $U_{CUM}$.

FIG. 7 is a flow chart showing the detail of the process step 310 of FIG. 5 for updating cumulative capacity count $U_{CUM}$. The process step 310 begins in step 311 where the prior value of $U_{CUM}$ is saved as $U_{CUMPRIOR}$. In steps 312 and 313, the time of use of vibrator and telemetry radio since the last update are computed. In step 314, these are converted into the relative capacity count units $U_V$, $U_R$ and combined into the vibrator/radio use count $U_{VR}$, where $U_{VR}=U_V+U_R$.

In step 312 or 314, the time of use for the vibrator may also be multiplied by a weighting factor which is associated with the strength of the vibration alarm that has been set (e.g. lower strength alarm has a lower weighting factor such as 1, whereas higher alarm strengths set the weight at a higher value such as 1.5). Additionally, the type of alarm or number of bursts in an alarm signal may be associated with a further weighting factor or set of constants that are added to adjust the functional "time of use". In addition to steps 312 and 313, other operations of the IMD 10 of FIGS. 3 and 4 may also be calculated as part of step 327 and added to Ucum in step 328, such as sensing from a glucose sensor. Weighting factors or constants may be used in the Ucum equation to account for operations which may use a different amount of energy per unit time depending upon the characteristic of the performed operation (e.g., Strength).

Next in step 317 the number of electrogram segments collected and analyzed $N_E$ since the last update is computed and in step 318 this usage is converted into relative capacity count units $U_E$. This might also be estimated by multiplying the hourly or daily typical number of segments collected by the number of hours or days since the last update.

Next in step 326, the hours of background device energy consumption since the last update is computed and in step 327 this is converted into relative capacity count units $U_{BAC}$. Steps 317, 318, 326 and 327 can be simplified if the updates are done on a regular basis where the capacity units $U_E$ and $U_{BAC}$ are the same every time and no computing is needed. For example, the ideal update period is once per day when many other functions of the IMD 10 of FIG. 3 are updated.

Finally, in step 328, the updated cumulative capacity unit value $U_{CUM}$ is calculated using the formula $U_{CUM}=U_{CUMPRIOR}+U_{VR}+U_E+U_{BAC}$. $U_{CUM}$ can then be returned to the ERI process 300 of FIG. 5 where it is compared to the ERI value $U_{ERI}$ to see if it is time to notify the patient to seek device replacement.

End of Service (EOS) Monitoring

FIG. 8 shows the steps of an embodiment of an EOS process 330 of FIG. 5 that, in embodiments, is defined to occur after either the voltage or capacity methods for determining ERI has triggered defined operation such as providing a patient or third party with an alert 339. These steps provide a strategy that allows the IMD 10 of FIG. 4 to operate with battery voltage and capacity use being tested and provides an advanced notice so that the device may operate until the patient can get a replacement device or the EOS thresholds are reached which triggers another operation such as the issuance of a final alert before the device goes to the end of life (EOL) process 340.

The process 330 like the ERI process 300 of FIG. 5 operates in the primary operating loop within the firmware/software of the IMD 10 of FIGS. 3 and 4, or occurs as a part of an already scheduled event such as once an hour baseline data collection or once a day creation of new histograms or is invoked after every N-th histogram is created, where N is set to a value such as between 2 and 45. Either way, the process 330 evaluates if it is time to check the battery voltage in step 331, if it is not time it waits for the next time through the loop or for the next scheduled event. This too can also be accomplished by a timer interrupt to the IMD CPU 44 as described for the ERI process 300.

If it is time to check the battery status, then in step 333, the process 330 has the IMD CPU 44 of IMD 10 in FIG. 4 turn on a load so that the battery voltage monitor 23 of FIG. 4 can be measure the voltage under load. The battery voltage under load is then measured in step 334 and the load is turned off in step 335 to minimize power use. In one embodiment, multiple voltage measurements are made and all or some of the measured voltages are averaged together.

Step 336 then compares the measured (or averaged) battery voltage $V_{BAT}$ to see if it is below (less than) the pre-set EOS replacement interval battery voltage threshold $V_{EOS}$. If the measured battery voltage $V_{BAT}$ is below (less than) the VEOS the process 330 proceeds to step 339 to alert the patient with a See Doctor alert and then proceeds to the end-of-life process 340 shown in FIG. 9. $V_{EOS}$ is determined during product development and testing to be the battery voltage above which the device will operate as intended with sufficient capacity remaining to initiate selected functionality such as at least a single patient alert for the need for battery replacement. In other words, at a voltage that is below this level, the electronics of the device may not be powered sufficiently to operate and/or those functions are programmed as disabled.

If the measured battery voltage $V_{BAT}$ is not below (less than) $V_{ERI}$, the process 330 continues update the cumulative battery usage counter in process step 310. Details of process step 310 are shown in FIG. 7. After updating the cumulative battery usage count in process step 310, the process 330 proceeds to step 338 to check if the device is in need of replacement based on the battery capacity count.

Figure 9:
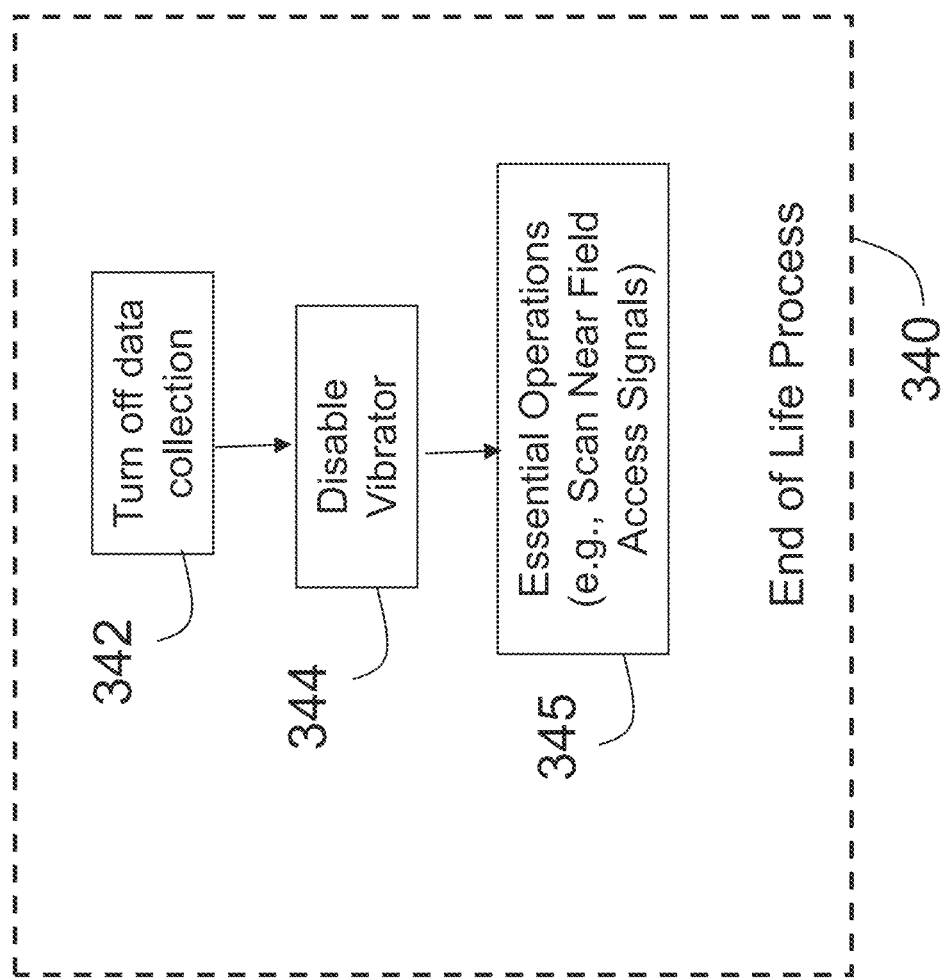
FIG. 9 is a flow chart showing the process implemented at device End of Life.

In step 338 if the updated battery usage cumulative capacity count $U_{CUM}$ is greater than the preset EOS usage count threshold for cumulative battery use $U_{EOS}$ the process 330 proceeds to step 339 to alert the patient with a See Doctor alert and then proceeds to the end-of-life process 340 shown in FIG. 9.

If the updated battery usage cumulative capacity count $U_{CUM}$ is not greater than the preset battery replacement count threshold for cumulative battery use $U_{EOS}$ the process 330 then proceeds to step 346 where the time for next battery check T is set to $H_E$OS hours and the process 330 returns to operating within the main loop of the IMD CPU 44 of FIG. 4 or being triggered by a scheduled event or clock interrupt.

It is envisioned that $H_E$OS can be a time of between 1 hour and 320 hours (1 month) with the preferred being 24 hours. As other functions of the IMD 10 occur once a day, this allows the timer register T to be used for multiple functions.

The pre-set values $U_{EOS}$, $V_{EOS}$, $H_E$OS and other parameters or stored in the Programmer Parameters Memory 475 section of the memory 47 of FIG. 4.

Device End of Life and Recharge-Necessary Processes

FIG. 9 shows an example embodiment of an end-of-life (EOL) process 340 that is implemented once there is no longer sufficient energy in the device for it to be guaranteed to operate properly (and/or the operations are set to be disabled). For example, this may be an energy level the remains that is insufficient for the battery to power the vibration alarm and provide any additional patient alerts. The EOL process is put in place so that there is hopefully sufficient energy remaining for a final communication session with the ACMS Physician's Programmer 140 of FIG. 3.

EOL process 340 begins by discontinuing all data collection in step 342, disabling the vibrator 25 of FIG. 4 in step 344 so it cannot be turned on (or setting a flag in the IMD processor 44 of FIG. 4 so that vibration alerting commands are ignored or the vibration strength is set to zero, etc.). A final step 345 is to minimize all power use that is not essential. Essential power operations may include providing power to clock or timer or periodically scanning for communication requests by checking a near-field signal sensor 90 with antenna/coil 91 of FIG. 4.

Using a dual method of assessing remaining power, as described herein, is likely to be the best way to provide a user with sufficient notice of the onset of EOS, and to prevent the EOL occurring without a user being notified sufficiently in advance.

In embodiments, a rechargeable battery is used by a component of the system such as the IMD 10 of FIG. 3. In this instance, the ERI indicator can be used as a proxy for a Recharge-Necessary Indicator (RNI). In FIG. 8, step 340 triggers an RNI process rather than an EOL process. The RNI level may be set to provide residual capacity such as a level of remaining power that allows a minimal duration (e.g., two days) of operating power or allows the provision of minimal operations such as two additional Emergency alarms. Additionally, the RNI process may cause the system to operate so that it will only issue Emergency alarms or See Doctor alarms or both via the EXD 120 to conserve power (or the EXD may provide an alarm first and then the vibration alarm occurs only if that does not lead to an Alarm Silence button push by a patient). The RNI alert may be defined for the IMD 10/EXD 120 or both, and an RNI log may be created. The RNI log can be used to determine patient compliance with respect to recharging the IMD without allowing the power to fall below a level that is sufficient to provide continued operation.

Primary and Reminder Alarm Protocols

Figure 10:
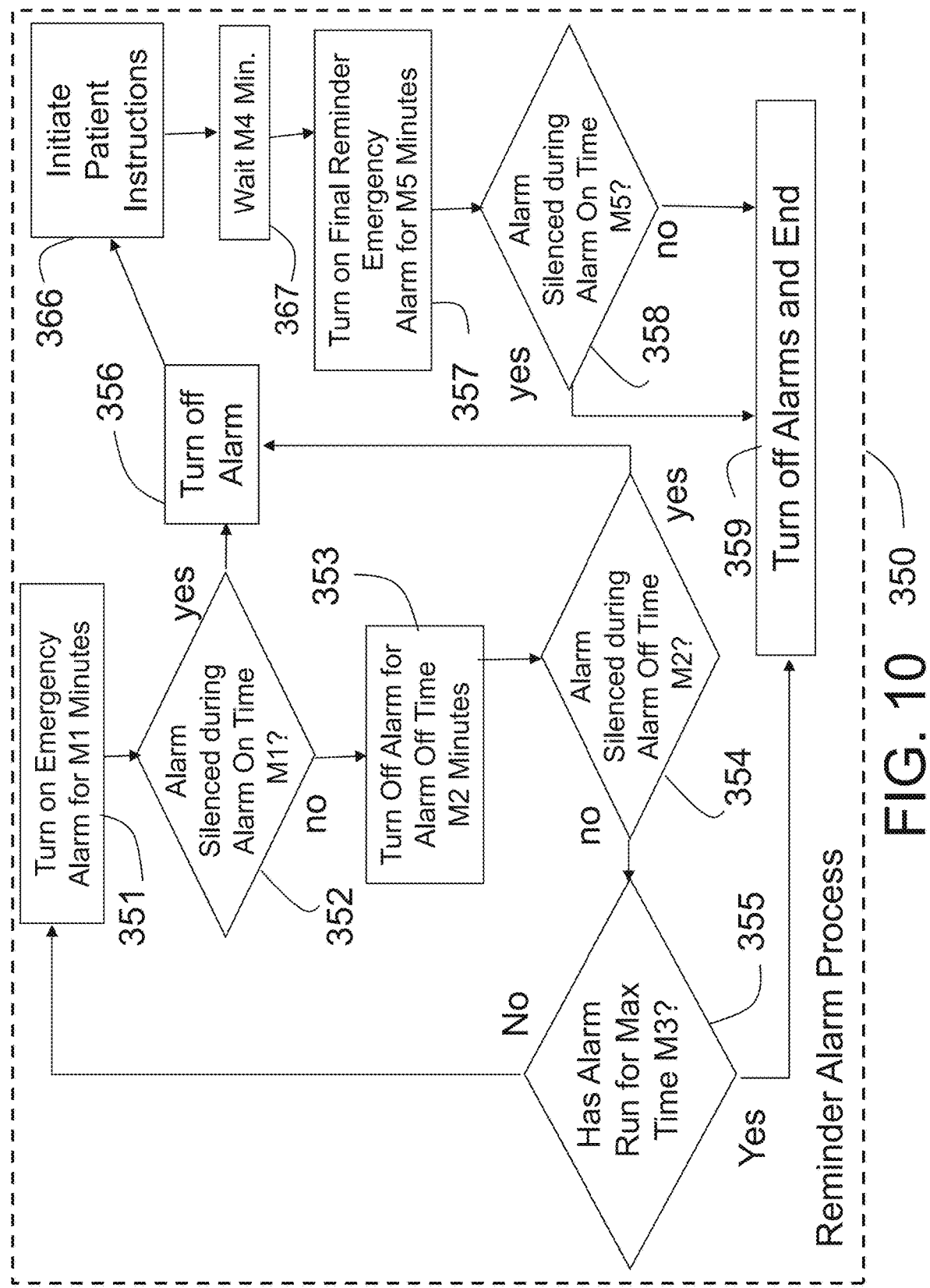
FIG. 10 is a flow chart showing the process for providing reminder alarms.

FIG. 10. is a flow chart showing an example embodiment of a process 350 for providing a primary or first alarm such as an Emergency Alarm and then secondary or "reminder" alarms. In the shown embodiment, a reminder alarm is provided if the patient silences the alarm or fails to do so. The process 350 is defined in the program memory 45 of the IMD CPU 44 of FIG. 4 of the IMD 10, SSMD 800 or SCM 900 of FIG. 3, as a set of instructions for 1 or more alarm protocols and is carried out under control of the CPU 44.

In embodiments, the ACMS may include reminders or notifications defined for alerting the patient which are related to an alert, due to a time of day or tied to an event. Reminders can be provided by the IMD 10, EXD 120 SSMD 800 or SCM 900, or through a message or notification to the smart device 225 of FIG. 3. Reminders can be a text message and/or spoken message. Examples include: 1. Reminders to take medications including: a) a reminder to chew an aspirin or consume medication after an Emergency Alarm; and, b) A non-compliance notification suggesting that the patient may have skipped their beta blocker medications following alerts for High or extended Elevated heart rate; 2. A reminder to perform a task due to a patient notification (e.g., 2 or 3 days after a See Doctor alert has occurred the patient is reminded that a doctor appointment should have been scheduled); and 3. reminders to perform daily exercise or other behaviors that promote good heart health.

In embodiments, the ACMS 10 of FIG. 3 detects the occurrence of an event defined as requiring notification. The ACMS 10 provides a first alarm to notify the patient. If defined for the event, then at least one additional reminder alarm is provided at a preset delay after either a) the initial alarm or b) the patient acknowledgment/silencing of the initial alarm using the EXD 120. The attributes for the reminder alarm are defined as a function of the alerted event type and may be provided by the EXD 120, the IMD 10, and/or other ACMS 100 system component. If the EXD 120 provides the reminder alarm, then the EXD 120 can be programmed to provide this without requiring the IMD 10 to send another alert trigger to the EXD 120 (to save power). Further, reminder alarms can be defined contingently. For example, if a patient does not silence the initial alarm, then the reminder alarm can occur after a shorter amount of time and at a louder intensity (than the initial alarm or than an alarm that occurs after patient confirmation). Reminder alarms can also be silenced by for example, the alarm silence button 122 of the EXD 120 of FIG. 3. It is important to recognize the value of patient acknowledgement of alarms in the long-term management of high-risk patients in a home or ambulatory environment. While the prior art describes reminders if the patient does not acknowledge/silence the alarm, reminder alarms are also useful in situations such as when a subject silences the initial alarm that wakes them from sleep, while decreasing the risk of falling back asleep without taking action. Accordingly, even when an alarm silence button is pressed, providing at least one additional reminder alarm provides an advantage. Additionally, the EXD 120 is provided with an alarm module that is configurable by the patient or doctor to increase the number of reminder alarms that will occur in addition to the first alarm. Further, when a bedside monitor or an EXD 120 is provided which communicates with a remote center, then a remote telemedicine session may be defined to occur as part of the reminder alarm.

In embodiments, a device of the ACMS 100 (e.g., IMD 10, SSDM 800 or SCM 900 of FIG. 3) detects the occurrence of an event that has been defined as requiring a reminder notification be provided to a user such as the patient. In this example, the ACMS 100 provides a first alarm to notify the patient 351. If defined for the event, then at least one additional reminder alarm is provided at a preset delay. The reminder alarm is provided after either a) the initial alarm or b) the patient acknowledgment/silencing of the initial alarm (e.g., using the EXD 120 of FIG. 3). The attributes for providing the reminder alarm are defined for the type of alarm that was provided and/or for the alerted event type. The reminder alarm may be provided by the EXD 120, the IMD 10, SSMD 800 or SCM 900, and/or other ACMS 100 system component such as a smart device 225.

Reminder alarms can also be silenced or may simply stop after an interval. Patient acknowledgement of alarms, and tracking of such acknowledgement in an EXD log, is useful in assessing compliance in the long-term management of high-risk patients in a home or ambulatory environment. Additionally, the EXD 120 is provided with an alarm module managed by the EXD CPU 130 of FIG. 3 that is configurable by the patient or doctor to adjust the characteristics of alarms such as to increase the number of reminder alarms that will occur in addition to the first alarm. When the EXD 120 or a smart device 225 of FIG. 3 operates with a home base station that can communicate with a remote center 240, then a remote telemedicine session may be also defined to launch as part of the reminder alarm.

In FIG. 10, the reminder alarm process 350 begins after an Emergency Alarm is initiated in step 351 for an Alarm On period of M1 minutes. The Emergency Alarm may be defined to alert the patient in a pattern of bursts of vibrational pulses from the IMD 10 and/or acoustic and visual alerts from the EXD 120 of FIG. 3.

Next, in step 352 in a preferred embodiment if a near field signal is received by the near field signal sensor 90 then an interrupt is sent to the CPU 44 (or in in alternative "polling" embodiment, the near-field signal sensor 90 is checked periodically by the IMD CPU 44 of the IMD 10 of FIG. 4 during an Alarm On interval to determine if the EXD 120 of FIG. 3 has been placed in the near-field and/or the near-field signaling system 133 has been activated by the user pressing the alarm silence button 122). If no button press has been detected, alerting will be turned off for the Alarm Off period of M2 minutes in step 353. In step 354 in a preferred embodiment when a near field signal is received by the near field signal sensor 90 then it would send an interrupt to the CPU 44 (or in a polling embodiment, the CPU 44 will continue to monitor for the occurrence of an alarm silence signal to be transmitted from the EXD 120 during the M2 period which would indicate the user had pressed the alarm silence button 122).

If the Alarm silence signal is provided during either Step 352 or 354 the process 350 will turn off the alarm signal in step 356 (or set a flag to indicate that the Alarm has been responded to and is functionally completed). In step 366 additional instructions (e.g., an auditory message to call 911) may be provided to the patient (by the EXD 120 or other system component) before waiting a duration of M4 minutes in step 367. The process then initiates a Final Reminder Emergency Alarm in step 357 that occurs for a defined Alarm On duration of M5 minutes. If the Final Reminder Emergency Alarm provided in step 357 is either assessed as silenced by a user during the M5 minutes 358 or continues for the entire M5 minute duration, then the alarm signals will be disabled in step 359, and the process 350 will terminate in step 359.

Alternatively, if the alarm is not silenced by a user in either step 352 or step 354, then step 355 will check if the maximum duration M3 for an unsilenced emergency alarm has been met or exceeded. If the M3 duration has not been met or exceeded, then the process 355 will return to step 351 and activate the Emergency Alarm for a duration of M1 minutes. If the maximum duration has been met or exceeded, then the process will terminate in step 359.

In embodiments, if only the EXD 120 provides a reminder alarm then the processor of the EXD 120 can operate software which is programmed to provide one or more reminder alarms without requiring the IMD 10 to send another alert trigger to the EXD 120 (to save power). Further, reminder alarms can be defined to occur contingently by software operated by the processor of the EXD 120. For example, if a patient does not silence the initial alarm then the reminder alarm be defined to occur after a shorter duration and at a louder intensity than the initial alarm.

There are a wide range of possible patient information such as patient instructions or guidelines that can be provided by step 366. This information can be related to one or more of the following actions: 1) Taking or injecting one or more medications prescribed or suggested by the patient's doctor—for example chewing an aspirin can have a significant benefit during a coronary occlusion caused by a blood clot; 2) Calling a phone number to speak to a medical professional or caregiver; 3) Performing a physical action, for example, lying down or raising one's legs above one's body.

The patient information may be provided by one of the following: 1) by the EXD 120 through incorporation of voice announcement or a text display; 2) through a verbal or text message sent to the patient's or caregiver's home base station, tablet or smartphone using standard messaging techniques and/or using the SDAPP 220 of FIG. 3, and/or; 3) by a phone call to the patient or care giver with an announcement placed to a voice telephone; or 4) by a skype, zoom, facetime or other video call placed to the patient's smart device 225 that may be also incorporated into the SDAPP 220.

Examples of M1, M2, M3, M4 and M5 are as follows: M1 might be between 5 seconds and 30 minutes; M2 might be between 30 seconds and 30 minutes; M3 might be between 5 minutes and 24 hours; M4 might be between 5 minutes and 1 hour; M5 might be between 15 seconds and 30 minutes.

In embodiments, the Emergency Alarm is realized using an international standard for Emergency signals which comprises of 5 pulses repeated in pattern of 3-2 for an M1 period of (e.g., 3-5 minutes), then off for an M2 period (e.g., 10 to 15 or 20 minutes). In embodiments, this alarm protocol can be continued for an M3 period, for example, 2 hours. If silenced during the M3 period, the process 350 could wait an M4 period, such as 15 minutes, then reactivate the Emergency Alarm for an M5 duration of 30 seconds unless silenced.

In an embodiment of the ACMS 100, reminder alarms are used to provide a higher level of alerting if the initial alarm is not acknowledged/silenced by the patient relative to that which is provided if it is acknowledged/silenced. A higher level of alerting may include one or more of the following: a larger number of reminder alarms; higher amplitude/intensity for reminder alarms; a shorter interval between reminder alarms; and, a different pattern for the reminder alarm.

Histogram Generation, Storage and Display.

Figure 11:
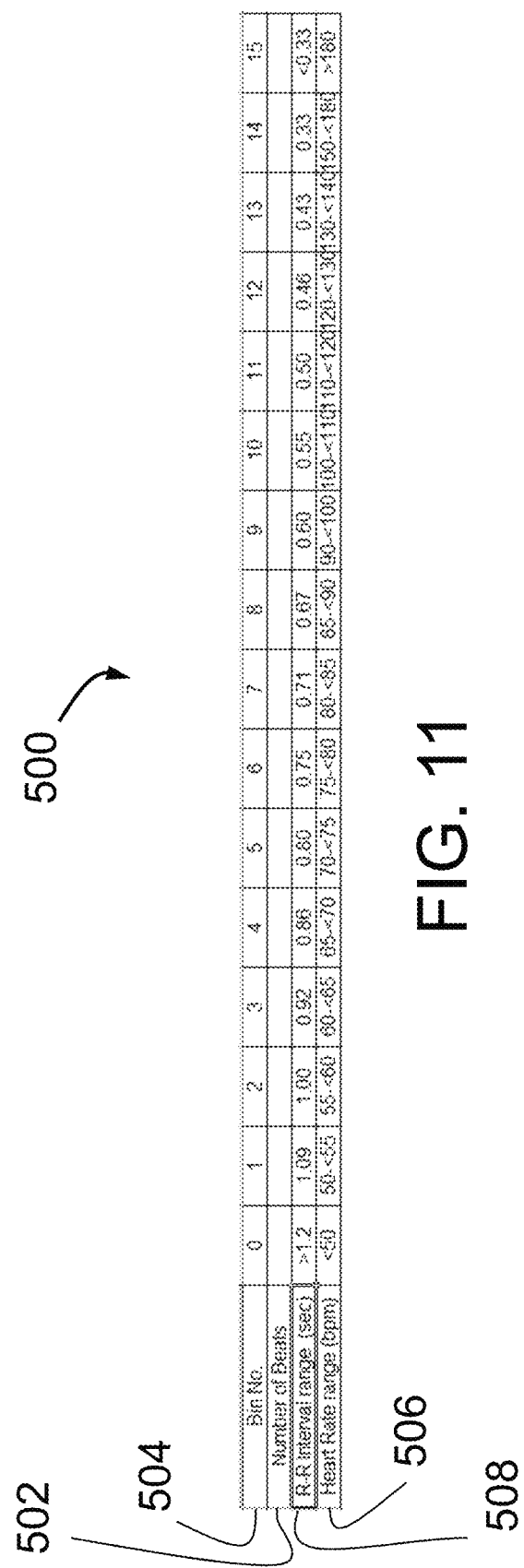
FIG. 11 is a table showing the structure of the R-R interval/heart rate histogram data memory for a single data collection interval.

FIG. 11 is a table 500 showing the structure of a portion of an R-R interval and heart rate histogram data memory 473 of FIG. 4 for a single data collection interval. The term "data collection interval" is defined as the time during which the IMD 10, SCM 900 or SSMD 800 of FIG. 3 updates a specific histogram. The data collection interval could be as short as a minute and as long as many months. Additionally, several data collection intervals may be used and related to each other. For example, daily histograms can be used to generate weekly histograms or monthly histograms. In a preferred embodiment tracking a patient's daily heart rate profile, an hourly data collection interval is used to provide 24 histograms per day. That is a small amount of data. For example, the histogram table 500 of FIG. 11 has 16 bins that at two bytes of data per bin needing only 32 bytes per histogram or 24×32=768 bytes per day, 23K bytes per month and 276K bytes per year. This is an efficient way to store this data and 2 bytes of data per bin will allow counts of up to ~65 thousand.

In embodiments, the ACMS capabilities and features include the use of histograms to efficiently store and analyze data to derive and display the distribution of ST-shift levels (or other ST-segment measure) as disclosed in U.S. Pat. Nos. 7,512,438, 8,024,028, 8,244,430 and 9,005,130.

In an embodiment, R-R interval/heart rate histograms are stored in the R-R interval Histogram memory 473 of the IMD 10. This heart rate tracking capability using histograms is a desirable feature in addition to the ability of the IMD 10 to detect acute heart rate abnormality events such as High, Low and Irregular heart rates described in the prior art.

As an example, the histogram table 500 of FIG. 11 has 4 rows, the bin number 504 in row 1, the values for the number of beats 502 for a particular bin in row 2, the heart rate range 506 in row 4 and the corresponding RR interval range maximum 508 in row 3. Only the actual number of beats data is stored in the R-R interval histogram memory 473 while the ranges are preset (for all patients or can be specific to each patient) in the program parameters memory 475 of FIG. 4.

Histogram data can be combined to evaluate or present views of heart rate/R-R distributions over days, weeks, months or years as a feature of the Physician's Programmer 140 and SDAPP 220 of FIG. 3 to select how and which data is combined to best help a clinician understand changes over time and provide insights as to what is going on in a patient's heart.

Figure 12:
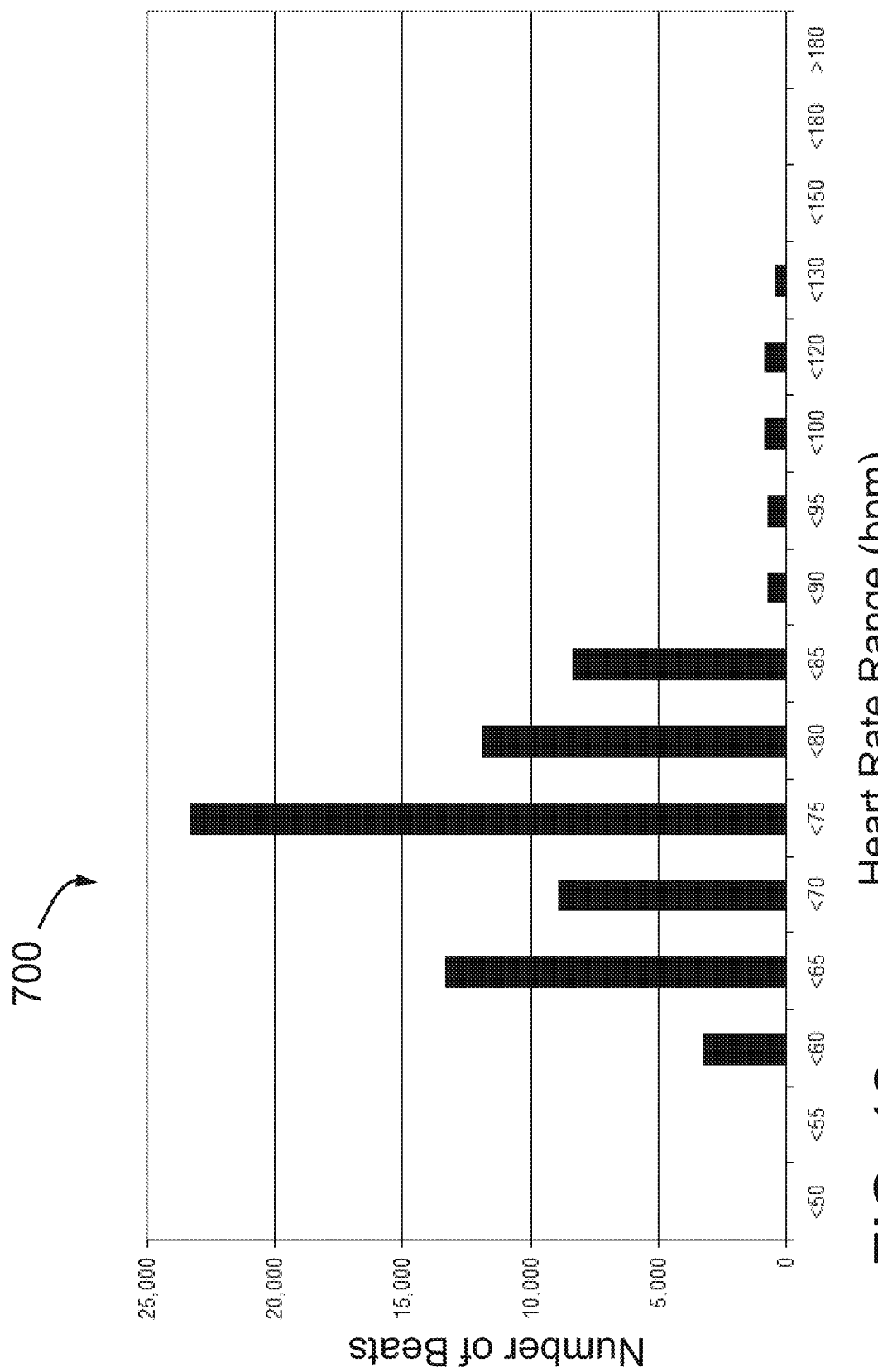
FIG. 12 is an example of the plot of the R-R interval histogram data for a day.

FIG. 12 is an example of the present invention display screen implemented on the Physician's Programmer 140 or the SDAPP 220 of FIG. 3 showing a two-dimensional histogram plot 700 of heart rate captured over an interval such as a week. In embodiments a histogram plot is the result of combining a week's worth of hourly histograms. This information may help a medical professional identify anomalies over longer periods of time of weeks, months or more. For example, a new incidence of many beats below 50 bpm could indicate need for a pacemaker. A new incidence of beats above 160 bpm could indicate the need for an anti-tachycardia therapy. If no beats are above 90 bpm for a week, then a patient may need to be encouraged to exercise. A selected number or percentage of beats with R-R intervals corresponding to an elevated heart rate range (e.g., between 100 and 150 BPM, or otherwise set by a user or device algorithm) could indicate a compliance issue or need for a dose change of the patient's beta blocker prescription.

Furthermore, the IMD 10 of FIGS. 3 and 4 can process histogram data to compute extracted histogram data including statistical data such as: 1) the median, mean, maximum and minimum heart rate or R-R interval for each histogram; 2) the standard deviation of the histogram distribution with respect to the highest value bin or with respect to the mean or median; 3) the number of beats per hour, day, week or month per histogram exceeding a pre-specified threshold of R-R Interval or heart rate; 4) The moving average over two or more data collection time periods of any of items 1 through 3.

In embodiments, extracted histogram data is compared by the IMD 10 with a pre-set or machine learned detection threshold for ST-segment ischemia detection or other cardiac measure. If a threshold is exceeded for a selected number of segments or time period, the IMD 10 can perform operations including: alerting the patient by means of a See Doctor Alert or Emergency Alarm; transmitting the event and/or associated data through the EXD 120 to an External Support System (ESS) 240 for storing of historical records or later clinician review; transmitting the event and/or associated data through the EXD 120 to a medical practitioner or care-giver who would have access through the SDAPP 220.

Histogram data, summary statistics, and extracted histogram data and other data in the IMD 10 may be uploaded to the ESS 240 through the EXD 120 on a periodic basis. The EXD 120 is programmed to continuously or periodically operate its communication circuitry to receive signals if they are transmitted from the IMD 10 which is programmed to turn on its telemetry sub-system 46 and connect through the EXD 120 to transmit through the voice/data network 250 to the ESS 240.

In embodiments, the IMD 10 processor is configured to compare changes in extracted histogram data between two time periods to detect a change that is defined to trigger any of the above operations. Changes can be evaluated using one or more comparison thresholds which are used to evaluate the comparison of one or more features of a histogram or features calculated therefrom. For example, shape of the histogram can be compared using a "broadness", skewness, asymmetry above and below the median, or other variance measure of two histograms, and the difference in the measures are compared in relation to threshold values.

The Physician's Programmer 140 of FIG. 3 allows for visualization, adjusting, and programing to define or select one or more heart signal parameters that will be tracked using the histogram technique. It is also envisioned that the Physician's Programmer 140 can process the histogram data downloaded from the patient's IMD 10 of FIGS. 3 and 4 and operate upon these data to derive detection thresholds that are suggested or set to enable event detection by the IMD 10. The events that are detected may be cardiac events that either are occurring or can be future cardiac events that warrant patient notification or other operations.

In an embodiment, populating the histogram 700 of FIG. 12 is accomplished as follows:
1. The IMD 10 of FIG. 4 will capture an electrogram segment N seconds long every M seconds (or minutes) and measure the R-R intervals for each beat. For example, a sensing protocol which senses a 10 second electrogram data segment every 90 seconds is established.
2. A new histogram with B bins is created every K minutes and the prior histogram saved for a preset data retention time period (which can be very long since the memory use of these histograms is small).

For the new histogram each time a beat with an R-R interval occurs over the K minutes the IMD CPU 44 of FIG. 4 will increment by one (1) the value in the histogram bin corresponding to the R-R interval range associated with the measured R-R interval of the electrogram segment. The bins may alternately correspond to a heart rate range with associated R-R interval range.

For example, FIG. 11 shows a table 500 representative of a histogram with 16 bins (0-15) in line 504 with 16 R-R interval ranges 508 with corresponding heart rate ranges 506. As mentioned in the prior example, a histogram table such as this might be created every 60 minutes (i.e., K=60).

Tracking a patient's heart rate over days, months or years can be of great value in reflecting heart function status or change in status, and for diagnosing heart rate anomalies such as arrhythmias or issues with beta blocker compliance or dosing.

In embodiments, similar histograms are used to track heart signal parameters including, for example, at least one of the following: 1. ST segment voltage 2. ST deviation (ST segment amplitude minus PQ segment amplitude for a single heartbeat), 3. R-R interval (interval between successive R waves), 4. R-R interval variability, 5. R peak height, 6. R wave width 7. QRS voltage, 8. QRS width, 9. RS width, 10. T wave width and/or amplitude, 11. T wave *alternans*, and 12. ST-shift or ST-Shift % may also be tracked. QRS shift (a recent average value of QRS voltage over a data collection time period minus the baseline QRS voltage. In an embodiment, the baseline QRS voltage is the average value of the QRS voltage for a multiplicity of heart beats at a time when the heart of a heart transplant patient is not undergoing rejection. A measure of "heartbeat size" may be used to normalize a measure such as ST-shift, which may be R peak height, but may also be the measure of the highest peak of recorded heartbeats or other measure which reflects the overall size, or selected component or portion, of the recorded heartbeats.

Figure 13:
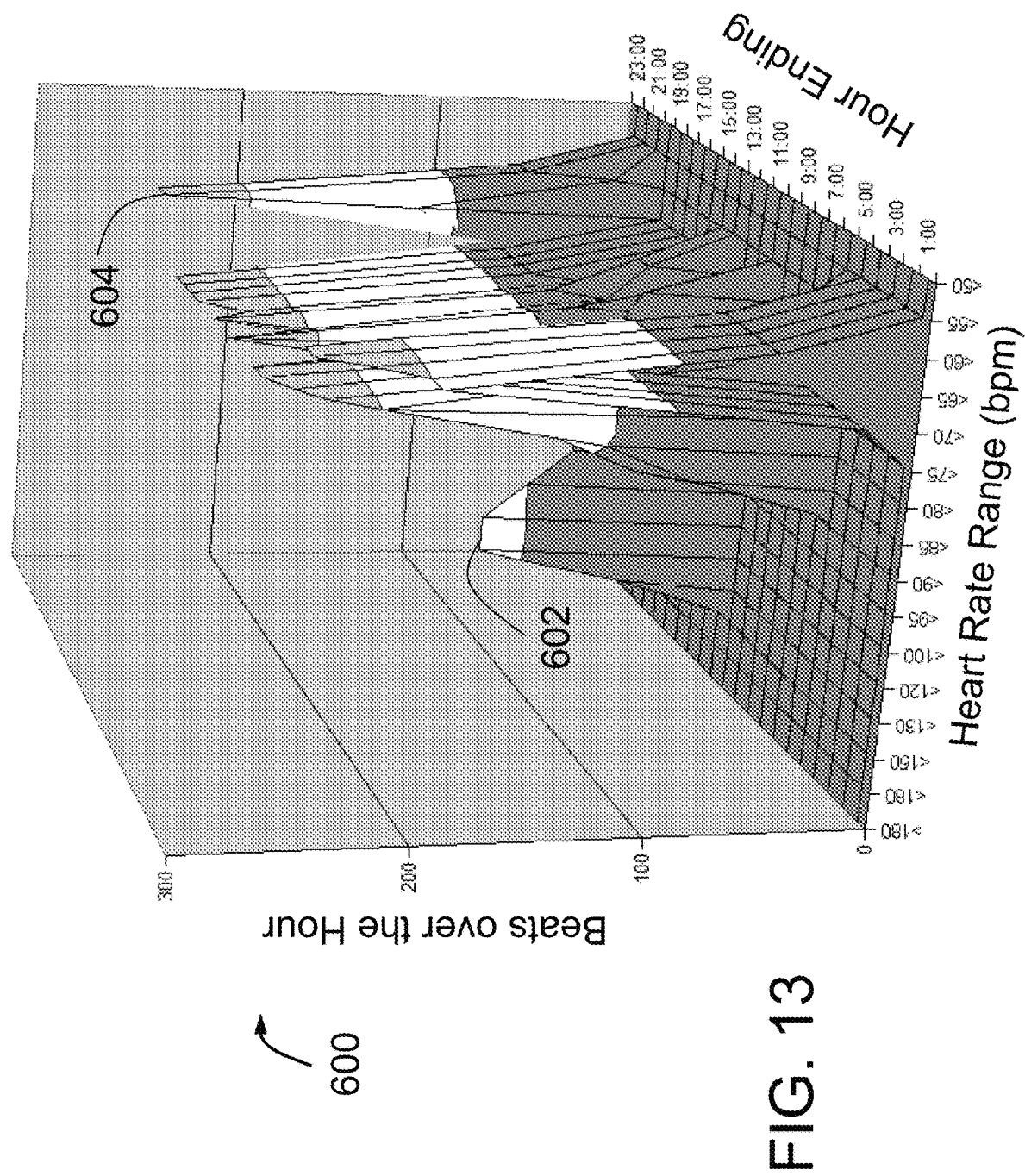
FIG. 13 is an example from a present invention display screen implemented on the programmer of FIG. 3 showing a waterfall plot of the R-R interval data for a patient with 1 hour data collection time intervals.

The present invention IMD 10 of FIGS. 3 and 4 analyzes processed heart signal parameter data including that stored as histograms and statistical data extracted from the heart signal parameters and statistical data extracted from the histograms to identify changes in cardiovascular condition over time periods of days, weeks, months or even years. The statistical data is valuable for identifying cardiac events, for example such as detecting when a median heart rate exceeds a 100-bpm value for a number of hours. The histogram data can also be displayed for human analysis by the patient's physician using analysis tools provided in the ACMS Physician's Programmer 140 or the SDAPP 220 of FIG. 3. Such displays can be for individual or combined histograms such as that shown in FIG. 12 or a surface plot such as shown in FIG. 13.

As will be disclosed in greater detail later in this application, to detect potential ACS events accurately, positive and negative excessive ST shift thresholds must be established to assess ST data. Returning to FIGS. 3 and 4, an exemplary embodiment of a system for alerting patients to a potential heart attack by identification of excessive ST shift from the heart signal of a patient is shown. As seen in FIG. 3, a pair of electrodes 112, 115 are connected to an IMD 10 containing a vibrator 25 or some other alerting mechanism. Electronics within the IMD 10 are electrically coupled to the electrodes 112, 115. The IMD 10 contains a processor 44 with associated digital memory adapted to compute the values of the ST deviation, ST shift and ST Shift %. In an embodiment, that average heart signal amplitude would be calculated from all or a portion of the same heart signal data used to calculate the baseline average ST deviation.

The processor 44 is adapted to save in memory the values of ST deviation for a pre-set data collection time period. The collected data provides the distribution of ST deviation over the data collection time period. The ST deviation distribution has a mean, a median, a positive (values greater than zero) portion and a negative (values less than zero) portion. In a preferred embodiment, the values of ST deviation are stored as histograms in units associated with the values produced by the Analog-Digital Converter 41 of FIG. 4 and which may be referred to as "ADC units". Histogram data is stored in the ST histogram memory 472 of the IMD 10 of FIG. 4. At least one new histogram is created for each data collection time period, such as 1 day. In a preferred embodiment, a set of 14 histograms are stored for a data retention time period of 2-weeks.

In an embodiment a new histogram is created for each of a multiplicity of heart rate ranges for each data collection time period. Histograms are retained in the memory 472 for a data retention time period. In an embodiment, there are 5 heart rate ranges, the data collection time period is a day and the data retention time period is 14 days. This would then require at least 70 (14×5) total histograms, although in a preferred embodiment one would have 75 so that the new one is being populated before the one from 14 days ago is available for new incoming data.

Also stored in the ST histogram memory 472 are values of an average heart signal amplitude for a data retention time period associated with a histogram or set of histograms. The average heart signal amplitude is used in normalization of ST deviation to compensate for changes over time that can occur due to, for example, lead impedance variation of the lead-tissue interface, and other changes that can affect the amplitude of the measured heart signal. In a preferred embodiment, the average signal amplitude is measured and stored in ADC units.

In an embodiment, a positive ST deviation has the average value of the ST segment voltage in ADC units being greater than the average value of the PQ segment voltage in ADC units (or other proxy for isoelectric level). A negative ST deviation has the average value of the ST segment voltage in ADC units being less than the average value of the PQ segment voltage in ADC units. The description of FIGS. 18-21 further describes a process used to calculate positive and negative detection thresholds for excessive ST shift measures derived from ST deviation histograms. The average heart signal amplitudes are used to normalize the ST deviation levels that in a preferred embodiment will create positive and negative excessive ST shift thresholds stored as a percent of the average heart signal amplitude (e.g., "ST shift %"). The calculation of the thresholds can be programmed to occur in the IMD 10 but is typically accomplished using uploaded data in the Programmer with visual review and confirmation or adjustment by a doctor or trained technician prior to downloading the parameter values to the IMD.

Techniques to capture electrogram data and heart signal parameter data computed from electrogram segments over days, weeks or months are important because, some of the processes of heart malfunction are gradual. It is desirable to detect and treat such conditions before the onset of an acute event such as an AMI, heart failure onset, ventricular ejection fraction decrement, or ventricular fibrillation or the complete rejection of a transplanted heart. Use of histograms helps to limit the amount of memory and electrical power needed in the IMD 10, SSMD 800 or SCM 900 of FIGS. 3 and 4, to collect, store and analyze the heart signal data looking for trends is especially important in implantable and portable systems.

Stress Test Mode.

In an embodiment, the patient can press a button (not shown) on the EXD 120 of FIG. 3 labeled "stress test" before pursuing a period of exercise and the IMD 10 of FIGS. 3 and 4 operates in stress-test mode according to a stress test protocol operated by the EXD CPU 130 to collect ST segment data over a range of heart rates. The stress test data (e.g., raw ECG waveforms, histogram data, summary statistics) that is collected during the stress-test mode is stored in event memory 474 of the IMD 10 that is allocated for stress test result data so that it does not contribute to the standard histograms data stored in the IMD 10. The patient exercises during the stress-test until the IMD 10 sends a signal to the EXD 120 that indicates the stress test is over causing the EXD 120 to emit a series of beeps to alert the user. Additionally, the EXD 120 can operate in a "Stress Test" mode which includes toggling a stress test LED (not shown in FIG. 3) on an on state to indicate a stress test is occurring and then transmitting the stress test data to a central station as the end of the stress test. Rather than using the EXD 120, the SDAPP 220 of FIG. 3 running on the patient's smart device 225 could provide appropriate instructions and notifications to structure the stress test. The EXD 120 or SDAPP 220 can instruct the patient to increase or decrease their exercise level to attain heart rates in selected ranges during this stress test protocol under the guidance of a pulse oximetry device.

The SDAPP 220 can initiate an "end stress test" command to through the EXD 120 to the IMD 10 when enough data at different heart rates indicates the IMD 10 heart rate histogram has sufficient data.

In an embodiment, the SDAPP 220 asks the patient if they are running on a treadmill or riding a stationary bike or ascending stairs or doing a different activity and then performs a stress test by presenting the patient with a virtual program for biking or running on a treadmill which makes the exercise more engaging and fun for the patient.

The EXD 120 or SDAPP 220 can transmit the stress test dataset collected by the IMD 10 to a remote center for review or store the data for upload to a Physician's Programmer 140 of FIG. 3 on a future clinic visit. Even if the stress test data are transmitted, the IMD 10 can be given sufficient memory that it retains certain stress tests data such as summary statistics in its memory in order to retain a history more than one stress test session result. The stress test dataset would include ST-level values as a function of HR as well as samples of the raw electrogram segments collected at different heart rates and the stress test continues until a minimum number of heart beats have populated each of the histograms or a maximum time limit has occurred. After the stress test data are transmitted to the remote center, a medical professional at the remote location can then compare the current stress-test dataset to one or more stress test datasets of the patient that were collected previously to assess if there has been a change in the patient's heart health.

In an embodiment, the Physician's Programmer 140 and/or SDAPP 220 would have the capability to display a graph of the stress test duration showing heart rate and ST deviation of shift.

In an embodiment the stress test design can be based on the patient's characteristics. For example, if the patient is older maybe the test is shorter, or the target heart rate criteria are lower and customized in the tablet that is running the test.

Time-Course & Waterfall Plots

FIG. 13 is an example of a present invention display or data print out implemented on the Physician's Programmer 140 or SDAPP 220 of FIG. 3 showing a surface graphical plot 600 of 24-hourly data collection time interval heart rate histograms similar to that of the table 500 of FIG. 11. Two features are of interest in this plot. The first is a period of elevated heart rate 602 between 11 am and noon. This could correspond to the patient exercising. In an embodiment of the IMD 10, an IMD accelerometer 75 of FIG. 4 is provided, to provide data that can displayed with elevated heart rate data to help differentiate elevated heart rate from exercise vs. elevated heart rate data from issues with beta blocker dosing or medication non-compliance.

Data from the IMD accelerometer 75 of FIG. 4 may also be used to create separate histograms that are for higher heart rates related to exercise. These histograms can be used to enable the IMD 10 to provide historical records akin to "stress tests" data, showing distributions of heart rates and ST changes for those heart rates during exercise. In this manner the system can be tailored to provide stress tests results in addition to monitoring for ACS events which occur during the normal heart rate range. The accelerometer or other non-cardiac sensed data can be stored and displayed as a history or waterfall plot, with relevant summary statistics, to show changes in a measure over time.

Another important feature shown in FIG. 13 is the generation of waterfall or other plots that allow tracking of a measured heart parameter over time. For example, the drop in heart rate 604 beginning at 10 pm (22:00) is an indication of the patient going to sleep. This low heart rate period extends until around 7 am when the plot shifts to higher heart rates after the patient is awake. These data can be used to monitor patient sleep as well as if the patient is getting up frequently during the night. Further, in patients with sleep apnea (obstructive or central), summary statistics, histogram, and raw electrogram segment data can be used to assess the effects of sleep disorders on cardiac activity and ischemic burden.

Collection of data by the IMD 10 that allow waterfall plots to be generated by the Physician's Programmer could be very useful to the patient's doctor with respect to diagnosing episodes of arrhythmias. For example, an elevated heart rate (such as 602) for at least 1 or 2 or 3 or more hours could be an indication of beta blocker improper compliance or dosing. If the heart rate elevated above 160 bpm it might indicate an episode of tachycardia. Similarly, an extension of the surface to the right along the heart rate value axis can detect episodes of bradycardia. A widening of the daily distribution of heart rate values could be an indication of irregular or unstable heart rate that is indicative of change in cardiac health status or onset of atrial fibrillation. In an embodiment, data which is sufficient to generate a waterfall plot over a 1-2 day period is collected by the IMD periodically (e.g. once every 2 months), and stored in the IMD 10 for future download such as may occur every 6 months during a visit to the patient's cardiologist. The waterfall plot data may be stored for heart rate, ST deviation, ST shift ST shift %, or any other measures collected by the IMD 10.

Wearable and Subcutaneous Monitoring and Alerting Devices.

Figure 14:
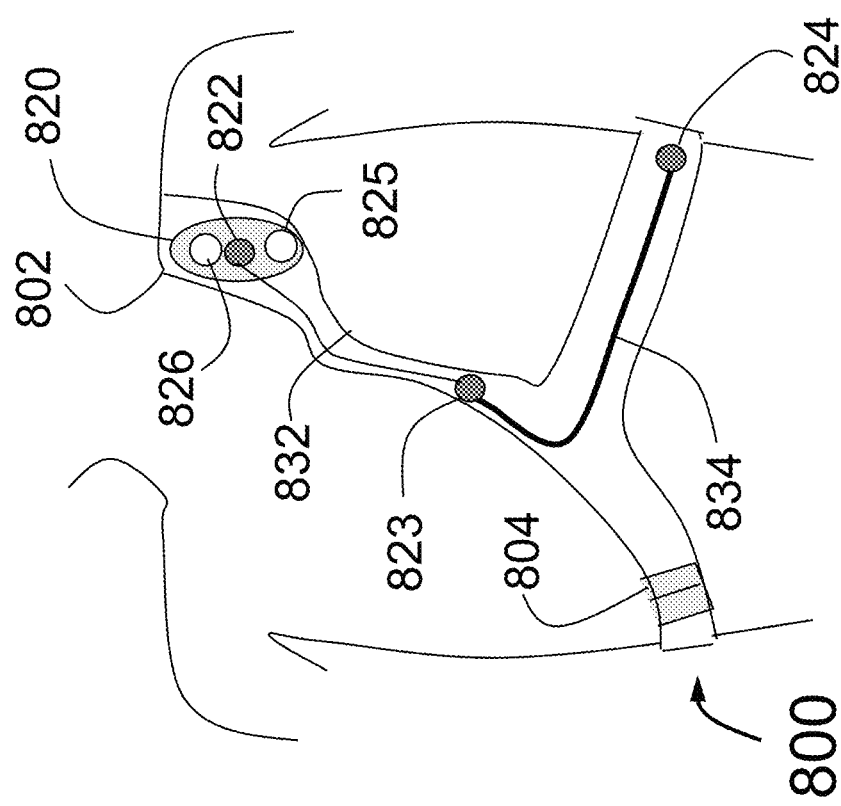
FIG. 14 is a schematic view of a Skin Surface Monitoring Device (SSMD)

FIG. 14 is a schematic view of a SSMD 800 that can be realized as a form factor that is worn on a patient such as a strap on vest including the vest 802 with buckle 804. In the shown embodiment, there are three electrodes 822, 823 and 824 that are located under the vest in contact with the patient's skin. Hopenfeld et al in U.S. Pat. Nos. 8,560,055, 8,682,422 and 9,375,151 describes an exponential averaging technique for ST monitoring that can identify occlusions of all three major coronaries when implemented with three electrodes as shown here. These include an electrode 822 in the upper left chest, 823 at the patient's sternum and 824 below the ribs on the patient's left side. These are known to allow two nearly perpendicular vectors for assessing ST changes with the first vector being from electrode 822 to 823 and the second vector being from electrode 823 to 824.

In this embodiment these electrodes would be connected through the cables 832 and 834 to a monitoring electronic device 820 which may be the SSMD 800 shown in FIG. 3. The monitoring electronic device 820 is envisioned to be able to include the features and capabilities of the ACSM 100.

The SSMD 800 and vest 802 could be configured in different sizes and shapes to accommodate men and women of different sizes. The use of the sternum of electrode 823 makes it possible to have the SSMD 800 place the electrode 823 and cable 832 between a woman's breasts. Ideally, the shape of the vest 802 as shown in FIG. 14 should route from the shoulder area along the clavicle and then down to the sternum since this will avoid women's breasts and problems due to movement of the shoulder.

Most of the features of the IMD 10 and EXD 120 of FIGS. 3 and 4 could be combined in the SSMD 800 which would not need a separate EXD as it is outside of the patient's skin and can easily have direct access to the cellular network, Bluetooth to pair it with a smart device 225 of FIG. 3 or local Wi-Fi. The SSMD 800 could therefore also include an alarm silence button and/or an event tagging/panic button 826.

Also shown are embodiments of the SSMD 800 and/or the SCM 900 realized using three electrodes. Without being bounded by theory, while 2-5 electrodes may be realized on a small housing with a form factor somewhat longer than a standard loop recorder (implanted) or patch (cutaneous), it is contemplated that three electrodes would be one preferred embodiment for use in ST monitoring for ischemic events including ACS events/heart attacks and demand ischemia. The separation between electrodes in the SCM 900 may need to be longer than that of a standard loop recorder.

FIG. 14 shows a 3-electrode vest embodiment of the SSMD 800. Two electrodes would be sufficient for heart rate monitoring and arrhythmia detection. Without being bounded by theory, a combination of two or more SCMs 900 may function to obtain sufficient coverage across the torso to identify ST segment changes associated with occlusions of all three major coronary arteries.

It is also envisioned that an implantable version of the SSMD 800 could be implemented with tunneled leads under the skin or a combination of subcutaneous and wearable components. In one embodiment, the external components could be implemented to provide inductive power transfer to the subcutaneous components.

FIG. 15A is a schematic view of a Subcutaneous Cardiac Monitor (SCM) 900. It has two electrodes 902 and 904 separated by a distance L1. L1 should be 4 to 50 cm. The electrode 902 is in end section 905 of the SCM 900, the electrode 904 is in end section 907 of the SCM 900. The center section 906 of the SCM 900 is envisioned to contain the components that include electronics, battery, RF transducer and vibrator similar to the IMD 10 of FIG. 4. With a two electrode SCM 900, R-R monitoring and syncope detection similar to current loop recorders can be performed.

The sections 905 and 907 would preferably be flexible to better to contour to the subcutaneous space where it is implanted. While the end sections 905 and 907 are shown as the same cross section as the center section 906, it is envisioned they could be of smaller cross section and act as a lead. The electronics could also be located in any or all of the three sections.

To adequately identify coronary occlusive events using ST shift detection, it is envisioned that two SCM 900 devices positioned appropriately with a spacing of the electrodes 902 and 904 greater than 5 cm and ideally greater than 10 cm with an algorithm for the detection of excessive ST shift. This would replace the need for a long-tunneled lead to get the needed two subcutaneous vectors preferred for ST monitoring of all three major coronary arteries. For example, one lead might be under the skin of the left chest above the breast parallel to the cable 832 of FIG. 14, a second SCM 900 could be under the left ribs. It is envisioned that if either device detected an acute ST change, an internal or internal and external alarm with or without cellular messaging could occur.

FIG. 15B is a schematic view of an additional embodiment of a subcutaneous Cardiac Monitor (SCM) 951. The SCM 951 is envisioned to have a length L2 between 10 and 100 cm and would have at least 2 electrodes 952 and 954 but would preferably have a third electrode 953. It has two end sections 955 and 957 and a center section 956. The center section 956 of the SCM 951 is envisioned to contain the components that include electronics, battery, RF transducer and vibrator similar to the IMD 10 of FIG. 4, however the components could also be located in any or all of the three sections.

The embodiment of the SCM 951 with three electrodes 952, 953 and 954 and a length of 50 to 100 cm would be practical for implementation of the algorithm for the detection of excessive ST shift. Specifically, a preferred use would have the SCM 951 tunneled under the skin in a similar electrode configuration to that of the SSMD 800 of FIG. 14 with one end electrode such as 952 located under the left clavicle the center electrode 953 located near the sternum and the other end electrode such as 954 located near the bottom of the rib cage on the patient's left side. This configuration produces two orthogonal vectors that are needed to accurately identify ST changes induced by occlusion of all three major coronary arteries. It is also envisioned that two SCM 951 configured with two electrodes each could together accomplish the same ability of two orthogonal vectors for occlusion detection based on ST shifts.

Current loop recorder such as the Medtronic REVEAL© or Abbott CONFIRM© are a type of SCM (and may serve as the basis of a form factor for the disclosed SCM) but have only about 4-10 cm spacing. These do not have an appropriate patient referenced machine learned algorithm and high pass filter so that ST monitoring is not a viable capability. It is envisioned that the SCMs 900 and 951 could be configured to provide not only ST monitoring and patient alerting like the AngelMed Guardian©, but could do so in a format that does not require intracardiac sensing.

Cardiac Monitoring Protocols Related to Elevated Heart-rates.

Figure 21A:
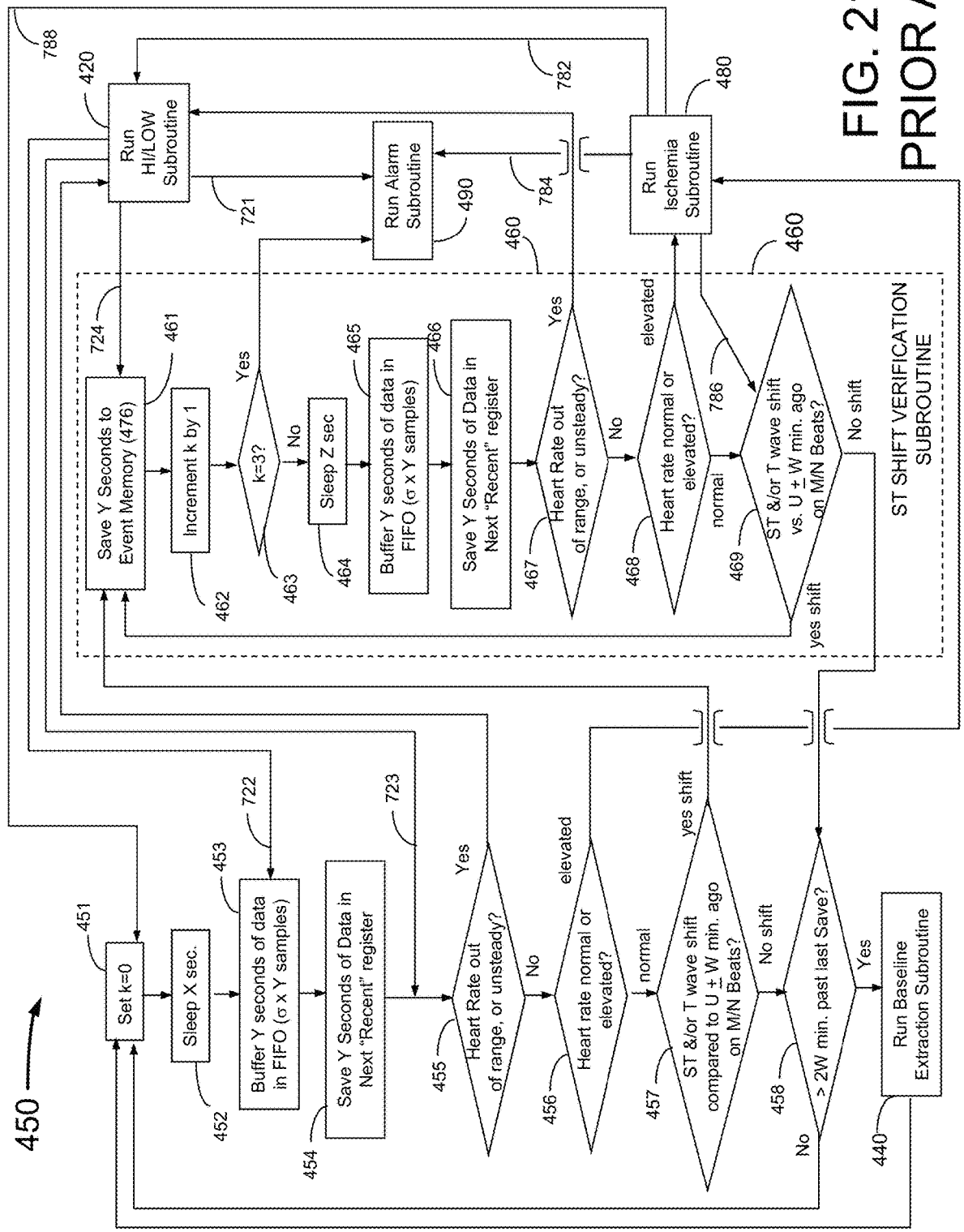
FIG. 21A shows a block diagram for the process for identifying excessive ST shift events of a prior art system.

FIG. 16A shows an embodiment of a ST shift verification subroutine 450 that has been disclosed as a prior art system and is also included as FIG. 21A of this specification. In the subroutine 450 in step 468 the average R-R interval for an electrogram segment being processed is assessed to determine if the average heart rate of a segment is in the defined Elevated range. Since the R-R interval for a beat in the segment is the time interval from the prior beat R-wave to the current beat's R-wave, the average R-R interval can be calculated by taking the average of the set of R-R intervals for the beats in the segment. Note, the first beat of a segment of sensed cardiac data does not have an R-R interval that is used in calculating the average because there is no prior beat. The average heart rate (HR) for the segment is calculated from the average R-R interval of the segment as 60 seconds/average R-R interval in beats per minute (BPM).

If the segment in step 468 has an average HR that is within the Elevated range then subroutine 450 runs the ischemia subroutine 480 to determine if there is demand ischemia characterized by excessive ST shifts at elevated heart rate. In an embodiment, the routine 480 may also assess accelerometer data to assess if the patient is likely to be exercising. The output of step 480 can be that the combined ST-shift data and accelerometer data both meet a demand ischemia criterion and a message is stored, an alarm is triggered, and/or is presented to a patient which indicates that exercise-induced ischemia has been detected. This capability is similar to running a stress test where the patient exercises to elevate their HR and ST changes are assessed to determine the presence of demand ischemia. This prior art embodiment does not evaluate the duration of elevated heart rate which if extended or prolonged can be an indication of improper compliance or dosing related to beat blocker medications.

FIG. 16B is a flow chart of the subroutine 650 which includes a novel and useful modification to the subroutine 450 of FIG. 16A as implemented in an embodiment of the present invention EID 10. The method detects prolonged periods of elevated heart rate that may be indicative of improper beta blocker compliance or dosing. In step 650 detection by step 668 of an electrogram segment with an average elevated heart advances the subroutine 650 to step 669 where the duration of elevated heart rate is compared to a pre-set threshold. The duration may be calculated with a requirement that all segments in a set of segments be assessed as within an elevated threshold range. Alternatively, a range of 50%-100% of the total set of recorded electrogram segments or individually measured R-R intervals may be set as the minimum proportion that may be required to be elevated. For example, if a 1-hour period contains 80% of segments that are evaluated as elevated and the criterion requires 90%, then that hour will not contribute to the total time for which elevated HR is assessed as having occurred. If the duration exceeds the threshold, and the elevated heart rate is determined to be prolonged or extended, then subroutine 650 initiates a See Doctor Alert in step 690. In an embodiment, step 690 may include simply setting a flag that extended elevated HR has been detected or can include providing an alert message that specially informs a user that an extended period of elevated heart rate has been detected or informs a user that they may have forgotten to take their Beta blocker medication, or asks the user if they have forgotten to take their medication (and the user may use a smart device 225 to provide a user response). In an embodiment, the method 650 then operates to perform the Ischemia subroutine 680 as in the prior art subroutine 450 to determine if the patient is experiencing demand ischemia. In other words, in an embodiment step 680 is otherwise the same as step 480 of FIG. 16A. Step 668 also performs the same function as step 468 of FIG. 16A. Alternatively, if step 690 determines there is a period of extended elevated HR then step 680 does not occur and the method returns to collecting more data and performing step 668.

Figure 16C:
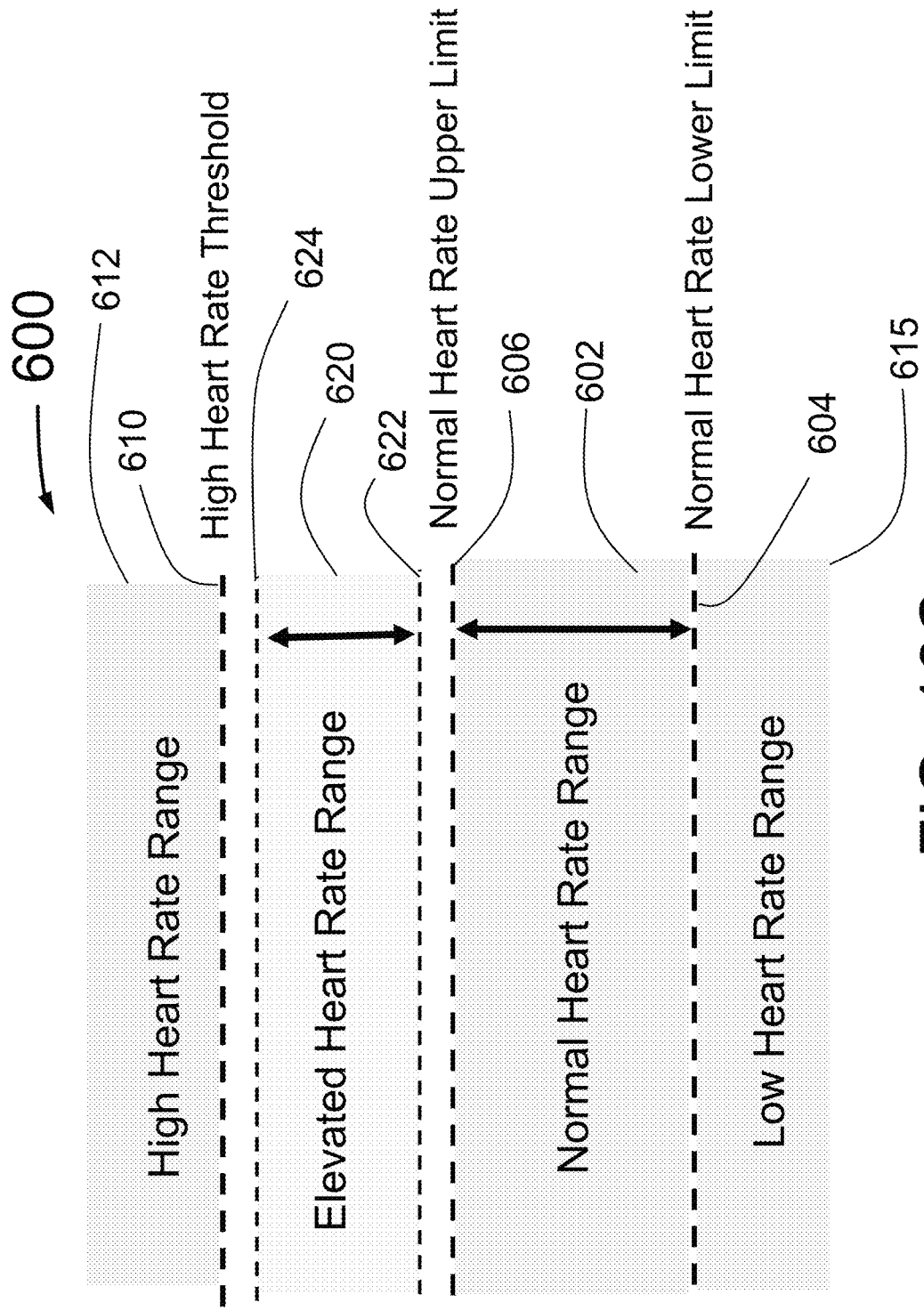
FIG. 16C is a diagram showing 4 heart rate ranges and associated limits and thresholds.

The capabilities described in the prior art for the detection and patient alerting for heart rate anomalies are incorporated herein. This includes the use of at least four ranges of heart rates. As seen in FIG. 16C for the heart rate range schematic, these are: a) a low heart rate range 615 is shown for any heart rate below a lower limit 604 of the normal heart rate range b) a normal range 602 with lower limit 604 and upper limit 606; c) an elevated range 620 with lower limit 622 and upper limit 624 where the lower limit 622 of the elevated range 620 is greater or equal to the upper limit 606 of the normal range 602 and the upper limit 624 is less than or equal to the high heart rate threshold 610 and; d) a high heart rate range 612 is shown for any heart rate above the high heart rate threshold 610.

In some embodiments, the elevated range 620 may be broken into sub-ranges that can be set manually or in one embodiment the ACMS 100 would automatically set these sub-ranges based on the normal heart rate upper limit 606 and the high heart rate threshold 610.

The present invention ACMS 100 of FIG. 3 includes the ability to detect and alert the patient to detection over a pre-set period of time, for each of the following: a) high heart rate above the high heart rate threshold 610, b) low heart rate below the lower limit 604 of the normal range, and c) irregular heart rate characterized by a proportion of beats with an R-R interval a pre-set level below the measured average heart rate. In an embodiment, the cardiac event detections of the present invention differ from the prior art since the detection and event flagging, or alerting envisioned here, may occur for extended or prolonged periods of elevated heart rate, that are selected or defined, where at least 50% of the beats have R-R intervals corresponding to a heart rate within the elevated range 620. In a preferred embodiment, an alarm would be generated when at least a defined percentage such as 50%, 60%, 70%, 80%, 90% or 100% of beats (or segments) are classified as being in the elevated range 620 for a pre-set prolonged period of time, that may be for example, 10 minutes or more. In one embodiment the period of time is more than 1-3 hours. In a preferred embodiment the period of time should be more than 3 hours as it is unlikely that a patient with an ACMS 100 would exercise for that long and perhaps a time period as long as 6 hours could be used. Additionally, the percentage used by a criterion can be set to be between 50% and 100%, and this may be set by a doctor or statistically derived based upon patient reference data. Alternatively, in embodiments, the extended period to detect elevated heart rate could be selected to be one or more days.

The ACMS 100 includes alerting mechanisms that can provide two or more types of alerts associated with at least two levels of severity. The levels of severity would correspond to different levels of danger to the patient associated with the alert. The specific levels of severity for each detected event with an alert would be pre-programmed into the ACMS 100. In programming the ACMS 100 using the Physician's Programmer 140 of FIG. 3, each type of detected event can be pre-programmed to no alert or one of the two or more levels of severity. For example, a detected excessive ST shift indicative of a potential heart attack would be set to the highest level of severity while detection of an extended period of elevated heart rate would be set to a lower level of severity. The detection of an extended period of elevated HR may be defined to simply set a flag in memory indicating that this was detected for a particular set of times or days. Additionally, in embodiments, if an alarm such as a non-urgent See Doctor alert is provided to a patient, then subsequent notifications may not be permitted to be provided to a patient for at least 24 or 48 hours (although additional flags may be stored in memory to enable the total event duration to be reviewed upon a subsequent clinic visit) so that the patient does not receive too many alarms.

In an embodiment, a system for monitoring a patient's heart rate and alerting the patient of an abnormal condition indicative of either patient beta blocker non-compliance or improper beta blocker dosing comprises the following. A device such as IMD 10 of FIG. 4, having at least two implanted electrodes e.g. the electrodes 14 and 18, adapted to sense electrical signals from the heart of the patient. The device has electronic circuitry devoid of circuitry adapted to deliver electrical energy through the electrodes e.g. the electrodes 14 and 18 to the patient's heart coupled to said at least two electrodes for sensing and electronically operating on said sensed electrical signals to provide operational electronic signals. The device also has a processor 44 that is in communication with the electronic circuitry for computing and storing said operational electronic signals. The processor 44 of the IMD 10 of FIG. 4 is adapted to compute an average heart rate of the patient during a pre-programmed time period for a multiplicity of heart beats. Also, the processor 44 is further adapted to store pre-set values of: (1) a normal heart rate range having an upper limit; (2) a high heart rate lower threshold for detecting tachycardia; and (3) an elevated heart rate range that lies between the normal heart rate range upper limit and the high heart rate lower threshold, as is shown in FIG. 16B.

The system has a patient alerting mechanism (which may be in the IMD 10 such as an alarm system 48 with vibrator 25, or which may be realized via communication with an EXD 120 that is in communication with the processor for automatically alerting the patient according to an alerting protocol defined in at least one processor. The alerting may occur (devoid of any input by the patient) when the computed average heart rate for a portion of the multiplicity of heart beats during a pre-programmed time period is within the elevated heart rate range. Additionally, the processor is further configured to responsively (a) detect excessive ST shifts as a function of said heart rate normal range, and (b) alert the patient of beta blocker non-compliance or improper beta blocker dosing following detection of a patient's heart rate meeting at least one beta blocker non-compliance detection criterion, said alert informing the user specifically about detection of cardiac activity reflective of beta blocker non-compliance or improper beta blocker dosing. For example, text messages or other alert signals can specifically inform a patient about a potential issue with their beta blocker medication or inform the patient that their heart rate has been elevated for a long time. The alert may include information about the elevated heart rate and the duration it has existed.

Alternatively, a system for detecting a cardiac event in a human patient may comprise at least two electrodes implanted or on the skin surface of the patient for obtaining the electrical signal from the patient's heart, the electrical signal being an electrogram. The system also includes an implanted cardiac monitoring and alerting system devoid of circuitry adapted to deliver electrical energy through the electrodes to the patient's heart including:

(a) analog-to-digital converter circuitry for digitizing the electrogram to produce electrogram segments each having a time duration that is at least 1 second;

(b) means for processing a first electrogram segment at a first predetermined time to extract at least one baseline heart signal parameter value of the patient;

(c) memory having means for storing at least one baseline heart signal parameter value, memory further having means for storing lower and upper limits for the patient's normal heart rate range and an elevated heart rate range, the lower limit of the elevated range being at or above the upper limit of the normal range;

(d) means for processing a plurality of electrogram segments at a later, second predetermined time to extract at least one heart signal of the patient from said plurality of electrogram segments; and, (e) a processor coupled to the memory and designed to detect the cardiac event when the at least one heart rate signal extracted at the second predetermined time shifts by more than a predetermined threshold amplitude from the at least one baseline heart signal parameter value extracted at the first predetermined time, the processor further configured to compute the average heart rate of each of said electrogram segments, the processor further adapted to detect a prolonged period of elevated heart rate when the computed average heart rate is in the elevated heart rate range for at least 50% of electrogram segments over a pre-set time period.

In an alternative embodiment, an implanted cardiac monitoring device for monitoring the heart of a human patient, the device includes at least one connector for attaching to the device at least one implantable lead, the at least one lead including at least one electrode for sensing the electrical signal from the patient's heart. The device also includes electronic circuitry devoid of circuitry adapted to deliver electrical energy through the at least one electrode to the patient's heart including: (a) analog-to-digital converter circuitry for digitizing the electrical signal sensed by the at least one electrode; (b) means for processing the digitized electrical signal to compute the average heart rate over a multiplicity of pre-set periods of time; (c) digital memory for storing pre-set lower and upper limits for a normal range of patient heart rate and pre-set lower and upper limits for an elevated range of heart rate; and (d) a processor coupled to the digital memory adapted to detect all of the abnormalities in patient heart rate selected from the group including a set of rates. In an embodiment, the set of rates includes: i) Low heart rate when the average heart rate is less than the lower limit of the normal heart rate range for a low heart rate detection time period, ii) High heart rate when the average heart rate exceeds the upper limit of the elevated heart rate range for a high heart rate detection time period; iii) Elevated heart rate when the average heart rate is between the lower limit of the elevated heart rate range and the upper limit of the elevated heart rate range for an elevated heart rate detection time period which is an extended or prolonged period of elevated heart rate that is selected r defined to be for example, more than 2 hours; and, Irregular heart rate when the average heart rate of a first pre-set percentage of the beats in a measured over an irregular heart rate time period having R-R intervals more than a second pre-set percentage below the average heart rate for the irregular heart rate time period.

In embodiments, the ACMS 100 of FIG. 3 includes features that enhance differentiation between ST changes due to coronary occlusion at a normal resting heart rate and ST-changes due to demand ischemia:

1. Additional histograms bins that collect data on the distribution of ST deviation levels in a subset of beats that lie within the "Normal" heart rate range but are within a higher portion of the normal range. Instead of a single Normal heart rate range histogram for calculating ST detection thresholds, two (or more) histograms are defined to cover the normal range. These would be a Low-Normal histogram and High-Normal histogram that would be used to calculate the respective positive and negative thresholds for the respective range.
2. For beats with RR intervals in the High-normal range the ischemia detection would require an increased number of shifted beats or increased interval of excessive ST shift to trigger an Emergency alarm.
3. Demand ischemia ST shifts recorded by the IMD (with a can-to-tip vector), are often negative. Added processing as described in 1. or 2. above, can be set to occur for both positive and negative shifts, or can only be defined for excessive ST shifts beyond a negative threshold within a High-normal range.

In embodiments, the ACMS 100 includes features that enhance differentiation between ST changes due to coronary occlusion and ST-changes due to demand ischemia:

1. Adding additional histograms to collect data on the distribution of ST deviation levels in a subset of beats that lie within the "Normal" heart rate range but are within a higher heart rate portion of the normal range. These can be used to create "High-normal" excessive ST thresholds for detecting an occlusive event.
2. For beats with RR intervals in the High-normal range the ischemia detection rule requires an increased number of required beats or increased time period of excessive ST shift that must occur before triggering an Emergency alarm for an occlusive event.
3. In some patients, demand ischemia ST shifts recorded by the IMD (with a can-to-tip vector), may be negative. The present invention contemplates that the added processing as described in 1. or 2. above, will only occur to identify excessive ST shifts beyond a negative threshold within a High-normal range.

Event Tagging and Panic Button Operations

Figure 17:
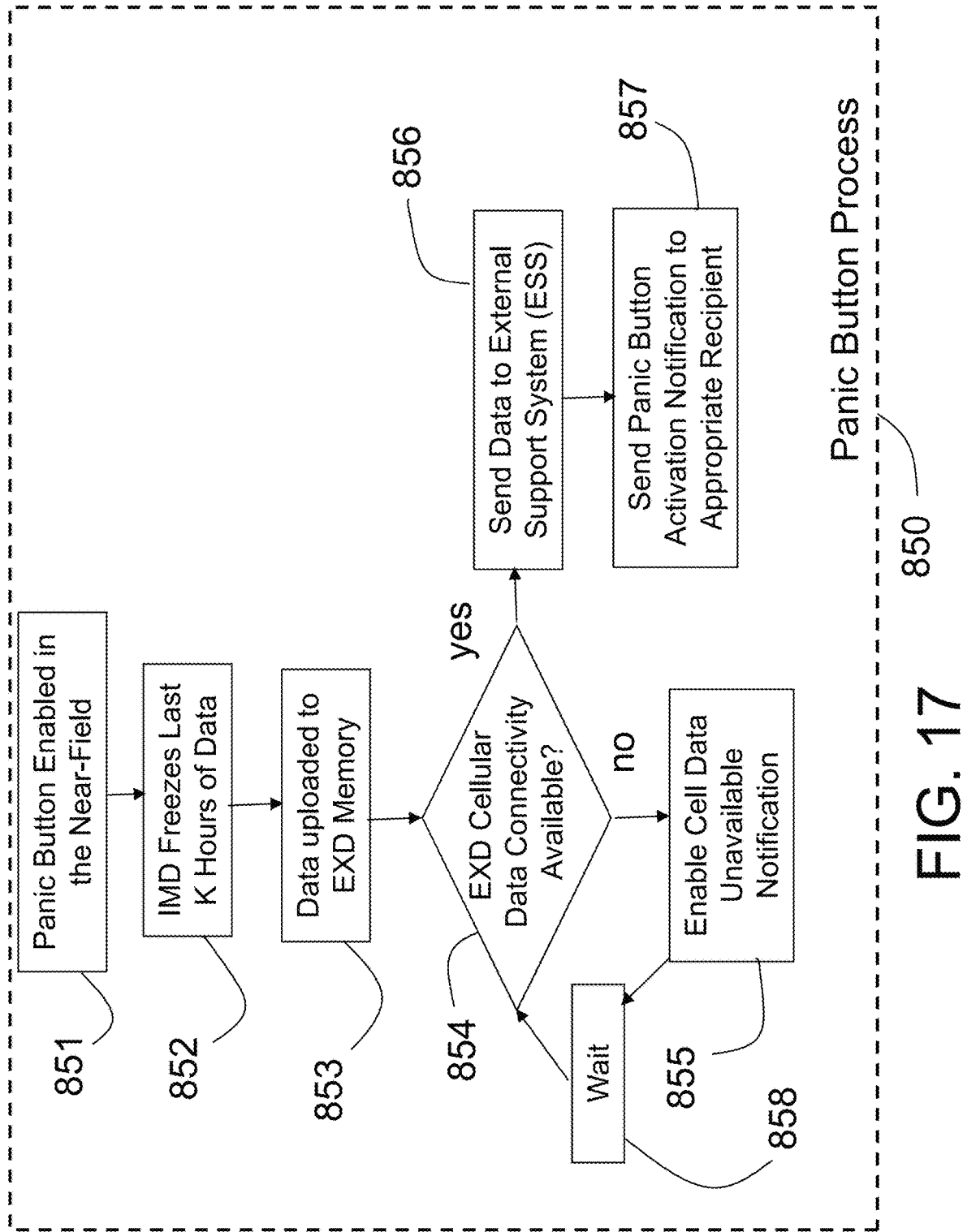
FIG. 17 is a flow chart of the process used by the ACMS to enable patient request for assistance via a "panic button."

FIG. 17 shows an embodiment of the event tagging/panic button process 850 for the ACMS 100 responding to the patient activation in step 851 of the event tagging/panic button feature. While this example treats the event/panic button similarly, obviously the process can be adjusted for different buttons which correspond to different events, which may be urgent or simply important or informational.

In an embodiment, the EXD 120 of FIG. 3 can use its display to provide menu driven event tagging by the patient or a simple single button may be used. The example shown in FIG. 17 begins with at least one event tagging/panic button 121 of the EXD 120 of FIG. 3 being activated by the patient in the near-field of the IMD 10 (or SCM 900). This triggers a defined set of one or more operations such as activating the IMD 10 or SCM 900 to freeze in memory data collected over the last 24 hours in step 852. Alternatively, step 852 may include transfer these data to an area of IMD 10 memory which is reserved for storing event/panic/stress test data, so the memory/storage operations of the IMD 10 remain unchanged. Alternatively, when the IMD 10 has a rechargeable battery and conserving power is not a limiting factor then step 852 may cause a communication session to start, and if successful then data, including individual heartbeats, are transmitted to an EXD 120, smart device 225, or ESS 240 of FIG. 3 (and data can be collected and periodically transmitted for a defined period thereafter). If data communication is not started in step 852, then in step 853 these data along with additional data stored in the IMD 10 or SCM 900 such as ST deviation histograms or RR histograms are uploaded to the EXD 120 memory at a time when the next communication session is established between the IMD 10 and another component of the ACMS 100. Next in step 854, the EXD 120 checks for cellular data connectivity either directly through the cellular voice/data sub-system 128 with cellular voice/data sub-system antenna 129 of FIG. 3 or through a paired smart device 225 through the Bluetooth/Wi-Fi transceiver 147 with antenna 148 of FIG. 3. If connectivity is available, the EXD 120 in step 856 transmits the data it uploaded in step 853 to the external support system 240 of FIG. 3 which is typically a HIPAA compliant server. The EXD 120 would then in step 857 send notification of a panic button being activated to the appropriate recipient. Such a recipient could be a medical practitioner having a Smartphone, Tablet or PC running the SDAPP 220 of FIG. 3 and/or a text message or other notification to the patient's care giver, cardiologist or other appropriate recipient. Data relating to the event can be sent to the smart device 225 of FIG. 3 running the SDAPP 220 or the message sent to the smart device 225 could allow the SDAPP 220 to retrieve the additional data from the ESS 240.

If connectivity is not available, step 855 has the EXD 120 and/or IMD 10 (or SCM 900) notify the patient that cellular data is unavailable using vibration, a visual display or acoustic message. It is also envisioned that after notification of cellular connectivity being unavailable in step 855, that the process could wait a pre-set time in step 858 and then try again. If this occurs, the event tagging/panic button process 850 would only allow a certain number of tries before giving up, or halting for a second pre-set time of several hours or days, and providing the patient with notification of the failure.

It is also envisioned that instead of a first step of uploading data to the EXD 120 followed by the EXD 120 transmitting the data after cellular connectivity is established, the process could first establish cellular connectivity then the data could be transmitted through the EXD 120 to the ESS 240 without first storing the data. A similar process to event tagging/panic button process 850 can result from the event tagging/panic button 826 incorporated into the SSMD 800 of FIGS. 3 and 14.

Setting Thresholds for ST-Related Measures

FIGS. 18, 19 and 20A through 20F describe embodiments of the present invention that provides improved accuracy for the determination of thresholds for detecting abnormal ST-changes including excessive ST shifts indicative of a potential heart attack. They include descriptions of the use of histogram-based storage of ST data to compute thresholds for detecting demand ischemia and/or coronary vessel occlusion, e.g. excessive ST shift detection thresholds. The techniques described can be used independent of whether the threshold computations occur in the ACMS Physician's Programmer 140 or the IMD 10, SSMD 800 SCM 900 or EXD 120 of FIG. 3.

In embodiments, the present invention enhances patient self-referenced excessive ST shift detection threshold setting mechanism by:

1. Separately computing, the positive and negative variability used to define the normal range of a patient's ST-segment deviation (ST level relative to another portion of the heart signal, e.g., a portion between the P and Q wave). In a preferred embodiment this is accomplished using histograms for efficient storage of the ST deviation measurements although a less efficient direct storage of the data for each beat measured could be used.

2. Utilizing a threshold that reflects a value significantly greater than the normal range of an individual patient's ST-segment measurements such as by using a selected number of standard deviations (e.g., 3 standard deviations) from the mean, median or zero value for ST deviation to determine positive and negative excessive ST shift detection thresholds for detecting excessive ST shift. A preferred embodiment of the present invention uses three standard deviations from the zero value.

In embodiments, excessive ST shift being an ST shift % that exceeds the positive or negative excessive ST shift threshold as described below indicating acute ischemic events that include: A) Total occlusion of a coronary artery indicative of an ACS event including heart attacks; and, b) Demand ischemia in the heart muscle at elevated heart rates indicating a partial blockage of one or more coronary arteries similar to a failed stress test.

3. Separately calculating standard deviations for asymmetric ST deviation distributions. In FIGS. 18-20D, these un-normalized ST deviation distributions are in histogram formats and ADC units which are the measurement of heart signal output of the Analog-to-Digital Converter 41 of the IMD 10 of FIG. 4.

Specifically, a preferred embodiment "mirrors" the positive portion above a center point of the ST deviation distribution to calculate the positive standard deviation while the negative distribution of ST-shift values are replaced by a mirror of the positive distribution to create a symmetrical distribution-relative to zero ST deviation where the level or voltage of the ST segment is the same as the level or voltage of the PQ segment. This zero ST deviation is sometimes referred to as iso-electric level. The standard deviation of this mirrored distribution (i.e. the derived positive standard deviation) can then be calculated and then used for calculating an un-normalized positive ST deviation threshold (using a multiple of the derived positive standard deviation, e.g., 3 standard-deviations). Similarly, the method replaces the positive portion of the distribution with a mirror of the negative portion of the distribution to calculate a derived negative standard deviation with respect to a center point such as zero ST deviation. This is then used for calculating an un-normalized negative ST deviation threshold (using a multiple of the negative standard deviation, e.g., 3 standard-deviations). While the zero value is used in the preferred embodiment, a different center point such as the mean or median of the distribution may be used. This technique has the advantage that it will work for both symmetric and asymmetric distributions of ST-segment levels.

4. The positive and negative excessive ST shift detection thresholds used by the ACMS monitor 100 of FIG. 3 are then set by normalizing the positive and negative ST deviation thresholds determined by beats analyzed over a data collection time period to an average value of heart signal amplitude over a similar data collection time period. This normalization step is important with respect to intracardiac leads which encapsulate over time with impedance changes that will affect the heart signal amplitude. By always normalizing to the heart signal amplitude, the impact on event detection from such changes as well as slow changes in a patient's heart itself are minimized. In the preferred embodiment described with FIGS. 18-20D, the values used for ST deviation and heart signal amplitude are in ADC units.

5. Acute adjustment of the excessive ST-shift thresholds can also be made using a correction factor that is based upon the patient's recent history of variability as a function of time of day or other variable that characterizes a particular patient's heart rhythm profile (e.g., postural effects). For example, a correction factor may be used to slightly increase or decrease the ST-shift threshold (or other measure of ischemia relied upon by the ACMS 100 of FIG. 3) based upon whether a clock time indicates it is morning, afternoon, or night, based upon body angle, or other variable.

The following detailed description discusses the preferred embodiment of setting both negative and positive excessive ST shift detection thresholds using collected ST data stored in histogram format.

Accurate detection of abnormal ST-segment values such as excessive ST shift detection is improved by use of patient-specific detection thresholds for detecting excessive ST changes as can be reflected by ST shift % measures. Prior art systems provide an overview of the use of histogram format stored ST levels to identify the distribution of patient ST levels over days or weeks. The distributions can be utilized to calculate detection thresholds which are used in detecting excessive ST shift in real time.

While the device can use ST segment measured voltages in the detection of ischemia, a preferred embodiment measures "ST deviation" which is the relative amplitude of each heartbeat's ST segment compared to a reference such as an Iso-Electric value which is the typically flat portion of the heart signal wave form that exists for each heartbeat between the P wave and the Q wave, (the PQ segment). An example of the P, Q, R, S and T wave portions of a heartbeat of the sensed heart signal are shown in FIG. 2 of the '023 patent. ST levels and ST deviation may be measured, computed and/or stored as any one or more of the following: A) actual measured voltage; B) arbitrary "ADC" units (e.g., units based on integral numbers produced by the Analog-to-Digital Converter (ADC units)); C) as a difference from an isoelectric, or D) as a percentage (or fraction) of a measured amplitude of a portion of the amplitude of the beat (e.g., the QRS section of a beat).

It is important to measure both ST deviation and compute and store the average heart signal amplitude (e.g., QRS amplitude or R-wave amplitude/height) over approximately the same time periods for normalization as the amplitude of heart beats measured in the heart signal from an implanted lead will likely change slowly over time. In an embodiment, corresponding measures of a composite baseline may be used for normalization.

The excessive ST shift threshold calculations are based on statistical calculations including the mean, median and variability of the distribution (e.g., standard deviations) in one Normal and one or more Elevated heart rate ranges. For example, the portion of heart rates between the upper limit of the Normal heart rate range and a High heart rate threshold may include a single heart rate range or be sub-divided into a multiplicity of heart rate ranges. In a preferred embodiment 4 of these sub-divided heart rate ranges could be programmed in the ACMS 100 of FIG. 3. These may be set manually or be automatically created by the ACMS 100 based on a sub-division algorithm that sub-divides the range of heart rates between the upper limit of the Normal range and the High heart rate threshold.

In a preferred embodiment, ST deviation and average heart signal amplitude are measured and stored in ADC units. Normalization to the average heart signal amplitude may occur in different manners. For example, in the computation of excessive ST shift, detection thresholds are calculated as a percentage or fraction of the average heart signal amplitude. Alternatively, in the computation of ST shift % for a newly collected beat of the sensed heart signal, the ST shift is calculated as the change in ST deviation between said beat and a baseline value of ST deviation computed as a percentage of a baseline average heart signal amplitude where the baseline data was collected in a prior time period, or across a number of prior periods (e.g., the baseline may be the composite of 24 hourly baseline heart signal samples collected at the start of each hour).

In an embodiment, there is provided a method for providing a contingent operation, such as actuating an alarm, responsive to detection of excessive ST shift from a heart signal of the patient. Initially, the ST deviation is measured for each beat of a multiplicity of beats from a PQRST representation of the heart signal during a data collection time period. The ST deviation is substantially an ST segment average voltage minus a PQ segment average voltage within each of the beats. Subsequently, there is the creation and storing at least one histogram defined by a set of bins, with each of the bins being associated with an ST deviation range. Each bin maintains a running count of the number of beats whose ST deviation is measured to be within the ST deviation range associated with a respective bin during one data collection time period. The at least one histogram provides an efficient means to store the distribution of ST deviation values over a data collection time period.

A positive excessive ST shift detection threshold is calculated by processing the data only from the bins associated with ST deviations greater or equal to zero. A negative excessive ST shift detection threshold is calculated by processing the data only from the bins associated with ST deviations less than or equal to zero. The patient is then alerted when at least one set of the multiplicity of beats has an ST shift % that exceeds one of the positive or negative excessive ST shift detection thresholds in the associated positive or negative direction. The at least one set of the multiplicity of beats can be one segment of a multiplicity of beats, or a defined number of segments within a defined interval (e.g., 3 out of 5 consecutive segments).

In embodiments, this process may be realized in different manners such as using external ACMS Physician's Programmer 140 of FIG. 3. In this example, the ST deviation and heart signal amplitude data are uploaded from the IMD 10, SSMD 800 or SCM 900 of FIG. 3 to the Physician's Programmer 140. The programmer 140 then calculates excessive ST shift detection thresholds which are used to detect potential ACS events. These thresholds are then downloaded to the IMD 10, SSMD 800 or SCM 900. Alternatively, the IMD 10, SSMD 800 or SCM 900 could be programmed to compute excessive ST shift detection thresholds after collecting a sufficient amount of ST level data (e.g., at least 5-14 days). This can occur automatically or in combination with interaction with local or remote ACMS components.

Figure 18:
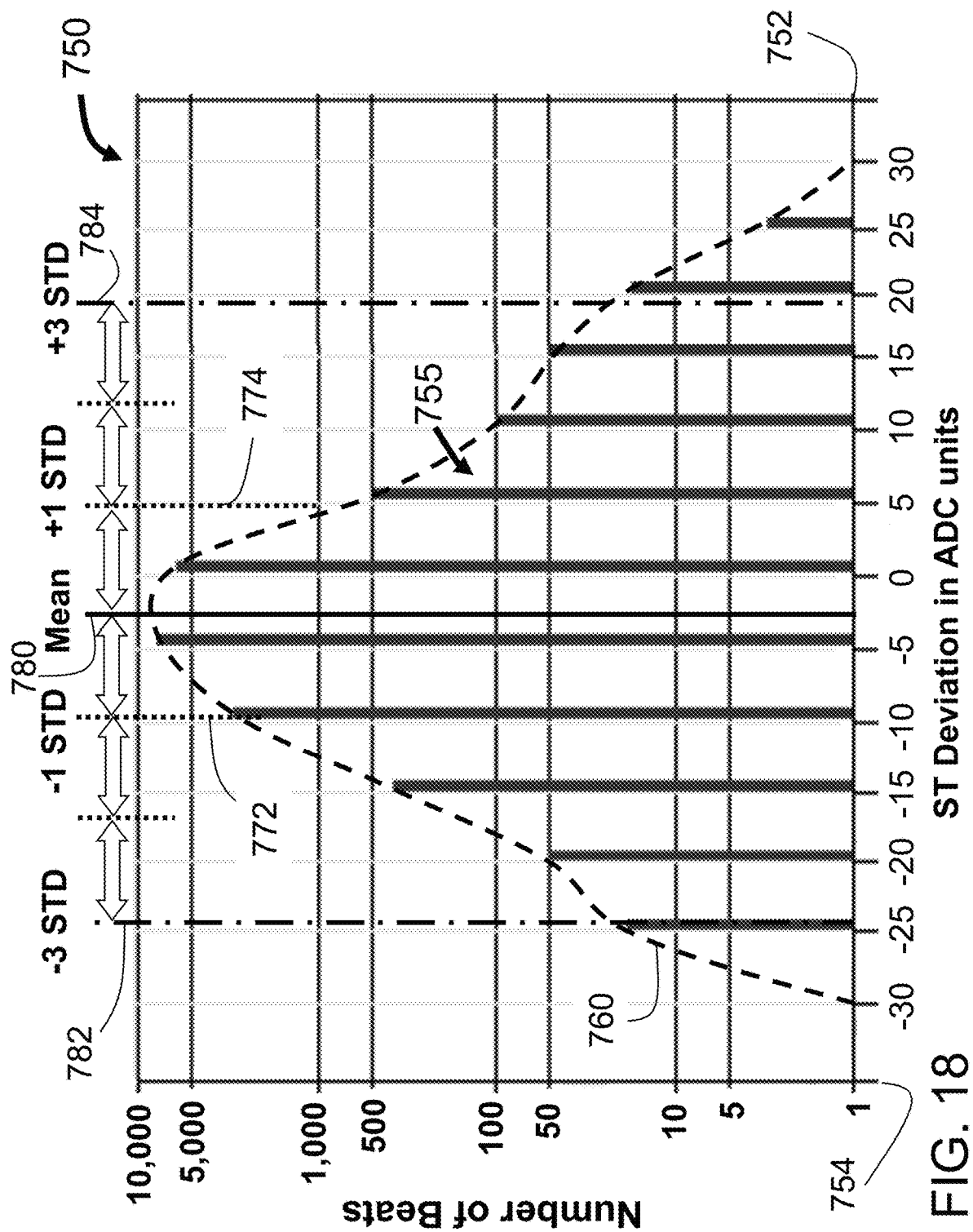
FIG. 18 is a graphical depiction of the data from an ST deviation histogram utilized to calculate positive and negative excessive ST shift detection thresholds.

FIG. 18 shows an example of a relatively symmetric ST deviation histogram 750 collected over a sufficient number of days required to obtain a large set (e.g., tens of thousands) of analyzed heart beats (e.g., a range of 7 to 14 days). The ST deviation histogram 750 is shown as a logarithmic plot as seen in the vertical axis 754. The horizontal axis 752 shows 13 bins corresponding to 13 values of ST deviation in the arbitrary ADC units that are produced by the ADC Converter. In this example, each bin is 5 ADC units wide. For example, the −30 bin is incremented if the ST deviation in ADC units for a beat is −32, −31, −30, −29 or −28). Similarly, the 0 bin is incremented if the ST deviation in ADC units for a beat is −2, −1, 0, 1 or 2. FIG. 18 is an example that shows bins labeled −30 to +30, while the actual values will depend on the data and the range of ADC buffer. The bins in this example are 5 units wide, however the width can be a larger or smaller number of ADC units. In other embodiments, the bins would represent the ST deviation as a percentage heart signal amplitude where the bins would be for example, 5% wide. Further, the most negative bin (the −30 bin in this example) includes not only beats with an ST deviation of −32, −31, −30, −29 and −28, but also all beats less than −32. This would similarly be true for the largest bin.

In an embodiment, along with the histogram 750, the IMD 10, SSMD 800 or SCM 900 of FIG. 3 would measure and save an average value of heart signal amplitude (e.g., QRS amplitude or R-Wave amplitude/height) from a multiplicity of beats of the heart signal collected over the same data collection time period during which bins in the histogram 750 are incremented. It is most efficient if heart signal amplitude and ST deviation values are measured and stored in ADC units.

In one embodiment, the histogram 750 which provides the running count of beats having ST deviation values in ADC units along with the additional saved value of average heart signal amplitude in ADC units from a multiplicity of beats collected during the same data collection time period (e.g., 1-14 days) are used to calculate positive and negative excessive ST shift detection thresholds as follows:

1. The mean (line 780, or other measure of central tendency such as median, zero value or mode) and negative and positive standard deviations (lines 772 and 774) are calculated from the data of the entire histogram 750,
2. the positive ST deviation threshold in ADC units (line 784) is set as the mean plus a multiple of (for example 3) standard deviations,
3. the negative ST deviation threshold in ADC units (line 784) is set as the mean minus a multiple of (for example 3) standard deviations,
4. The positive excessive ST detection threshold is then computed as the positive ST deviation threshold computed as a percentage or fraction of the average heart signal amplitude,
5. The negative excessive ST detection threshold is then computed as the negative ST deviation threshold computed as a percentage or fraction of the average heart signal amplitude, In alternative embodiment, rather than ST deviation being used in the histogram and then later normalized to the average heart signal amplitude, the normalized ST deviation data is stored where the ST deviation of each beat collected is normalized to the heart signal amplitude of that beat and expressed as a percentage. Likewise, the histogram 750 bins are measured in percentage of corresponding heart signal amplitude instead of ADC units. This eliminates the need to normalize during calculation of excessive ST shift thresholds but is less efficient as the IMD 10 must calculate normalization for each beat analyzed.

The histogram envelope 760 is also shown and may be part of the histogram display incorporated into the ACMS Physician's Programmer 140 or the SDAPP 220 of FIG. 3. The depiction of the mean ST deviation 780 and the positive and negative standard deviations 774 and 772 respectively of the histogram data 755, is superimposed on the displayed histogram to improve quick visual assessment of the distribution.

While FIG. 18 shows the use of the mean ST deviation value as the basis for determining positive and negative detection thresholds, in embodiments the bin including the zero ADC value or median ST deviation value is used.

Figure 19:
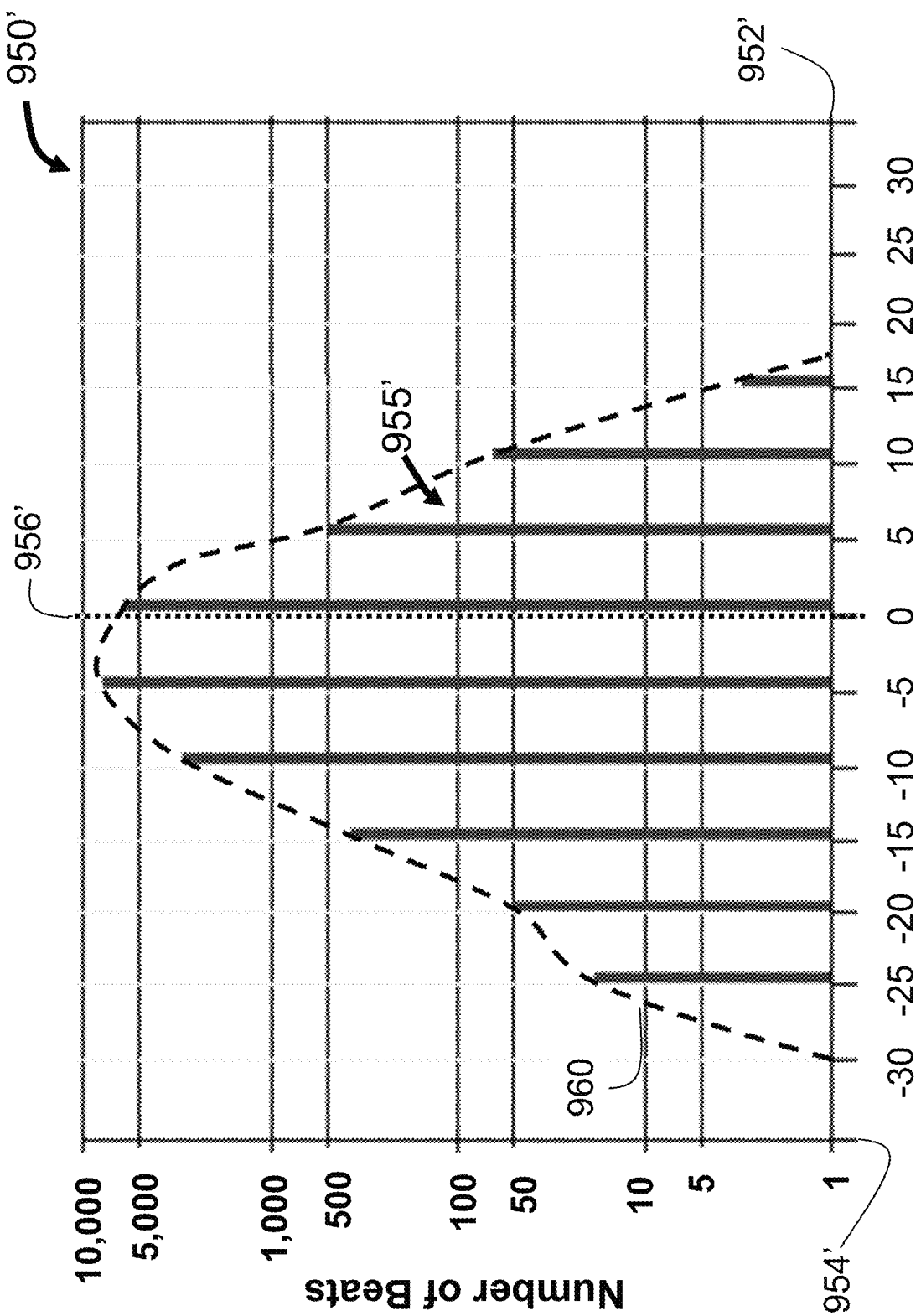
FIG. 19 shows an example of an asymmetric ST deviation histogram collected over a sufficient number of days to obtain thousands of analyzed heart beats.

FIG. 19 shows an example of an asymmetric ST deviation histogram 950' collected over a sufficient number of days to obtain a large dataset of heartbeats (e.g., thousands of analyzed heart beats). The histogram is negatively skewed and is shown as a logarithmic plot as seen in the vertical axis 954. The horizontal axis 952 shows 13 bins corresponding to 13 values of ST deviation in the arbitrary units that are produced by the Analog-to-Digital Converter (ADC units). Each bin is 5 ADC units wide. For example, the −30 bin is incremented if the ST deviation in ADC units for a beat is −32, −31, −30, −29 or −28) Similarly the 0 bin is incremented if the ST deviation in ADC units for a beat is −2, −1, 0, 1 or 2.

For many patients the ST deviation histogram 950 will not be symmetrical. In a preferred embodiment of the ACMS 100 of FIG. 3, the positive and negative ranges of a patient ST deviation are based upon variability statistics (e.g., variance, standard deviation) that are calculated separately and independently (e.g., using different data from the histograms) to derive positive and negative ischemia detection thresholds that reflect what is normal or typically for a patient's ST deviation levels.

Not to be limited by theory, using a can-to-tip vector for measuring ST levels may produce a greater amount of data and larger values and amounts of negative values of ST deviation as sub-endocardial ischemia from stenoses in the patient's coronary arteries may create ST depression even within the normal heart rate range. A negative shift in the can-to-tip vector from occlusion of a coronary artery occurs when the artery is feeding directly to the tip electrode location. Such shifts can be larger than positive shifts that occur from occlusion of a coronary artery feeding a portion of the heart muscle at some distance away from the tip electrode location.

FIGS. 20A to 20D illustrate example embodiments of the present invention for producing separate calculations of positive and negative distributions that are then used to determine positive and negative detection thresholds.

Figure 20A:
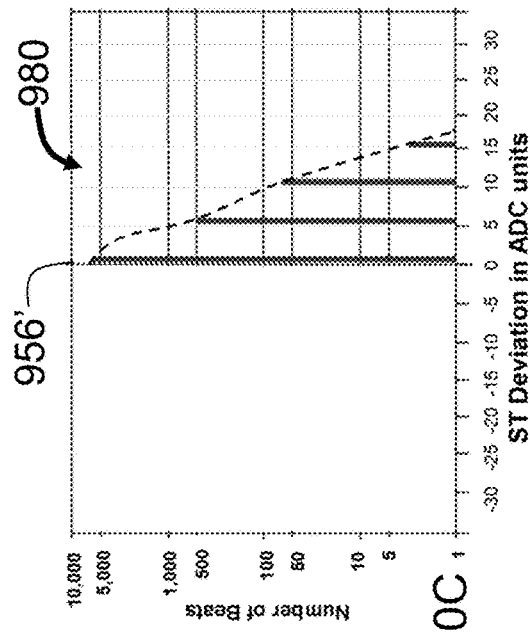
FIG. 20A shows the negative portion of the ST deviation distribution of FIG. 19.

FIG. 20A shows the negative portion 970 of the ST deviation distribution 950' of FIG. 19. In an embodiment, the standard deviation (or another statistical metric of dispersion) for this portion of the distribution 950' is created by using the distribution 970 which is then mirrored about the zero value 956' to create the resulting distribution 975 shown in FIG. 20B. The data of the histogram 975 are then analyzed to calculate a statistic which accurately reflects the negative distribution 970 of the original histogram 950'. An example of this statistic is the negative standard deviation shown as the line 972. The negative ST deviation threshold may then be calculated by performing operations upon that statistic (e.g., setting a threshold as three times (300%) of the value of 1 standard deviation) as shown by the line 974.

Figure 20C:
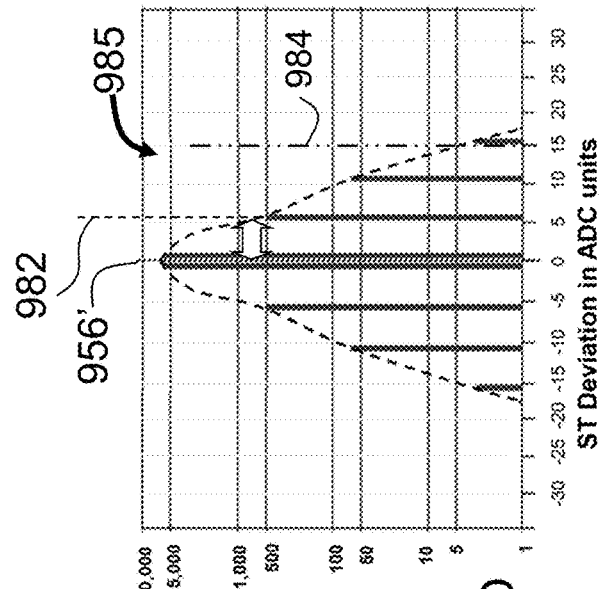
FIG. 20C shows the positive portion of the ST deviation distribution of FIG. 19.

FIG. 20C shows the positive portion 980 of the ST deviation distribution 950' of FIG. 19. To calculate the standard deviation (or other statistical metric of dispersion) for this portion of the distribution 950', the distribution 980 (or the bins included within this distribution) is mirrored about the zero value 956' creating the distribution 985 shown in FIG. 20D. These data are then analyzed to calculate a statistic which accurately reflects the positive distribution 980 of the original histogram 950'. An example of this statistic is the positive standard deviation shown as the line 982, and then used in the calculation of an associated positive excessive ST shift threshold value. For example, the positive ST deviation threshold may then be calculated by performing operations upon that statistic (e.g., setting a threshold as three times (300%) of the value of 1 standard deviation) as shown by the line 984.

While standard deviation is mentioned here any statistical measure related to the range of ST levels may be used. For example, range, probability density functions, the interquartile range (IQR), and variance are measures that may be used in the calculation of detection thresholds.

From the positive and negative ST deviation thresholds 984 and 974 respectively, the positive and negative excessive ST shift thresholds used for detecting excessive ST shift are computed by normalization of the positive and negative ST deviation thresholds 984 and 974 to a value of the average heart signal amplitude (e.g., R-height) in ADC units from the same data collection time period as the histogram data.

In a preferred embodiment the normalization expresses the positive and negative excessive ST shift thresholds as a percentage of the average heart signal amplitude and R-height is used for normalization. Thus, when the newly collected beat ST shift % expressed as a percentage of a baseline average R-height exceeds the positive excessive ST shift threshold or is more negative than the negative excessive ST shift threshold, the beat can be declared as a shifted beat.

Figure 20B:
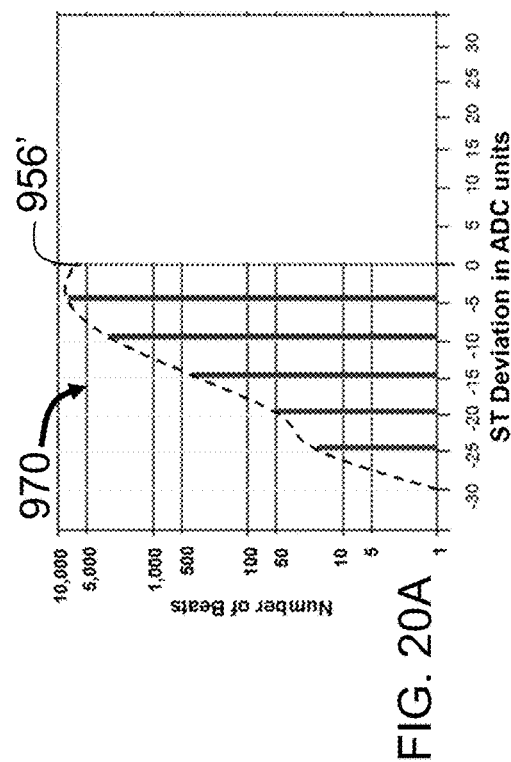
FIG. 20B shows the ST deviation distribution with the negative portion of FIG. 20A mirrored about the zero value.
Figure 20D:
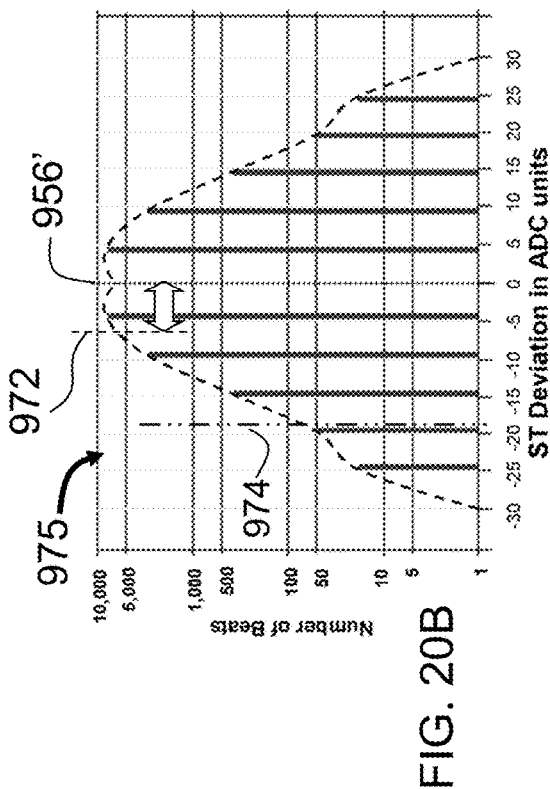
FIG. 20D shows the ST deviation distribution with the positive portion of FIG. 20C mirrored about the zero value.

Using this mirroring technique, alternate embodiments may be realized using other measures of ST levels including ST deviation in ADC units as shown in FIGS. 20A and 20B. These may include ST deviation as a voltage or ST deviation normalized to heart signal amplitude as a fraction or percentage.

In an embodiment, for cardiac data collected over a data collection time period, the processor 44 of FIG. 4 is configured to produce a histogram 950' that provides a running count of ST deviation values in ADC units also computes the average heart signal amplitude in ADC units from a multiplicity of beats. These data are used to calculate positive and negative excessive ST Shift detection thresholds as follows:
1. the positive ST deviation threshold in ADC units (line 984) is set as the mean, median, zero value or mode plus a multiple of (for example 3) standard deviations (982),
2. the negative ST deviation threshold in ADC units (line 974) is set as the mean, median, zero value or mode minus a multiple of (for example 3) standard deviations (972),
3. The positive excessive ST shift detection threshold is then computed as the positive ST deviation threshold normalized as a percentage or fraction of the average heart signal amplitude from the same data collection time period.

4. The negative excessive ST shift detection threshold is then computed as the negative ST deviation threshold normalized as a percentage or fraction of the average heart signal amplitude from the same data collection time period, In an embodiment, the ST deviation thresholds described in step 2 above are further adjusted to take into account two additional factors:

all the ST deviation histogram data upon which these initial thresholds are based is stored in bins that are, for example, 5 ADC units wide. That means there is some uncertainty in the spread estimate and needs to be considered.

From one data collection time period to the next, variation in the mean (or median) value of the ST deviation histogram shown in FIG. 19 will change. It is also envisioned that this variation may be used to adjust the ST deviation thresholds.

In one embodiment, once the positive and negative excessive ST shift detection thresholds (saved as a percentage or fraction of the average heart signal amplitude collected over the same data collection time period) are stored in the Program Parameters Memory 475 of FIG. 4, the IMD 10 (or SSMD 800 or SCM 900) would identify an excessive ST shift event as follows:

1. At selected periodic intervals, heart signal beats are analyzed to update a baseline including two primary heart signal parameters of a) average ST deviation in ADC units and b) average heart signal amplitude (e.g., QRS amplitude or R-wave amplitude/height) in ADC units
2. The IMD 10 will collect new beats for which ST deviation in ADC units will be computed and then the ST shift % for that beat will be computed as the ST shift (the change in ST deviation compared to baseline for that beat as a percentage (or fraction) of the baseline average heart signal amplitude.
3. If the ST Shift % is positive and greater than the positive excessive ST shift detection threshold stored in the Program Parameters Memory 475 or the ST Shift % is negative and more negative than the negative excessive ST shift detection threshold, then the beat is identified as Shifted.
4. If a multiplicity of shifted beats is identified over a pre-set time period, the IMD 10 will initiate a patient alert.

In a preferred embodiment, a 10 second long electrogram segment of heart signal data is collected every 30 to 90 seconds. If 6 out of 8 beats are classified as "shifted" in three successive 10 second segments, then each of these segments is classified as abnormal/shifted and a patient Emergency alarm is initiated.

In a preferred embodiment the data collection time period for each histogram is 24 hours, an average heart signal amplitude is also saved for each 24-hour period and histograms and average heart signal amplitudes are maintained in memory for a data retention time period of up to 14 days.

In an embodiment, an adjustment factor may be used for adjusting parameter value used to set the negative excessive shift thresholds. For example, the positive threshold value could be set at 3 standard deviations and the negative threshold set at 4 standard deviations below the mean, median or zero point.

In embodiments, rather than using histogram data, it is possible to store the set of raw values for ST-deviation, ST shift, ST shift %, or any other cardiac feature disclosed herein. These can be identified and grouped in relation to the corresponding heart rate ranges. Summary statistics for sensed cardiac measures can computed from either summary constructs such as histograms, clusters, or other data reduction schemes, or can be computed from individual measures which require larger memory storage. Rather than mean/median, other measures of central tendency may be used including weighted averages and other statistics that exclude or minimize the contribution of atypical or outlier data. Measures of variance may similarly be expanded from standard deviation to include any other measure that relates to spread, bias, skewness, or other metric related to the distribution or variance of the data for an individual.

Prorating for Sparse or Missing Data

In embodiments, one or more interpolation schemes may be used to provide metrics for heart rate ranges such as may occur if the recorded data of an individual patient are sparse within selected ranges. For example, data for the normal range is very likely to be sufficient for establishing ischemia detection thresholds, but the data in the elevated heart rate bin(s) may be sparse because the patient's heart did not enter those ranges during a baseline period, then the thresholds for those elevated heart rate bins at range are determined from the positive and negative standard deviations 982 and 972 of FIGS. 20B and 20D respectively (or other variance measures) for the normal heart rate bin. In embodiments several factors are taken into consideration, such as: A) the number of beats in each elevated heart bin for each day: for any day/bin with a count of less than a threshold (such as, for example, 16), consider the count to be 0; B) for days/bins where the median cannot be calculated for lack of beats in the histogram, set the median value to be the median value of the next lower heart rate bin; and, C) the granularity of the histogram bin sizes In embodiments, using these considerations, the positive threshold for an elevated heart rate bin can be set as the sum of the positive threshold for the normal heart rate bin plus the difference in the medians of the elevated heart rate bin and the normal heart rate bin plus the size of the histogram bins (such as, for example, preferably 5) converted to a % of baseline RPQ. Similarly, the negative threshold for an elevated heart rate bin is the negative threshold for the normal heart rate bin plus the difference in the medians of the elevated heart rate bin and the normal heart rate bin minus the size of the histogram bins (such as, for example, preferably 5) converted to a % of baseline RPQ.

In an embodiment, the ischemia detection threshold for a heart rate range which meets a sparseness criterion is set by calculating the variance measure that is obtained from the normal heart rate range which is offset by the difference between the median (or other measure of central tendency) of the normal heart rate range and the median of the bin for the elevated heart rate range. Alternatively, the variance of the measure for the normal heart rate range can be multiplied by a constant that is calculated based upon population normative ranges for the elevated or high ranges. Alternatively, the threshold may be set as the difference between the threshold for the normal heart rate range and the range of an elevated or high heart rate range based upon the number of intervening bins. In other words, the threshold can be interpolated using threshold level above and below a missing heart rate bin. Elevated range thresholds could also be determined by an adjustment factor. For example, the thresholds could increase for positive shifts and decrease by negative shift by a preset percentage as one moves to successive elevated heart rate ranges.

In an embodiment, the Physician's programmer is configured to display the histogram data and statistics calculated for the positive and negative distributions as summary statistics, graphically, or as a combination so that a user can manually set or adjust the excessive thresholds. In embodiments, the programmer or IMD can exclude portions of reference data collected during a reference period automatically or under user guidance. For example, a visual review of the data causes a doctor to believe the patient had low quality or problematic data during 1 day of the 14 days. Alternatively, the data may appear strange for the first couple of days after surgery and then become normal as the electrode-tissue connection became more stable. In these cases the user may select only data they deem appropriate to e included in the histogram data and/or used to set thresholds. Alternatively, parameters may also determine a scheduled interval during which the reference period will be established. Parameters may also determine the reference period used to set the thresholds does not begin until a selected number of hours (e.g. 4-24) or days (e.g., 1-3) after the implant occurred.

In an embodiment, a recovery alarm setting may be set in the IMD or Programmer. For example, if a patient has a period of elevated heart rate (e.g., due to exercise), after the heart rate returns to the resting range the patient's ST-levels may remain elevated slightly longer before recovering to normal range. Although at different heart rate ranges there are different excessive ST-deviation thresholds, this will not address this scenario well since the heart rate has changed. The recovery alarm setting may be set so that if the Guardian detects an excessive ST deviation, and if the heart rate was elevated in the last 8 segments (e.g., 4-12 minutes), then instead of an Emergency Alarm, the device may only provide a See Doctor alert or may not notify the patient until more data is collected and assessed.

In an embodiment, the IMD 10 is programmed to initially or periodically assess the histogram data to determine the detection thresholds without the need to upload the data to a physician programmer. Configuring the IMD to adjust detection thresholds by using calculations every 30 to 180 days may be implemented on a scheduled or periodic basis and may be selectable or adjustable by a doctor. The adjustment may be carried out as an Autopick functions using at least some of the steps described in methods shown FIGS. 20e and 20f. When the IMD 10 is configured to automatically perform calculations and set the detection thresholds then additional quality checks may be performed. For example, one quality check may assess if the positive or negative threshold value is below or exceeds an expected range. If the quality check fails to meet at least one defined quality criterion then an action may contingently occur as part of step 881, such as providing notification to the patient or doctor. Additionally, if the absolute values for positive and negative thresholds are above a selected amount then this may also cause an operation to occur since this may indicate the data should be reviewed before being used. Data from the IMD 10 autopick function may also be transmitted through the EXD 120 to a remote computed for automated or human quality checks before the thresholds are updated in the IMD 10, In an embodiment, the system is configured to calculate ST deviation for a set of heartbeats (e.g., hundreds/thousands of beats) over hours, days or weeks to provide data for calculating thresholds defining the normal patient heart signal. The set of heartbeats should be a large enough sample so that only a significant acute event like a total occlusion of a coronary artery will produce sufficient changes that exceed the calculated measures for excessive ST thresholds. The methods for establishing thresholds and enabling a detection algorithm for identifying abnormal/excessive ST changes that are used to detect an acute myocardial infarction (heart attack) can be realized in the following example embodiments.

Method 1 uses the Physician's Programmer 140 of FIG. 3 in conjunction with a Heart Signal Capture and Event Detection (HSCED) device that can be the IMD 10, SSMD 800 or SCM 900 of FIG. 3, and includes the steps of:

Step 1: Placing at least 2 electrodes in contact with a portion of the patient in a position to sense electrical signals from heart. Such positions include electrodes that are: a) in contact with the heart including those that are part of a pacemaker or ICD lead; b) on or including the surface of an implantable device, c) electrodes on the patient's skin and d) implanted subcutaneously, for example the can of an IMD 10 or SCM 900 or an electrode on a lead attached an IMD 10 or SCM 900.

Step 2: Connecting the electrodes with conducting means to the HSCED device.

Step 3: Enabling the HSCED to collect heart signal data for a multiplicity of beats and calculate the measurement of the ST level, ST deviation, ST shift, or ST shift % of each beat. This data collection may occur until a pre-set or programmable number of beats or a pre-set or variable interval occurs. For example, the HSCED could operate in a collection mode until it had a total of a pre-selected number of heart beats such one thousand beats before triggering additional operations such as computing thresholds or storing data in a particular manner. In an alternative embodiment, data are collected for a data collection time period of 24 hours, after which, the data are saved and a new 24-hour data collection time period is started. In this second case, the data could be retained in memory for a second longer data retention time period. For example, the 24-hour collections could be saved for 14 days before they are overwritten. Data can be saved as individual numbers or in a histogram or other appropriate format.

Step 4: After a selected number of beats or time has elapsed, the HSCED would upload the saved data to the Physician's Programmer 140 of FIG. 3. This would ideally be done during incision check 7-14 days after data collection from the HSCED is initiated or at any time after enough data has been collected.

Step 5: The Physician's Programmer 140 would include statistical processing algorithms to calculate positive and/or negative excessive ST shift detection thresholds from the uploaded data for example using the embodiments in the descriptions of FIGS. 18 through 20D. It is envisioned that this would be done at least for at those data where the R-R interval of the beats with ST deviation data in the histograms correspond to a normal heart rate range for the patient. Ideally, it would be done for one or more elevated heart rate ranges as well.

Step 6: The calculated positive and negative excessive ST shift thresholds would then be downloaded back to the HSCED.

Step 7: The HSCED would then be activated to detect excessive ST shift using the downloaded thresholds as described herein.

Method 2—provides the calculation of detection thresholds within a HSCED that can be the IMD 10, SSMD 800 or SCM 900 of FIG. 3, and substitutes Steps 4 and higher as follows:

Step 4: After a sufficient number of beats are collected or time has elapsed, the HSCED processes the data collected to calculate positive and/or negative excessive ST shift detection thresholds from the uploaded data. It is envisioned that this would be done at least for at those data where the R-R interval of the beats correspond to a normal heart rate range for the patient. Ideally, it would be done for one or more elevated heart rate ranges as well.

Step 5: The calculated positive and negative thresholds would then be saved in memory of the HSCED for use in detection of excessive ST shifts.

The HSCED would then be activated to detect excessive ST shift using the downloaded thresholds as described herein.

The techniques described in FIG. 18, 19 or 20A-D are applicable to either Method 1 or Method 2. Method 2 may also include a verification step between steps 5 and 6 where wireless connectivity of the HSCED would be used to allow the information related to the calculation of the thresholds to be verified externally by humans or other computer systems.

All of the techniques described with respect to the descriptions of FIGS. 18 through 20D require a calculation of the standard deviation of the distribution stored in histogram format. An example of the formula used to calculate one standard deviation (sigma) including using samples from a histogram is:

$$\sqrt{\frac{n \times \sum x^2 - (\sum x)^2}{n \times (n-1)}}$$

where n is the total number of samples in each histogram bin and the x's are the values of the samples in the respective histogram bin.

Figure 20E:
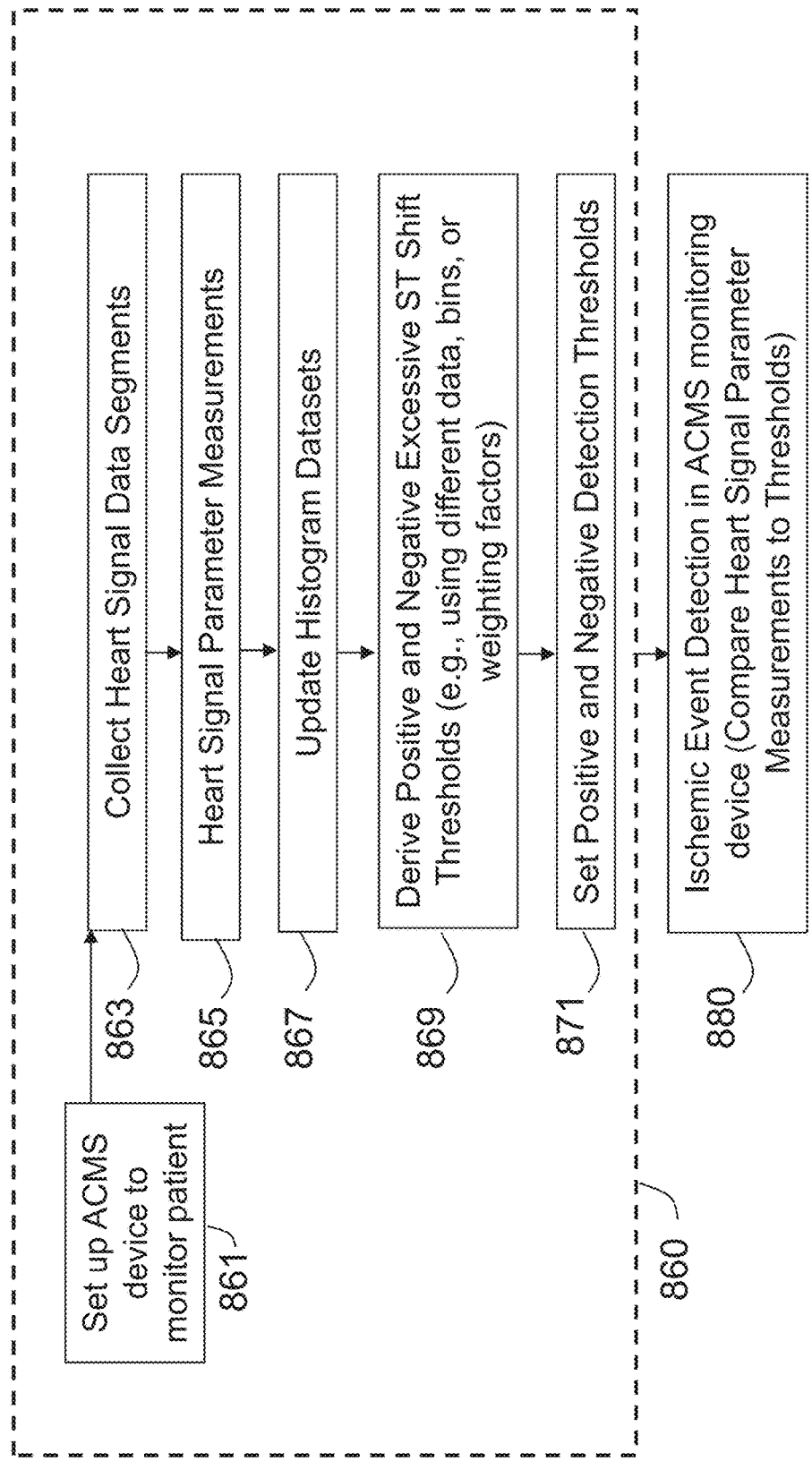
FIG. 20E shows steps for creating and using positive and negative thresholds such as ST thresholds.

FIG. 20E shows the steps of a method for detecting potential ACS events using positive and negative excessive ST shift detection thresholds which are, in some embodiments, calculated in a manner that accounts for asymmetrical distributions of a cardiac measure such as ST-Level, ST deviation, ST shift, or ST shift %.

In an embodiment, a method for performing a contingent operation responsive to detection of excessive ST shift from heart signal data of a patient comprises a first step 861 of setting up an ACMS device such as an IMD 10 to monitor cardiac activity of a patient. Step 861 can include attaching electrodes connected to electronic circuitry of device that is devoid of circuitry adapted to deliver electrical energy through the electrodes to the patient's heart, the circuitry adapted to process the heart signal. In the next step 863 samples of cardiac data are sensed by a device and this may occur by sensing heart signal data segments, e.g., electrogram segments, at predefined intervals such as collecting 10 seconds of data every 90 seconds. Accordingly step 863 includes operating the device to provide sensing of the heart signal and this is followed by measuring heart signal parameter measurements of the collected beats in step 865. Step 865 can provide for measuring each beat of a multiplicity of beats from a PQRST representation of said heart signal during a data collection time period, the ST deviation being substantially an ST segment average voltage minus a PQ segment average voltage within each of said beats. In a preferred embodiment, this would include measurements of RR interval, ST deviation and heart signal amplitude (e.g., R wave height) for each beat in one or more heart signal data segments. In the next step 867, the heart signal parameter measurements are used to update histogram and baseline datasets according to a protocol that may include checking to ensure that the recorded data meet certain characteristics such as being of good quality and containing a selected range of heartbeats that do not suffer rate, rhythm, or morphology problems that can make measurement difficult. Step 867 can include creating and storing in a processor at least one histogram comprising a set of bins, each of said bins being associated with an ST deviation range, wherein each bin contains a running count of the number of beats whose ST deviation is measured to be within the ST deviation range associated with the bin during one data collection time period. Step 867 may also, at a pre-defined interval, save one or more heart signal data segments in baseline memory and use the heart signal parameter measurements from the beats in those segments in the production of average baseline values of one or more heart signal parameters.

In step 869 data which is stored in histograms along with other stored heart signal parameter data is used to create patient-specific detection thresholds for one or more heart signal parameters. When this is done for an ST measurement, the method may be improved by calculating the thresholds based upon subsets of the data related to positive and negative distributions of ST levels e.g., ST deviation. For example, in an embodiment step 869 provides for operating a processor to only calculate either a positive or negative excessive ST deviation threshold using a first set of bins from said at least one histogram and separately operating a processor to calculate only said positive or negative excessive ST deviation threshold which has not been calculated using the first set of bins by using a second set of bins of said at least one histogram. The step may include operating a processor to calculate a negative excessive ST shift threshold using a second set of bins which are at least partially unique from the bins used in step of calculating the positive thresholds of said at least one histogram. The positive ST deviation thresholds are then used to calculate ST shift thresholds (which may be normalized to obtain ST Shift % thresholds). The operations required to determine the thresholds can be accomplished in the monitoring device or using a Physician's Programmer which has accessed the data of the monitoring device and downloaded the thresholds back to the monitoring device. After thresholds, such as positive and negative excessive ST shift thresholds, have been derived and set in the monitoring device in step 871, in step 880, monitoring for detection of defined cardiac events such as potential ACS events begins. The prior art '023 patent provides in FIG. 5 an embodiment of such an ongoing detection algorithm. An improved embodiment is shown in FIG. 20F.

Figure 20F:
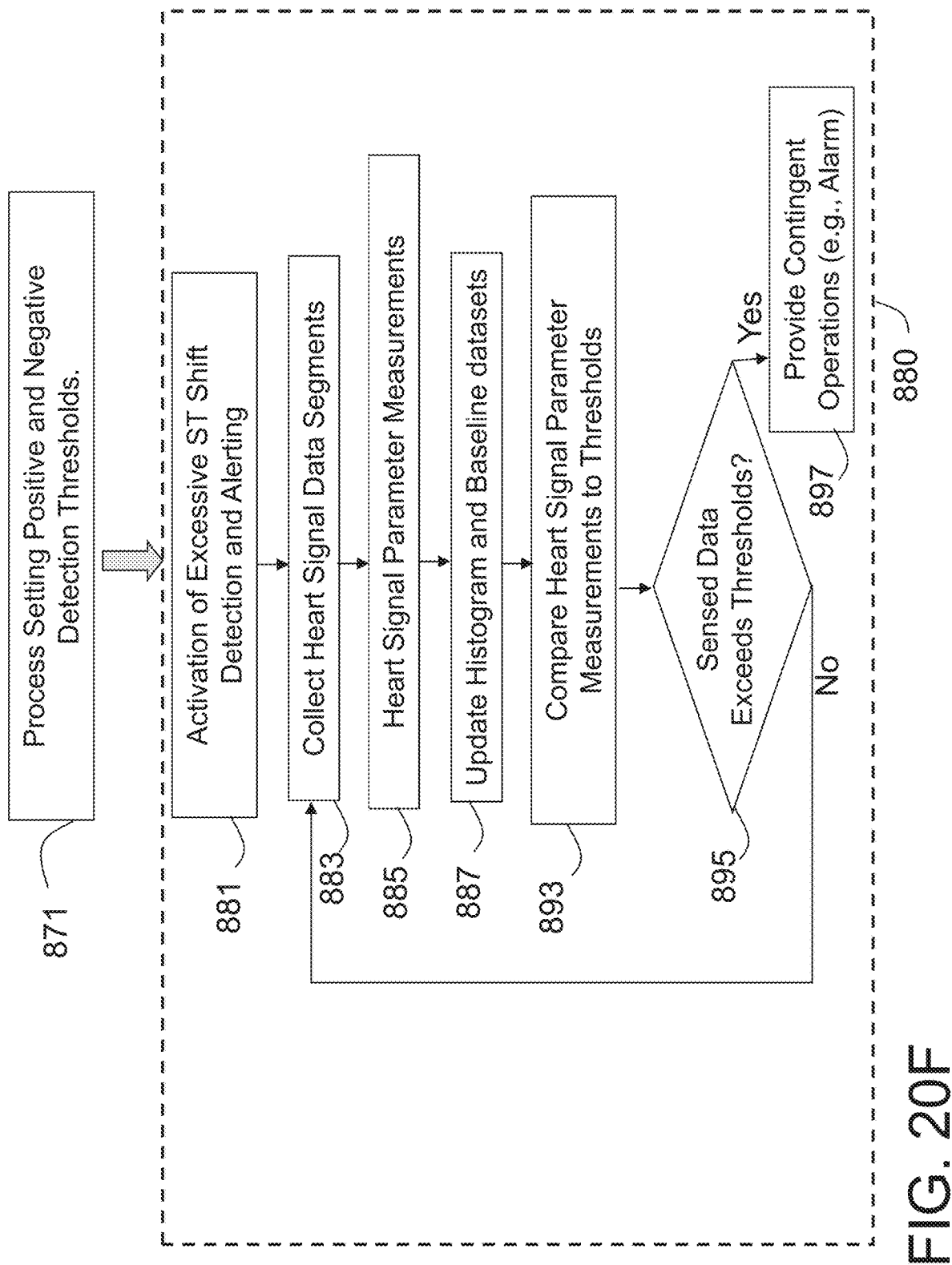
FIG. 20F shows steps for assessing incoming cardiac data according to detection rules applied to thresholds and for performing a contingent operation if at least one threshold criterion is exceeded.

FIG. 20F illustrates an embodiment which includes after setting positive and negative excessive ST shift thresholds in the monitoring device in step 860 of FIG. 20E, in step 881 the monitoring device is activated to begin the detection and associated patient alerting of excessive ST shift.

In step 883, heart signal segments with a multiplicity of beats in each segment are collected by the heart monitoring device.

In step 885, the beats in each segment are processed to calculate one or more heart signal parameter measurements such as ST data. In a preferred embodiment, this would include measurements of RR interval, ST deviation and heart signal amplitude (e.g., R-height) for each beat in one or more heart signal data segments.

In step 887, the heart signal parameter measurements are used to update one or more histograms, save to memory one or more baseline segments at a pre-set interval, and update the value of average composite baseline data for one or more heart signal parameters used for comparison with newly collected heart signal data to detect excessive ST shift or other heart signal abnormalities. Examples of measuring and storing heart signal parameters is incorporated by reference are seen in the prior art.

In step 893 one or more heart signal parameter measurements or changes in one or more heart signal parameters from baseline (which may be normalized) are compared to pre-set detection thresholds by operating at least one processor such as the processor of the IMD. For example, ST shift % (the change in ST deviation from the average baseline ST deviation normalized to the baseline R-height or R-height of other reference data such as obtained in the prior hour) can be compared to the positive or negative excessive ST shift thresholds (e.g., ST Shift % thresholds).

If in step 895 the heart signal parameter comparison indicates thresholds have been exceeded according to a threshold rule such as, 6 out of 8 beats in three successive segments exceed either the positive or negative excessive ST shift threshold, then a contingent operation in step 897 would occur such as alerting the patient. The prior art techniques for patient alerting associated with two or more levels of severity of the detected event may be used here. In embodiments, contingent operations also include storing sensed data using a protocol defined for a detected cardiac event type or changing the monitoring protocol so that data are collected more frequently or continuously. Another example embodiment compares the percentage of beats over a pre-set time period with R-R intervals in one or more of elevated heart rate ranges to a threshold of 50% that could be indicate of beta blocker compliance or incorrect dosing. Another example embodiment compares the percentage of cardiac data segments over a pre-set time period with R-R intervals that cause the segment to be classified at least one elevated heart rate range, and if at least a selected threshold of segments (e.g., 50%) are classified as elevated a beta blocker compliance or incorrect dosing contingent operation occurs 897. Alternatively, if the sensed data are determined to not exceed defined thresholds, then the routine returns to step 883 and additional segments of cardiac data are collected.

At various times the method may include repeating steps of FIG. 20E. Once positive and negative excessive ST shift thresholds are set in step 871, steps 869 and 871 may be skipped for a preset period of time. It is highly desirable to repeat the steps of FIG. 20E at a pre-set interval such as 6 months as well as following and event that might change the patient's coronary blood including an ACS event that could reduce the blood flow in one or more coronary artery or bypass graft or a PCI or CABG procedure that could increase the flow in one or more coronary arteries. The re-working of excessive ST shift thresholds may require a programming session if the processing is done by the Physician's Programmer 140 of FIG. 3 or may be automatically performed within the IMD 10 of FIG. 3.

In yet another alternative embodiment, a method for actuating an alarm responsive to detection of an abnormal change in a measure of ST level of a heart signal of a patient includes measuring for each beat of a multiplicity of beats from a PQRST representation of a heart signal during a data collection time period, an ST level measure that is reflective of the ST segment of the beats. The ST level may be selected from the group including: a) ST deviation being substantially an ST segment average level minus a PQ segment average level within each of said beats; b) average ST voltage or C) average ST signal amplitude measured in ADC units.

The method includes operating a first processor for creating and storing at least one histogram dataset comprising a set of bins, each of said bins being associated with an ST level range, wherein each bin contains a running count of the number of beats whose ST level is measured to be within the ST level range associated with the bin during one data collection time period. Additionally, the method includes operating a first or second processor for calculating a first threshold which is either a positive or negative excessive threshold using a selected set of bins of said at least one histogram and also operating said first or second processor to calculate only said positive or negative excessive threshold using bins of at least the one histogram which were not selected and or calculated upon to calculate the first threshold. The method also includes operating said first processor to compare the ST level measure of at least one of the multiplicity of beats to at least one of said positive or negative thresholds to detect potential ACS events. ACS event alerting can occur if said comparison indicates the ST level measure of at least one set of the multiplicity of beats exceeds at least one of said positive or negative thresholds. In a preferred embodiment, the method of may include a step where the ST level measure is used to calculate a measure of ST shift % and the thresholds are positive and negative excessive ST shift thresholds. In an embodiment the first processor is in the IMD 10 and the second processor is in the Physician's programmer. In an alternative embodiment the first processor and second processor are both in the IMD, or both external to the IMD, or the second processor is in the IMD 10 and the first processor is in the Physician's programmer. In an alternative embodiment, the first and second processor are in a set which includes at least 2 processors. In alternative embodiments one of at least 2 processors is in a system component such as a smart device 225 or in a computer of an external support system 240.

Differentiating Between Demand and Supply Ischemia

Figure 21B:
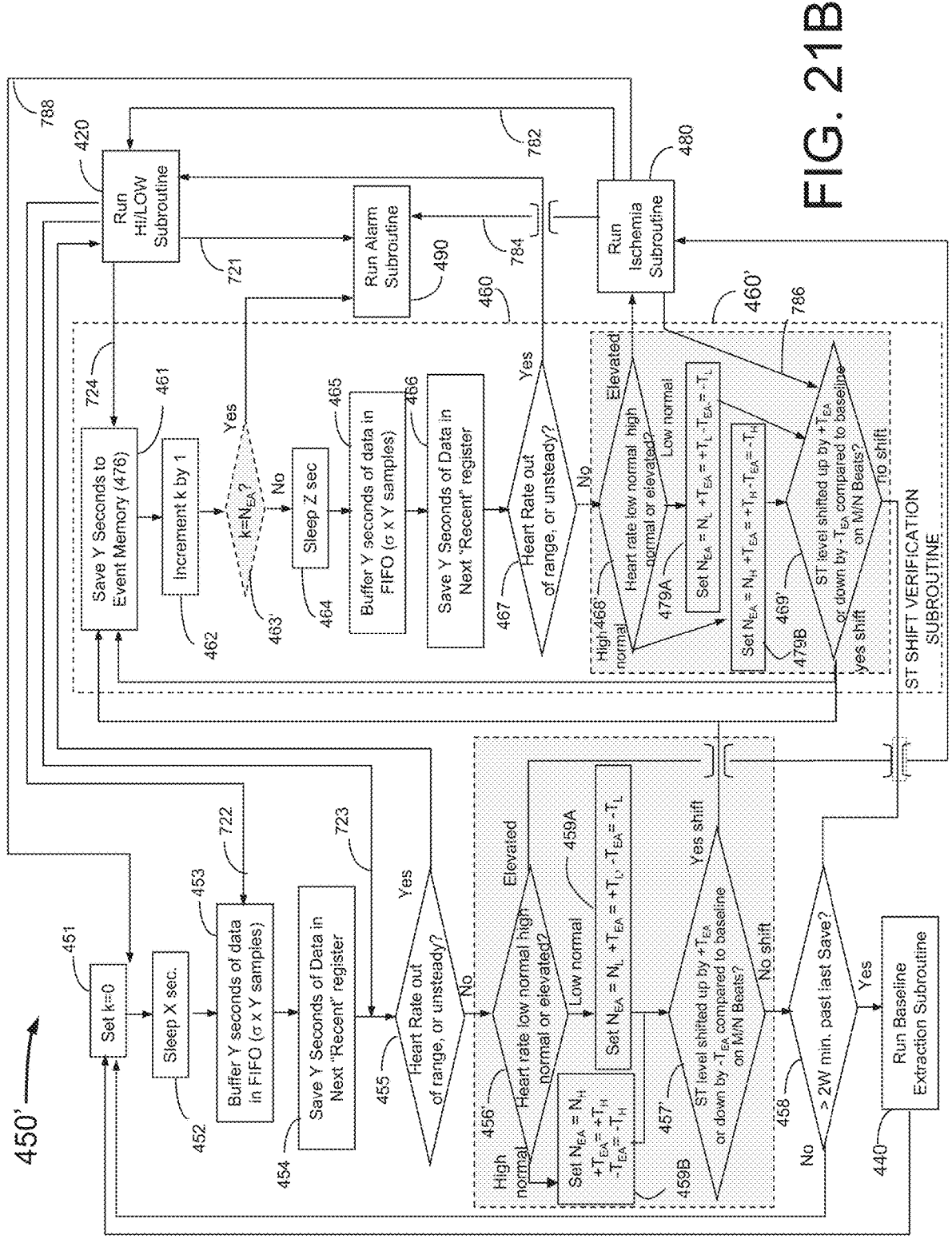
FIG. 21B shows a block diagram of the process used to enhance accuracy of ST shift-based emergency alarms.

FIGS. 21A and 21B are used to illustrate embodiments of the present invention that help differentiate between: a) ST changes that likely reflect demand-ischemia that may occur in an upper portion of a normal heart rate range; and, b) ST changes that are likely due to supply-side ischemia from a coronary occlusion i.e. a potential heart attack.

In embodiments, enhancements are provided to improve the process 450 of the prior art shown in FIG. 21A which appears as FIG. 5 of U.S. Pat. No. 6,609,023, incorporated herein by reference. FIG. 21A shows a process 450 for identifying excessive ST shift events by detecting 3 successive events that meet the criteria for detection of step 469. Upon 3 such events, step 463 triggers alarm subroutine 490.

FIG. 21B shows a block diagram of the process 450' which provides the advantage of being an improvement to the prior art, and which improves the accuracy of excessive ST shift based emergency alarms for alerting to potential ACS events. Selected improvements over the prior art (of FIG. 21A) are shown in the shaded boxes of FIG. 21b and include steps 456', 459A, 459B, 457', 463' and 469'.

In an embodiment, step 456' replaces step 456 of FIG. 21A that differentiates the average heart rate a sample of data lasting "Y" seconds into two categories of heart rate ranges (normal or elevated) by identifying whether the heart rate/

RR interval associated with the "Y" seconds of electrogram data is in one of three categories (Low-normal, High-normal, or Elevated).

If the data is classified as Elevated, then step 456' does the same thing as step 456 of FIG. 21A advancing to the ischemia subroutine step 480. Alternatively, if the data is classified as low-normal, then step 456' advances to step 459A and the number of successive segments that are classified as "shifted" which are required to trigger an Emergency alarm $N_{EA}$ is set to the $N_L$ value. Additionally, the positive threshold for detecting excessive ST shifts for an emergency alarm ("+$T_{EA}$") is set to the positive threshold value ("+$T_L$") and the negative threshold ("−$T_{EA}$") is set to the negative threshold value −$T_L$. If the data is classified as High-normal, then step 456' advances to step 459B where $N_{EA}$ is set to the value $N_H$ and positive threshold for detecting excessive ST shifts for an emergency alarm +$T_{EA}$ is set to the value +$T_H$ and the negative threshold −$T_{EA}$ is set to the value −$T_H$.

The provision of a variable counter threshold $N_{EA}$ into the disclosed method allows different values that are set in steps 459A or 459B depending on whether the average heart rate for the "Y" seconds of data is Low-normal or High-normal. For example, $N_L$ could be 3, which is the same number of successive segments used in FIG. 21A. However, in embodiments $N_H$ is adjusted to be higher than $N_L$ (e.g., 5 or more). This can provide an advantage that the system is less likely to trigger an Emergency alarm for ST changes caused by demand ischemia.

In the disclosed method, steps 459A and 459B advance to step 457' where a baseline ST segment level is compared to the ST level seen for "N" beats in the "Y" seconds of data saved in step 454. If the "M out of N" beats are shifted up by more than the positive threshold for initiating an Emergency alarm +$T_{EA}$ (or down by more than the negative threshold −$T_{EA}$) then the process advances to step 461 of the ST shift verification subroutine 460' where the Y seconds are saved to event memory and the successive event and "counter k" is incremented by one in step 462 and then compared to $N_{EA}$ in step 463' which differs from step 463 in FIG. 21A where k is compared to the set value of 3.

Step 463' will advance to the Alarm subroutine 490 if k=−$N_{EA}$. If not, it will continue as in the prior art routine 460 of FIG. 21A by sleeping Z seconds in step 464, collecting "Y" seconds of data in steps 465 and 466, screening for abnormal heart rates in step 467 and the once again looking to see if the average heart rate is Low-normal, High-normal or Elevated in step 468' which is the same as step 456'.

Step 468' replaces step 468 of FIG. 21A that differentiates the average heart rate of the Y seconds into two categories (Normal or Elevated) by identifying whether the average heart rate/RR interval associated with the Y seconds of electrogram data is in one of three categories (Low-normal, High-normal or Elevated).

If Elevated, the step 468' does the same thing as step 468 of FIG. 21A advancing to the ischemia subroutine step 480.

If Low-normal, step 468' advances to step 479A and the number of successive segments shifted needed to trigger an emergency alarm $N_{EA}$ is set to the value $N_L$ and the positive threshold for detecting excessive ST shifts for an emergency alarm +$T_{EA}$ is set to the value +$T_L$ and the negative threshold −$T_{EA}$ is set to the value −$T_L$.

If High-normal step 468' advances to step 479B where $N_{EA}$ is set to the value $N_H$ and positive threshold for detecting excessive ST shifts for an Emergency alarm +$T_{EA}$ is set to the value +$T_H$ and the negative threshold −$T_{EA}$ is set to the value −$T_H$.

Having a variable counter threshold $N_{EA}$ allows different values that are set in steps 479A or 479B depending on whether the average heart rate for the Y seconds of data is low-normal or High-normal. For example, $N_L$ could be 3 the same number of successive segments used in FIG. 21A. It is envisioned that $N_H$ would be higher than $N_L$ (e.g., 5 or more). In this way the system would be less likely to trigger an emergency alarm for ST changes caused by demand ischemia.

Steps 479A and 479B advance to step 469' where a baseline ST wave level is compared to the ST level seen on N beats in the Y seconds of data saved in step 465. If the M out of N beats are shifted by more than the positive threshold for initiating an emergency alarm +$T_{EA}$ or by more than the negative threshold −$T_{EA}$ the process advances to step 461 of the ST shift verification subroutine 460' where the Y seconds are saved to event memory and the successive event counter k is incremented by one in step 462 and then compared to $N_{EA}$ in step 463' which differs from step 463 in FIG. 21A where k is compared to the set value of 3.

Step 463' will advance to the Alarm subroutine 490 if k=$N_{EA}$. If not it will continue as in the prior art routine 460 of FIG. 21A by sleeping Z seconds in step 464, collecting Y seconds of data in steps 465 and 466, screening for abnormal heart rates in step 467 and the once again looking to see if the average heart rate is low-normal, High-normal or elevated in step 468' which is the same as step 456'.

Having different excessive ST shift detection thresholds depending on whether the heart rate is Low-normal or High-normal would improve the performance of the ACMS 100 of FIG. 3 to differentiate between transmural ischemia created by a total coronary occlusion and sub-endocardial demand ischemia due to heart rates in the upper range of Normal.

Prior art systems describe the use of a multiplicity of histograms associated with a data collection time period each one associated with a different heart rate/RR interval range. While the prior art describes use of a normal range and multiple elevated ranges, the present invention process shown in FIG. 21B envisions using two normal ranges (Low-normal and High-normal). Each would have a histogram so that the thresholds selected based on these histograms would be better suited to avoid false detections compared to a single Normal range. In embodiments, instead of using Low-normal and High-normal ranges, a first histogram for the entire Normal range plus a second one just for High-normal could also function. In this case, additional processing could be applied if the Y seconds have an average heart rate in the High-normal range to double check that the event is not a result of demand ischemia. This processing could be a follow-on comparison to the High-normal thresholds or an increase in $N_{EA}$.

In embodiments, use of both positive and negative thresholds for High-normal+$T_H$ is not needed so that only a separate negative threshold −$T_H$ would be used. Positive excessive ST shift detection thresholds would have one for the entire normal range.

In embodiments, to reduce the likelihood of repeating false alarms in the upper range of normal heart rates or for cases where the patient's heart rate is going back and forth from the normal to first elevated ranges one could either adjust down the upper limit for the normal heart rate range or increase the number of consecutive segments needed to alarm. For example, if the number is 3, increasing it to 5, 6, or 7 that is set by the ACMS Physician's Programmer 140 of FIG. 3 for specific cases where the patient has demand ischemia related false positive events. It might be adjusted for positive and negative shift events or only for positive or only for negative.

While the embodiments described herein have been directed at a stand-alone monitoring device, all of the capabilities are envisioned for use in therapeutic implanted medical devices such as pacemakers, cardioverters, ICDs and drug pumps and many of the features including those related to heart rate monitoring would be applicable to loop recorders, Holter monitors and other heart rate monitoring devices.

The processes and methods disclosed may be implemented with less or more steps than are shown, with steps being omitted or repeated in some embodiments. Steps from one process may be included in other methods that have been disclosed and steps from one figure may be introduced to steps shown in a different figure.

The modules, hardware, and software components that have been disclosed may be realized partially or fully within the devices shown in the illustrated embodiments or in alternative manners and are understood to be shared resources. For example, signal processing or event detection that is disclosed as occurring in the IMD may also occur in the EXD or may occur in both devices. Functionality, electronics, software and features disclosed for the EXD 120 may be realized in a different component of the system such as, for example, the Smart Device 225 or Physician programmer.

In summary and in operation, the system (10, 140, 120, 225) above described is generally directed to a system for monitoring a patient's heart rate and alerting the patient of an abnormal condition which is indicative of either a patient's beta blocker non-compliance with a prescribed treatment or improper beta blocker dosing. The system 10,140,120,225 includes at least two electrodes 14,18 which are implanted to sense electrical signals from the patient's heart. Electronic circuitry is coupled to the electrodes 14,18 for sensing and electrically operating on the sensed electrical signals for providing operational electronic signals. The electronic circuitry does not have circuitry to deliver electrical energy to the heart of the patient but simply senses the electrical signals emanating from the heart.

A first processor 44 within an implanted device 10 or alternatively within a Physicians Programmer 140 (as shown in FIG. 3) calculates and permits a user to adjust and select heart rate parameters including (a) at least a normal heart rate range having an upper limit 606 (shown in FIG. 16C), (b) a high heart rate lower threshold 610 for detecting tachycardia, and (c) an elevated heart rate range 620 that lies between the normal heart range upper limit 606 and the high heart rate lower limit 610.

A second processor either within the implanted device 10, or alternatively within the Physicians Programmer 140 is in communication with the electronic circuitry for computing, calculating and storing the operational electronic signals. The second processor is configured to compute an average heart rate of the patient during some pre-programmed time period for a multiplicity of heart beats, with the second processor being in communication with the first processor for storing the heart rate parameters which are downloaded from the first processor.

An external alarm device 120 (shown in FIG. 3) is in communication with the Physicians programmer 140 and the implanted medical device 10 and includes a patient alerting mechanism which may be for example a vibrator 139 which may be within the external alarm device 120 as shown in FIG. 3 or the vibrator 25 may be within the implanted medical device 10 as shown in FIG. 4. Alerting or alarm signals can be transmitted to smart devices 225 through a transceiver 147 in communication with either the processor 130 (shown in FIG. 3) in the external device 120 or the processor 44 in the implanted medical device 10 (shown in FIG. 4). The resulting alert signal may be an audio signal, a vibration signal or a visual signal.

In any event when the first processor is in the implanted medical device 10 or the external alarm device 120, the patient can be alerted in accordance with an alerting protocol when the computed average of the heart rate for at least a portion of the number of heart beats some pre-programmed time period is within the elevated heart range 620. The second processor, whether in the Physicians Programmer 140 or in the implanted medical device 10 is further configured to evaluate sensed data and (a) detect excessive ST shifts in steps 881, 883, 885, 887, and 893 shown in FIG. 20F as a function of the normal heart rate range 602, and also (b) detect and alert the patient in step 897 of beta-blocker non-compliance or improper beta blocker dosing in response to detection of a patient's heart rate that meets at least one beta-blocker non-compliance detection criterion. In embodiments, the alert is designed to inform the user specifically about detection of cardiac activity reflective of beta blocker non-compliance or improper beta blocker dosing. This may occur using a text or graphical message, sound, vibration, or combination of alerting signals that is provided to alert about potential beta-blocker non-compliance.

The disclosed methods may be operated as steps which occur in isolation, or which are repeated, or omitted, or occur in a different order without departing from the intended invention. Additionally, it is understood that steps disclosed in one figure may be combined with steps in another figure (e.g. a first set of steps may occur before a second set of steps).

All heading and section labels have been provided to facilitate readability and are not meant to limit the disclosed invention in any manner.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A system for monitoring a patient's heart rate and alerting the patient of an abnormal condition indicative of patient beta blocker non-compliance or improper beta blocker dosing, comprising:
   at least two implanted electrodes adapted to sense electrical signals from the heart of the patient;
   electronic circuitry devoid of circuitry adapted to deliver electrical energy through the electrodes to the patient's heart coupled to said at least two electrodes for sensing and electronically operating on said sensed electrical signals to provide operational electronic signals;
   a first processor configured for calculating and allowing a user to adjust and select heart rate related parameters including at least: (1) a normal heart rate range having an upper limit; (2) a high heart rate lower threshold for detecting tachycardia; and (3) an elevated heart rate range that lies between the normal heart rate range upper limit and the high heart rate lower threshold, and,
   a second processor in communication with said electronic circuitry for computing and storing said operational electronic signals, said processor adapted to compute an average heart rate of the patient during a pre-programmed time period for a multiplicity of heart beats, said second processor configured for communication with said first processor, said second processor further adapted to store the heart rate related parameters downloaded from said first processor, and, a patient alerting mechanism in communication with said second processor configured for automatically alerting the patient according to an alerting protocol and devoid of any input by the patient when the computed average heart rate for a portion of the multiplicity of heart beats during the pre-programmed time period is within the elevated heart rate range, said second processor being further configured to responsively (a) detect excessive ST shifts as a function of said heart rate normal range, and (b) alert the patient of beta blocker non-compliance or improper beta blocker dosing following detection of a patient's heart rate meeting at least one beta blocker non-compliance detection criterion for the pre-programmed time period, said pre-programmed time period being a prolonged time period defined by the at least one beta blocker non-compliance detection criterion to specifically detect cardiac activity reflective of beta blocker non-compliance or improper beta blocker dosing, said alert informing the user specifically about detection of cardiac activity reflective of beta blocker non-compliance or improper beta blocker dosing.

2. The system of claim 1, wherein the at least one beta blocker non-compliance detection criterion is that the heart rate has remained in the elevated heart range for at least a selected time interval and for at least a defined proportion of electrogram segments or heartbeats.

3. The system of claim 2, wherein said beta blocker non-compliance criterion is that the heart rate remains in the elevated heart range within said selected time interval for at least 90% of electrogram segments or heartbeats.

4. The system of claim 2, wherein said beta blocker non-compliance criterion is that the heart rate remains in the elevated heart range within said selected time interval for at least 50% of electrogram segments or heartbeats.

5. The system of claim 2, wherein said beta blocker non-compliance criterion is that the heart rate remains in the elevated heart range within said selected time interval for a time interval that is greater than three hours.

6. The system of claim 2, wherein said beta blocker non-compliance criterion is that the heart rate remains in the elevated heart range for at least said selected time interval for at least a defined proportion of electrogram segments, where at least one of the selected time interval value and proportion value is selected by a physician by operating the first processor which is in a Physician's programmer.

7. The system of claim 1, wherein the at least one beta blocker non-compliance detection criterion is only applied to data that is sensed when a set of accelerometer activity measurements are assessed by the second processor as being below a value defined by an exercise threshold, whereby it is likely the patient is not exercising.

8. The system as recited in claim 1 wherein the patient alerting mechanism includes a set of protocols defining at least two different alerts associated with at least two levels of urgency, the urgency related to medical risk for the patient.

9. The system of claim 8 where the patient alerting mechanism for an extended period of elevated heart rate utilizes a lower level of the at least two levels of severity.

10. The system as recited in claim 1 wherein said patient alerting mechanism is adapted to provide an alert to the patient selected from the group of: an audio signal, a vibration, a visual signal, and combinations thereof.

11. The system of claim 1 wherein the alert includes instructions to the user to take a beta blocker due to a detection of an extended period of elevated heart rate.

12. The system of claim 11 wherein the alert includes a text based alert.

13. The system of claim 1 wherein the alert includes a medication non-compliance notification that the patient may have skipped beta blocker medications.

14. The system of claim 1 wherein the system is further configured to accept a user response in response to a notification about beta blocker, said response comprising user input to a user device.

15. The system of claim 1 wherein the system is further configured to operate to perform an ischemia subroutine to determine if the patient is experiencing demand ischemia.

16. A system for detecting a cardiac event in a patient including:
at least two electrodes implanted in the patient for obtaining the electrical signal from the patient's heart, the electrical signal being an electrogram;
an implanted cardiac monitoring and alerting system devoid of circuitry adapted to deliver electrical energy through the electrodes to the patient's heart including:
(a) analog-to-digital converter circuitry for digitizing the electrogram to produce electrogram segments each having a time duration that is at least 1 second;
(b) at least one processor for processing a first electrogram segment at a first predetermined time to extract at least one baseline heart signal parameter value of the patient;
(c) computer memory contained within or coupled to said at least one processor for storing the at least one baseline heart signal parameter value, said computer memory further configured for storing lower and upper limits for the patient's normal heart rate range and an elevated heart rate range, the lower limit of the elevated heart rate range being at or above the upper limit of the normal heart rate range;
(d) means for processing a plurality of electrogram segments at a later, second predetermined time to extract at least one heart signal of the patient from said plurality of electrogram segments;
(e) a processor coupled to the memory means designed to detect the cardiac event when the at least one heart rate signal extracted at the second predetermined time shifts by more than a predetermined threshold amplitude from the at least one baseline heart signal parameter value extracted at the first predetermined time; and
(f) the processor further configured to compute the average heart rate of each of said electrogram segments, the processor further adapted to detect a prolonged period of electrogram segments having an elevated heart rate when the computed average heart rate is in the elevated heart rate range for at least 50% of electrogram segments over a pre-set time period.

17. The system of claim 16 wherein the cardiac event is an acute myocardial infarction.

18. The system of claim 16 wherein the heart signal parameter value is the average voltage of the ST segments of one or more beats of the electrogram segments.

19. The system of claim 16 wherein the heart signal parameter is the ST deviation of one or more beats of the electrogram segments.

20. The system of claim 16 further including memory means within the implanted cardiac monitor for storing the first electrogram segment.

21. The system of claim 16 further including an alarm sub-system within the implanted cardiac monitoring and alerting system, the alarm sub-system having the capability to warn the patient to the detection of at least one of the following selected from the group of: a cardiac event; and a prolonged period of elevated heart rate.

22. The system of claim 16 further including a vibrational alerting system within the implanted cardiac monitor, the vibrational alerting system having the capability to warn the patient that the cardiac event has occurred.

23. The system of claim 22 where the vibrational alerting mechanism is selected from the group comprising: a vibrator motor; a piezoelectric crystal; and a Linear Resonant Actuator (LRA).

24. The system of claim 16 where at least one of the electrodes is located within the right ventricle of the heart.

25. The system of claim 16 where at least one electrode is located subcutaneously.

26. The system of claim 16 where the processor is adapted to identify an extended period of elevated heart rate when the computed average heart rate is in the elevated heart rate range for at least 90% of electrogram segments over a pre-set time period.

27. The system of claim 16 where the processor is adapted to identify an extended period of elevated heart rate when the computed average heart rate is in the elevated heart rate range for 100% of electrogram segments over a pre-set time period.

28. The system of claim 16 where a Physician's Programmer having a Physician's Programmer processor is used to set the lower and upper limits for the patient's normal heart rate range and an elevated heart rate range, the lower limit of the elevated range being at or above the upper limit of the normal range.

29. The system of claim 16 where a Physician's Programmer having a Physician's Programmer processor is used to calculate the lower and upper limits for the patient's normal heart range and an elevated heart rate range, the lower limit of the elevated range being at or above the upper limit of the normal range.

30. An implanted cardiac monitoring device for monitoring the heart of a human patient, the device including:
   at least one connector for attaching to the device at least one implantable lead, the at least one lead including at least one electrode for sensing the electrical signal from the patient's heart;
   electronic circuitry devoid of circuitry adapted to deliver electrical energy through the at least one electrode to the patient's heart including:
   (a) analog-to-digital converter circuitry for digitizing the electrical signal sensed by the at least one electrode
   (b) means for processing the digitized electrical signal to compute the average heart rate over a multiplicity of pre-set periods of time;
   (c) digital memory for storing pre-set lower and upper limits for a normal range of patient heart rate and pre-set lower and upper limits for an elevated range of heart rate;
   (d) a processor coupled to the digital memory adapted to detect all of the abnormalities in patient heart rate selected from the group including:
      i. High heart rate when the average heart rate exceeds the upper limit of the elevated heart rate range for a high heart rate detection time period,
      ii. Low heart rate when the average heart rate is less than the lower limit of the normal heart rate range for a low heart rate detection time period,
      iii. Elevated heart rate when the average heart rate is between the lower limit of the elevated heart rate range and the upper limit of the elevated heart rate range for an elevated heart rate detection time period of more than 2 hours,
      iv. Irregular heart rate when the average heart rate of a first pre-set percentage of the beats in a measured over an irregular heart rate time period having R-R intervals more than a second pre-set percentage below the average heart rate for the irregular heart rate time period.

31. The implanted cardiac monitoring device of claim 30 wherein the elevated heart rate detection time period is more than 6 hours.

32. The implanted cardiac monitoring device of claim 30 having the digital memory further include a sequential number of sections of histogram memory, each of the sections having bins, with each of the bins associated with a range of R-R intervals, each range of R-R intervals corresponding to a range of associated heart rates, each of the sections being either an active section or an inactive section of histogram memory, only one of the sections to be active at a time, upon measurement of the R-R interval for a beat, the electrical circuitry adapted to increment by one the value in the bin associated with that R-R-interval within the active section of histogram memory, the apparatus adapted to utilize the active section for a pre-set time interval, at the end of the pre-set time interval, the active section will become inactive and the next section will become active for a preset time interval.

33. A system for monitoring a patient's heart rate and alerting the patient of an abnormal condition indicative of patient beta blocker non-compliance or improper beta blocker dosing, comprising:
   a physician's programmer adapted to allow its user to set one or more heart rate related parameters including from the group of (1) a normal heart rate range having an upper limit; (2) a high heart rate lower threshold for detecting tachycardia; and (3) an elevated heart rate range that lies between the normal heart rate range upper limit and the high heart rate lower threshold;
   an implanted device capable of wireless data communication with the physician's programmer having at least two implanted electrodes adapted to sense and store electrical signals from the heart of the patient and electronic circuitry devoid of circuitry adapted to deliver electrical energy through the electrodes to the patient's heart coupled to said at least two electrodes for sensing and electronically operating on said sensed electrical signals to provide operational electronic signals;
   the electronic circuitry including a processor adapted to compute an average heart rate of the patient during a pre-programmed time period for a multiplicity of heart beats, said processor further adapted to store the heart rate related parameters downloaded from the physician's programmer, and wherein said processor is further configured to responsively (a) detect excessive ST shifts as a function of said heart rate normal range, and (b) alert the patient of beta blocker non-compliance or improper beta blocker dosing following detection of a patient's heart rate meeting at least one beta blocker non-compliance detection criterion for a prolonged time period defined in the at least one beta blocker non-compliance detection criterion, said alert not being triggered by and alerting a patient to an inability to collect baseline data over a specified time period, and informing the user specifically about detection of cardiac activity reflective of beta blocker non-compliance or improper beta blocker dosing, and, a patient alerting mechanism adapted to alert the patient when the computed average heart rate for a portion of the multiplicity of heart beats during a pre-programmed time period is within the elevated heart rate range.

34. The system of claim 33 wherein the defined prolonged time period time period is at least 1 hour.

* * * * *